(12) United States Patent
Schuster et al.

(10) Patent No.: US 10,899,812 B2
(45) Date of Patent: Jan. 26, 2021

(54) **IMMUNOTHERAPY WITH A*01 RESTRICTED PEPTIDES AND COMBINATION OF PEPTIDES AGAINST CANCERS AND RELATED METHODS**

(71) Applicant: Immatics Biotechnologies GmbH, Tuebingen (DE)

(72) Inventors: Heiko Schuster, Tuebingen (DE); Annika Sonntag, Tuebingen (DE); Daniel Johannes Kowalewski, Kirchentellinsfurt (DE); Oliver Schoor, Tuebingen (DE); Jens Fritsche, Dusslingen (DE); Toni Weinschenk, Aichwald (DE); Harpreet Singh, Munich (DE); Colette Song, Ostfildern (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/916,833

(22) Filed: Jun. 30, 2020

(65) Prior Publication Data

US 2020/0325195 A1 Oct. 15, 2020

Related U.S. Application Data

(63) Continuation of application No. 16/575,250, filed on Sep. 18, 2019.

(60) Provisional application No. 62/732,863, filed on Sep. 18, 2018.

(30) Foreign Application Priority Data

Sep. 18, 2018 (DE) .................. 10 2018 122 900

(51) Int. Cl.
| | | |
|---|---|---|
| A61K 38/00 | (2006.01) |
| C07K 14/47 | (2006.01) |
| C07K 14/725 | (2006.01) |
| C07K 14/74 | (2006.01) |

(52) U.S. Cl.
CPC ...... *C07K 14/4748* (2013.01); *C07K 14/7051* (2013.01); *C07K 14/70539* (2013.01); *A61K 38/00* (2013.01)

(58) Field of Classification Search
CPC combination set(s) only.
See application file for complete search history.

(56) References Cited

U.S. PATENT DOCUMENTS

| | | | |
|---|---|---|---|
| 7,807,642 B2 | 10/2010 | Dengjel |
| 7,833,969 B2 | 11/2010 | Dengjel |
| 7,833,970 B2 | 11/2010 | Dengjel |
| 10,196,432 B2 | 2/2019 | Dengjel |
| 2008/0206216 A1 | 8/2008 | Dengjel |
| 2015/0125477 A1 | 5/2015 | Kuttruff-Coqui et al. |
| 2016/0115212 A1 | 4/2016 | Dengjel |

FOREIGN PATENT DOCUMENTS

| | | |
|---|---|---|
| EP | 1760088 A1 | 3/2007 |
| WO | 2007/028574 A2 | 3/2007 |
| WO | 2010037395 A2 | 4/2010 |

OTHER PUBLICATIONS

German Search Report of German Patent Application No. 10 2018 122 900.3 dated Apr. 17, 2019.

*Primary Examiner* — Lei Yao
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 34 Drawing Sheets

Specification includes a Sequence Listing.

Peptide: NSDISIPEY (A*01)
SEQ ID NO: 16

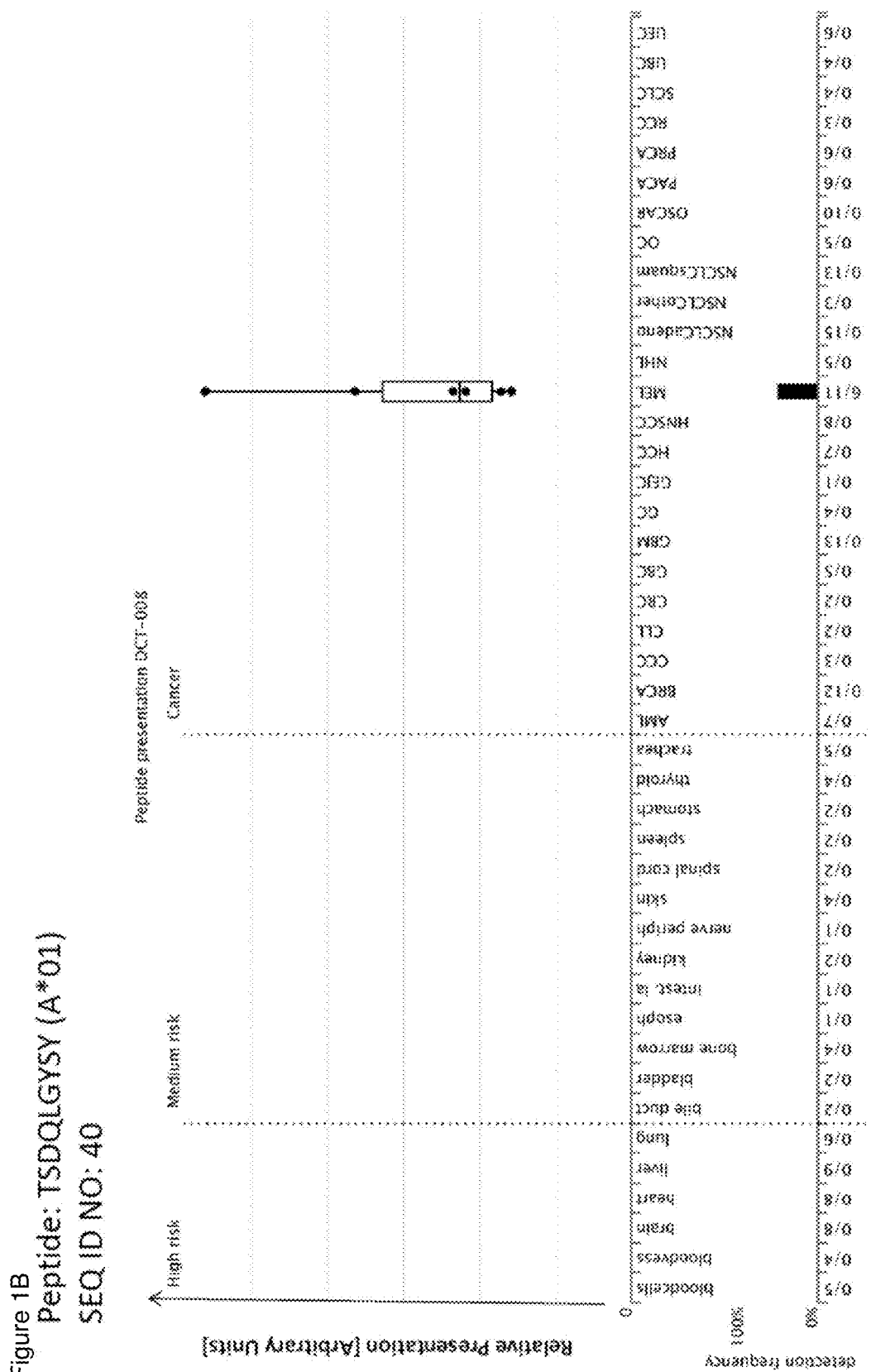
Figure 1B Peptide: TSDQLGYSY (A*01) SEQ ID NO: 40

Peptide: HSDLLEDSKY (A*01)
SEQ ID NO: 41

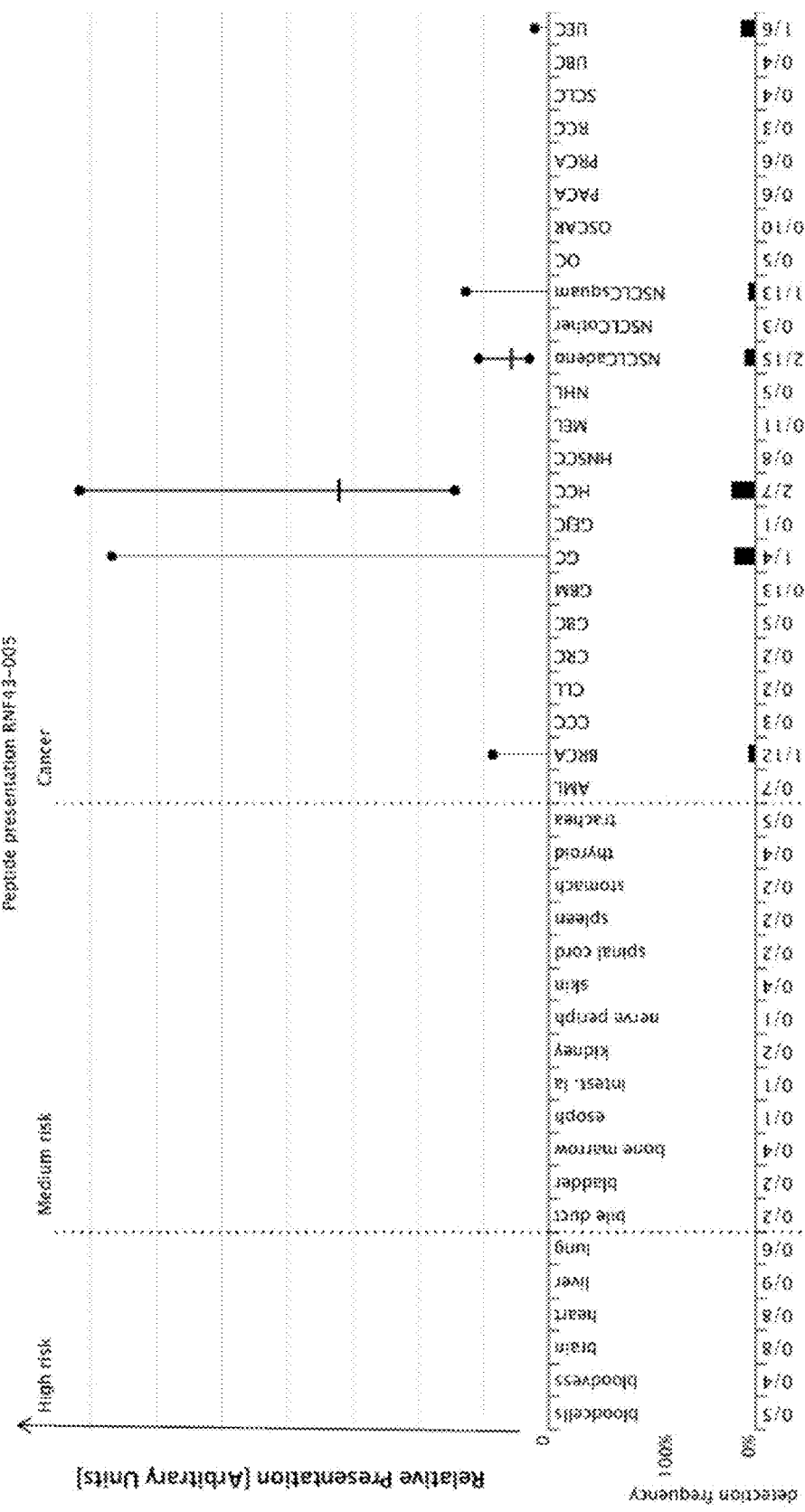

Peptide: YTELVEEKY (A*01)
SEQ ID NO: 70

Peptide: QTDVERIKDTY (A*01)
SEQ ID NO: 76

Peptide: QLDSAVKNLY (A*01)
SEQ ID NO: 78

Peptide: HMLAAMAY (A*01)
SEQ ID NO: 296

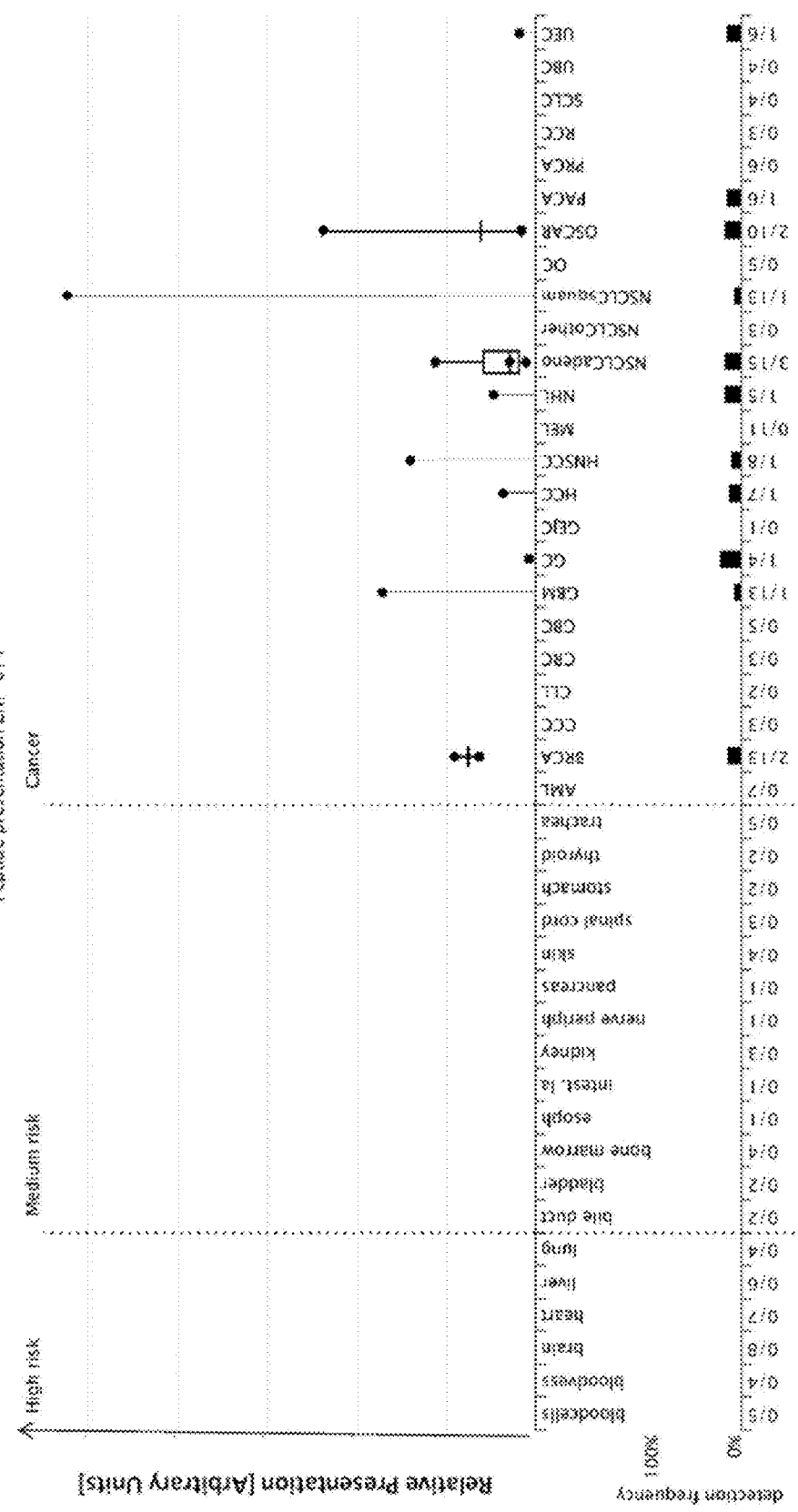

Peptide: NTDSMTLNNTAY (A*01)
SEQ ID NO: 329

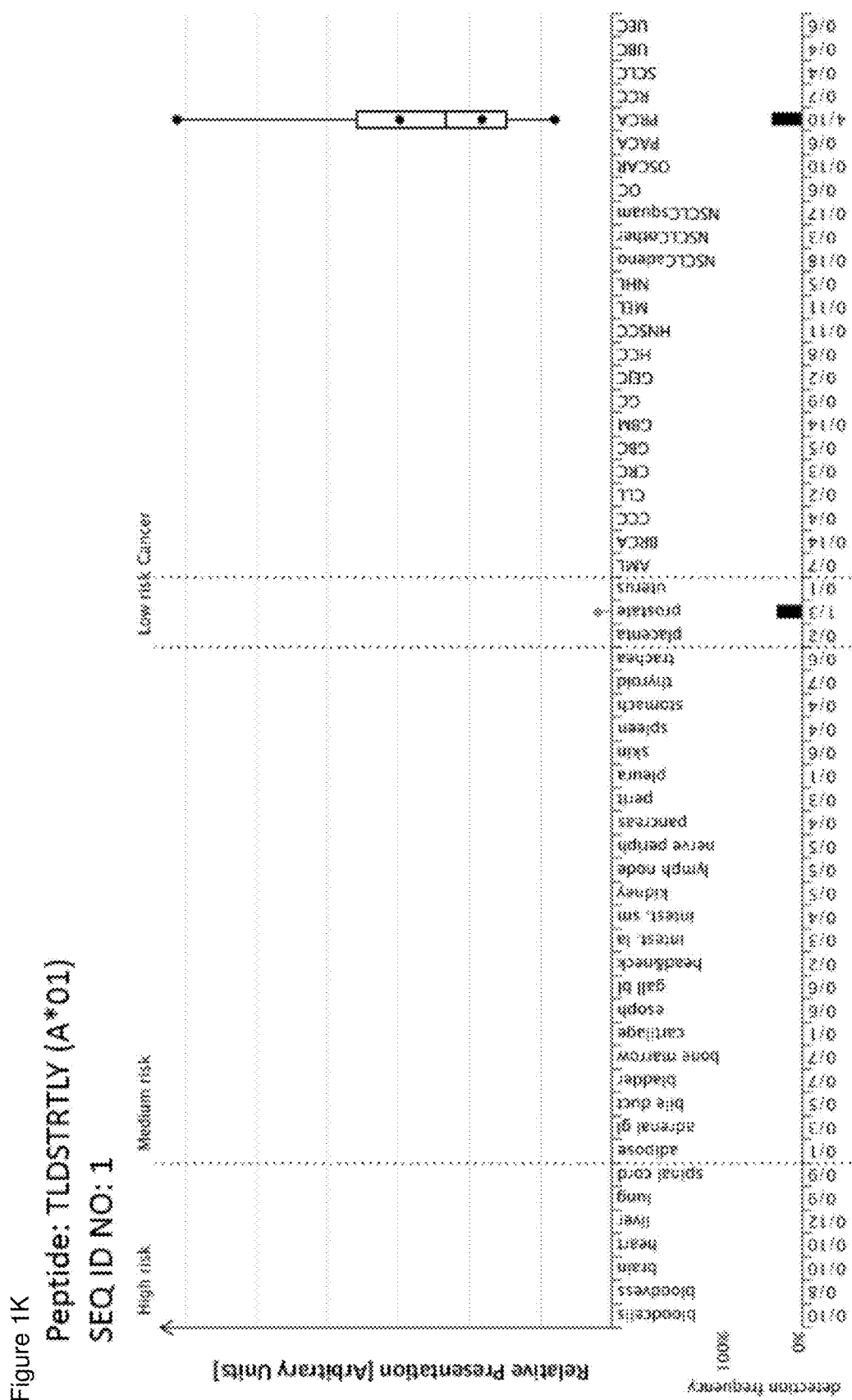
Figure 1K Peptide: TLDSTRTLY (A*01) SEQ ID NO: 1

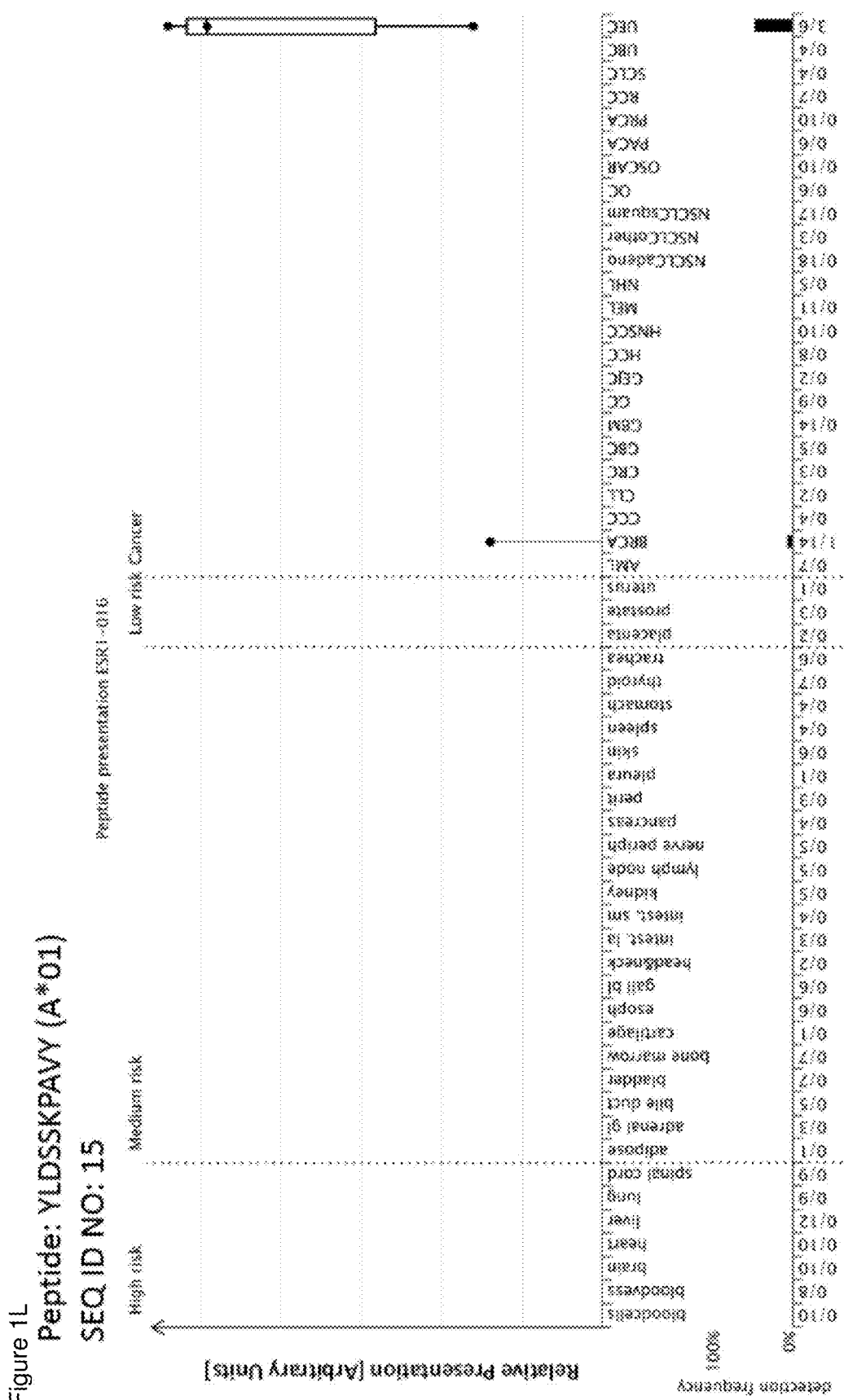
Figure 1L Peptide: YLDSSKPAVY (A*01) SEQ ID NO: 15

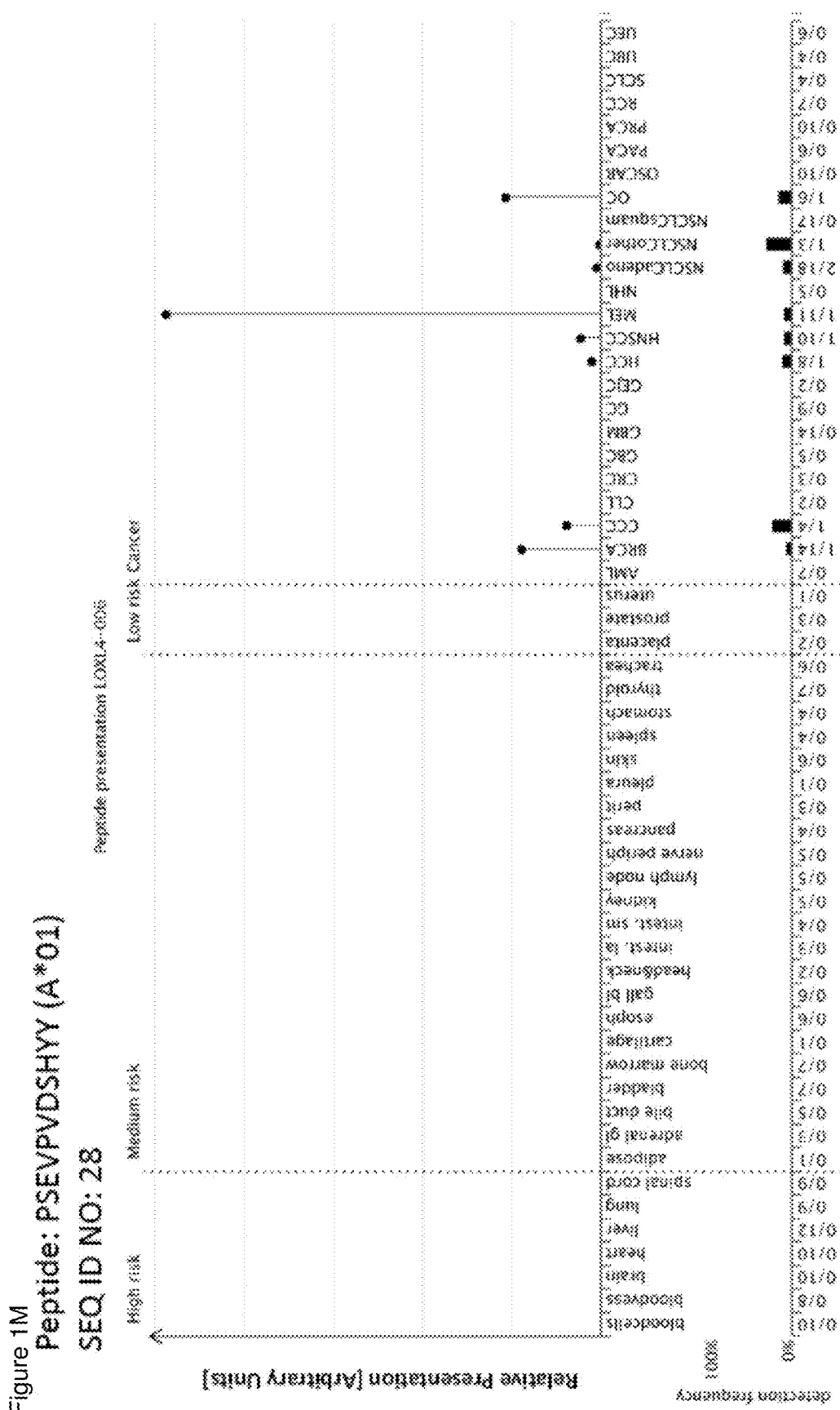
Figure 1M Peptide: PSEVPVDSHYY (A*01) SEQ ID NO: 28

Peptide: LMEKEDYHSLY (A*01)
SEQ ID NO: 387

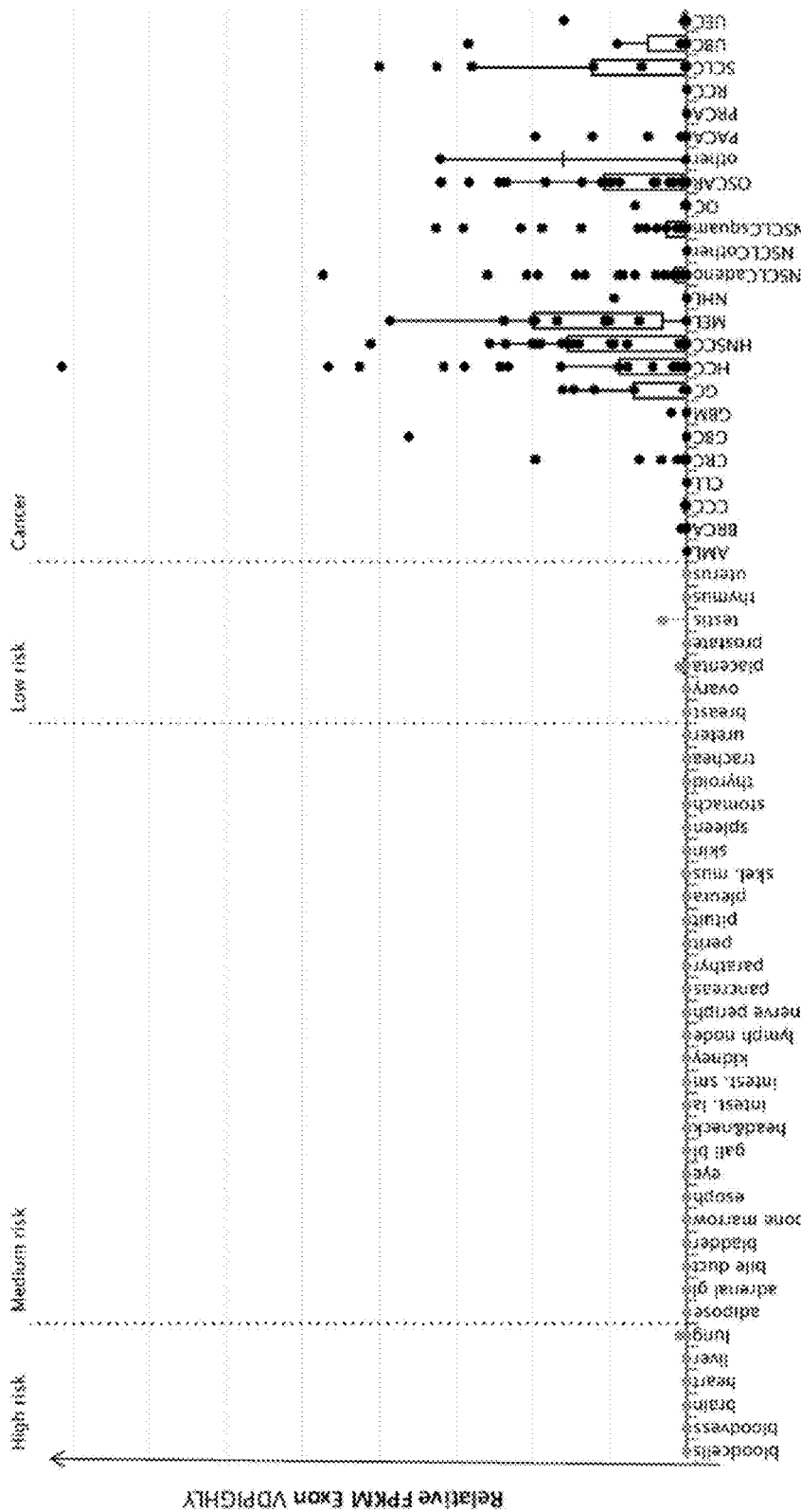

Gene: SLC6A3
Peptide: FGTTPAAEYF
SEQ ID NO: 3

Gene: UMOD1
Peptide: ARDPITFSF
SEQ ID NO: 6

Gene: SLC45A3
Peptide: ASDHWRGRY
SEQ ID NO: 11

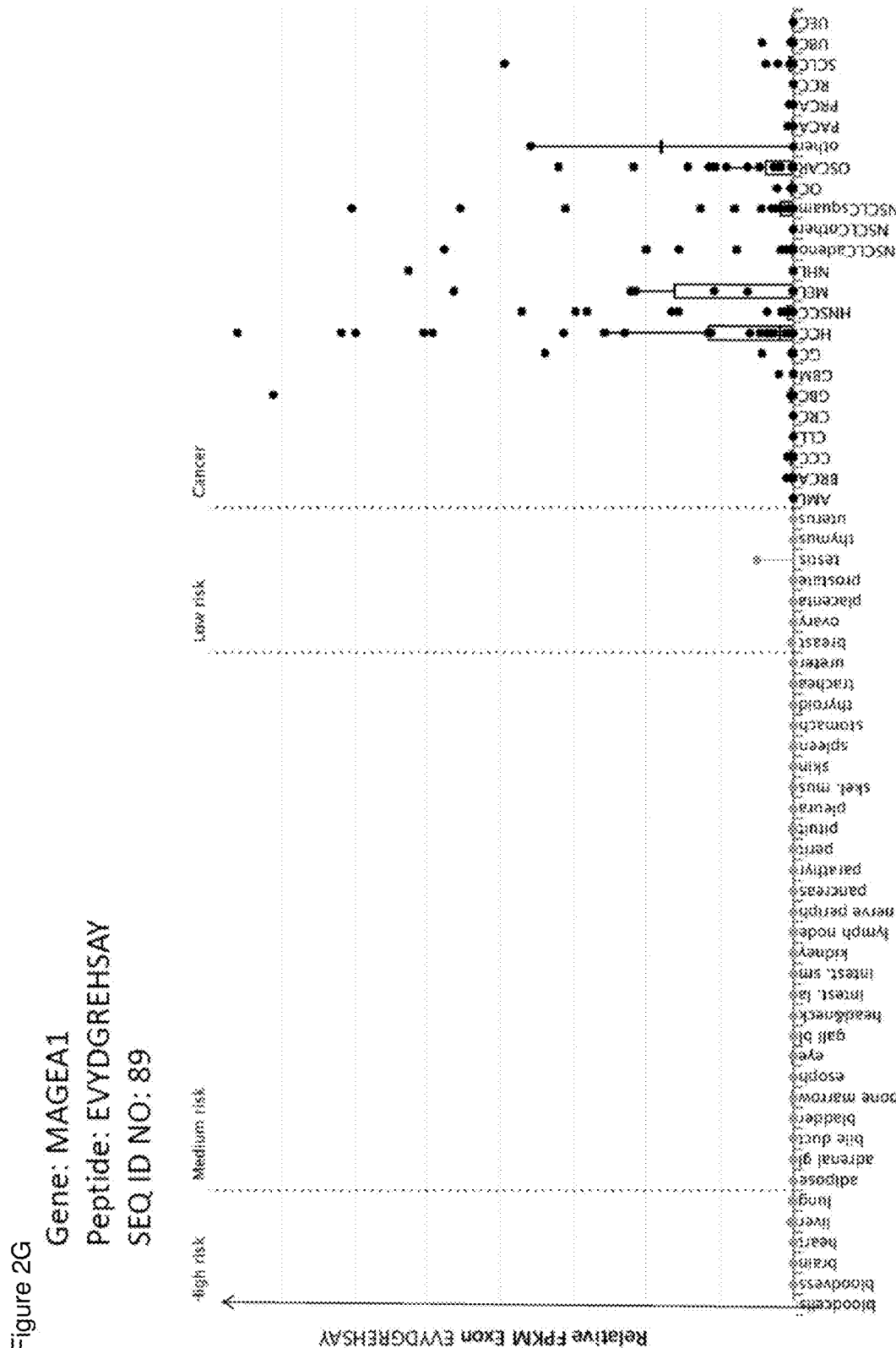

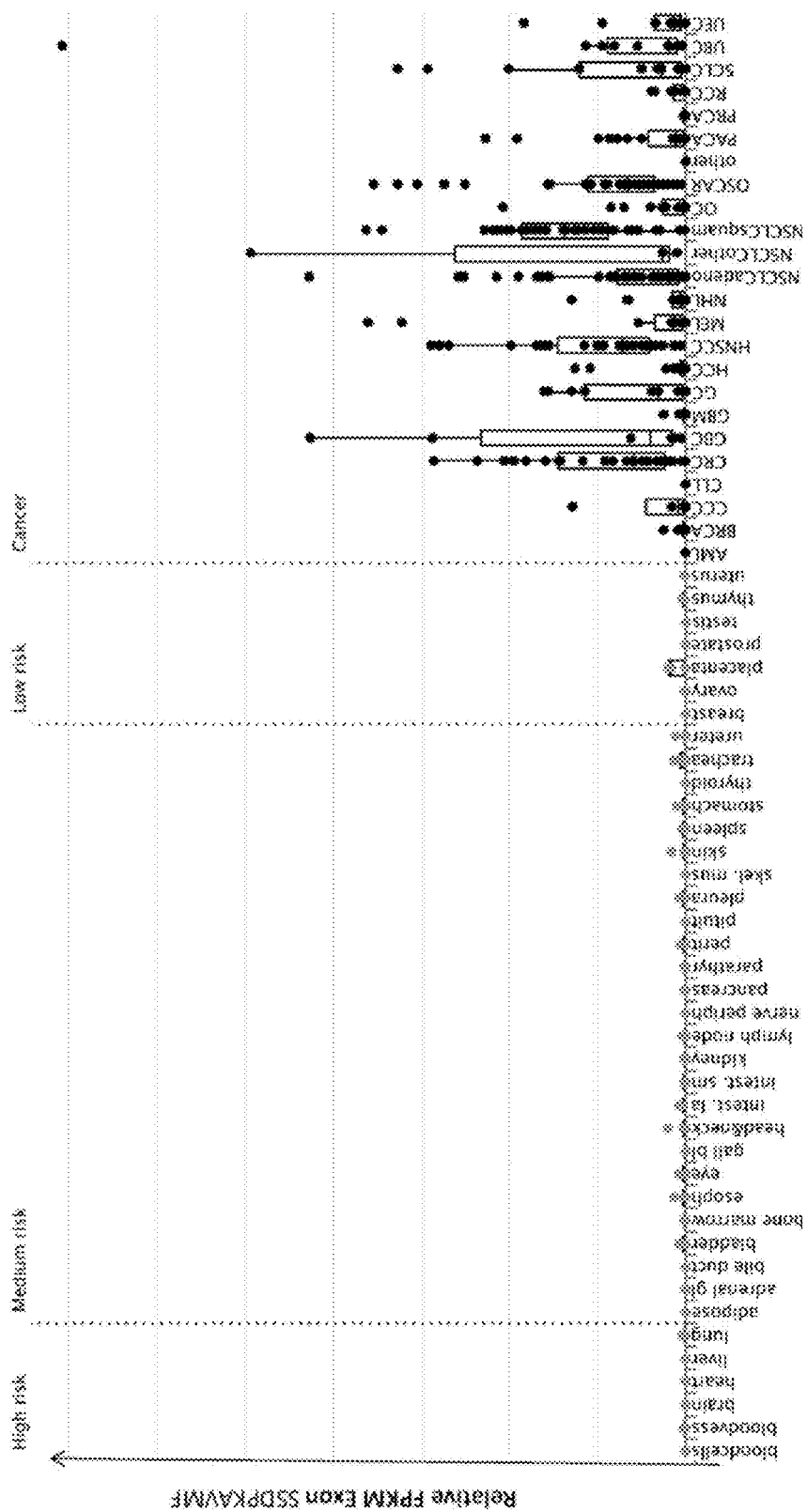

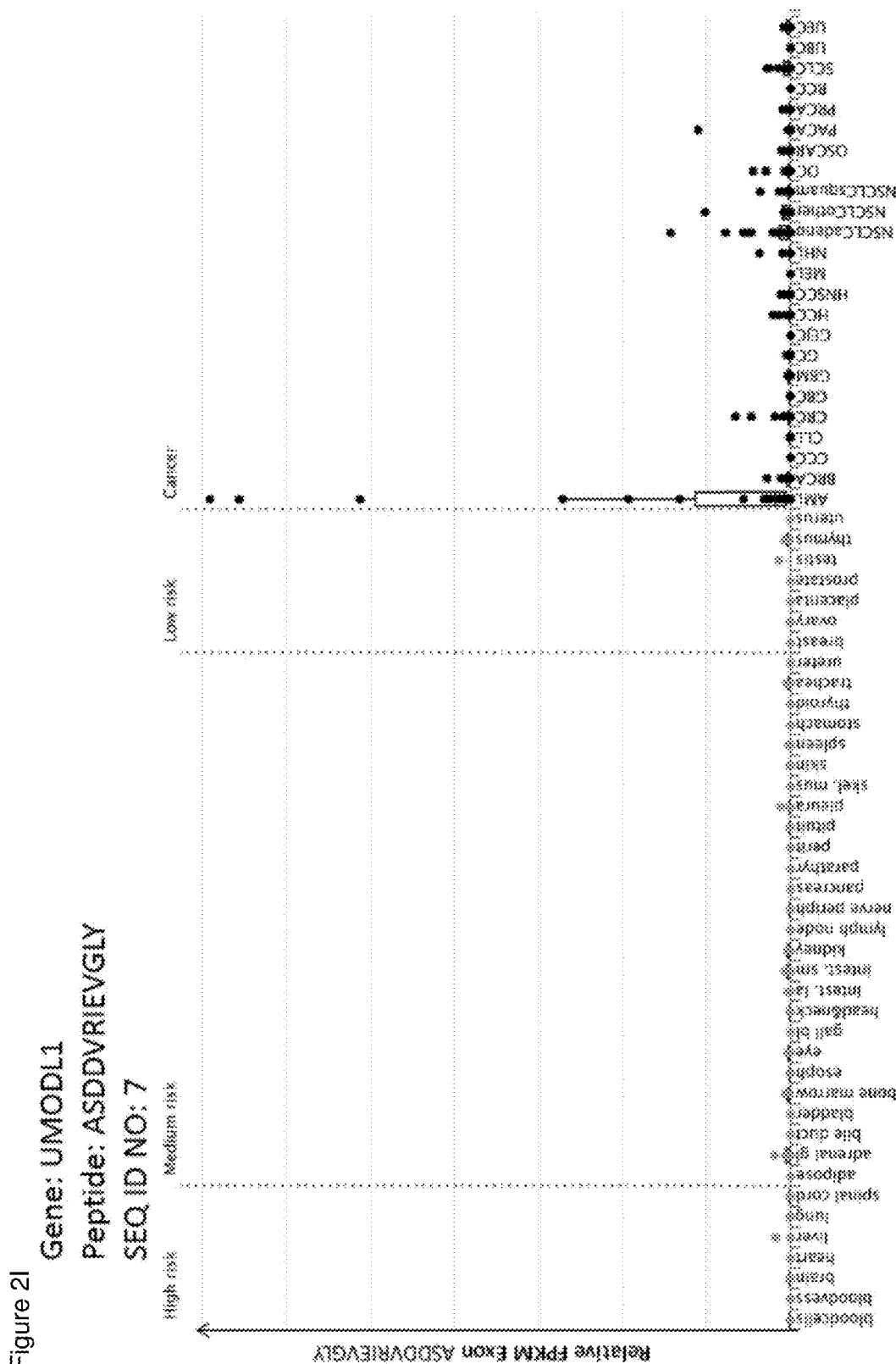
Figure 2I Gene: UMODL1 Peptide: ASDDVRIEVGLY SEQ ID NO: 7

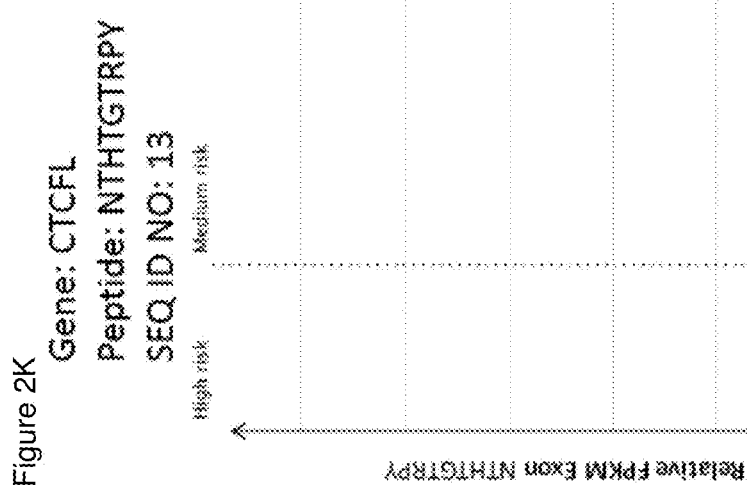

Gene: SOX14
Peptide: DTDPLKAAGL
SEQ ID NO: 23

Gene: HAS2, HAS3
Peptide: IATVIQLFY
SEQ ID NO: 66

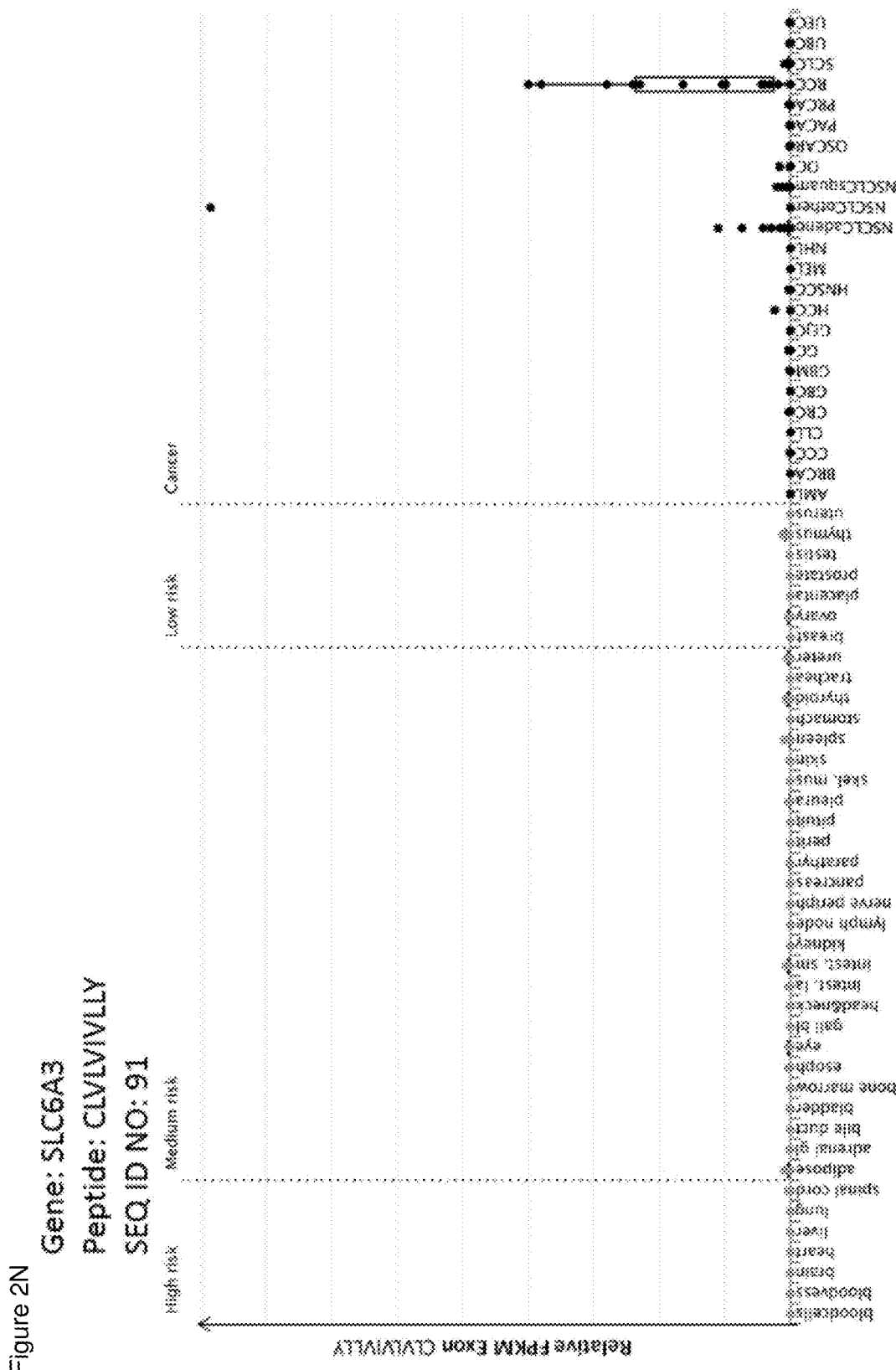

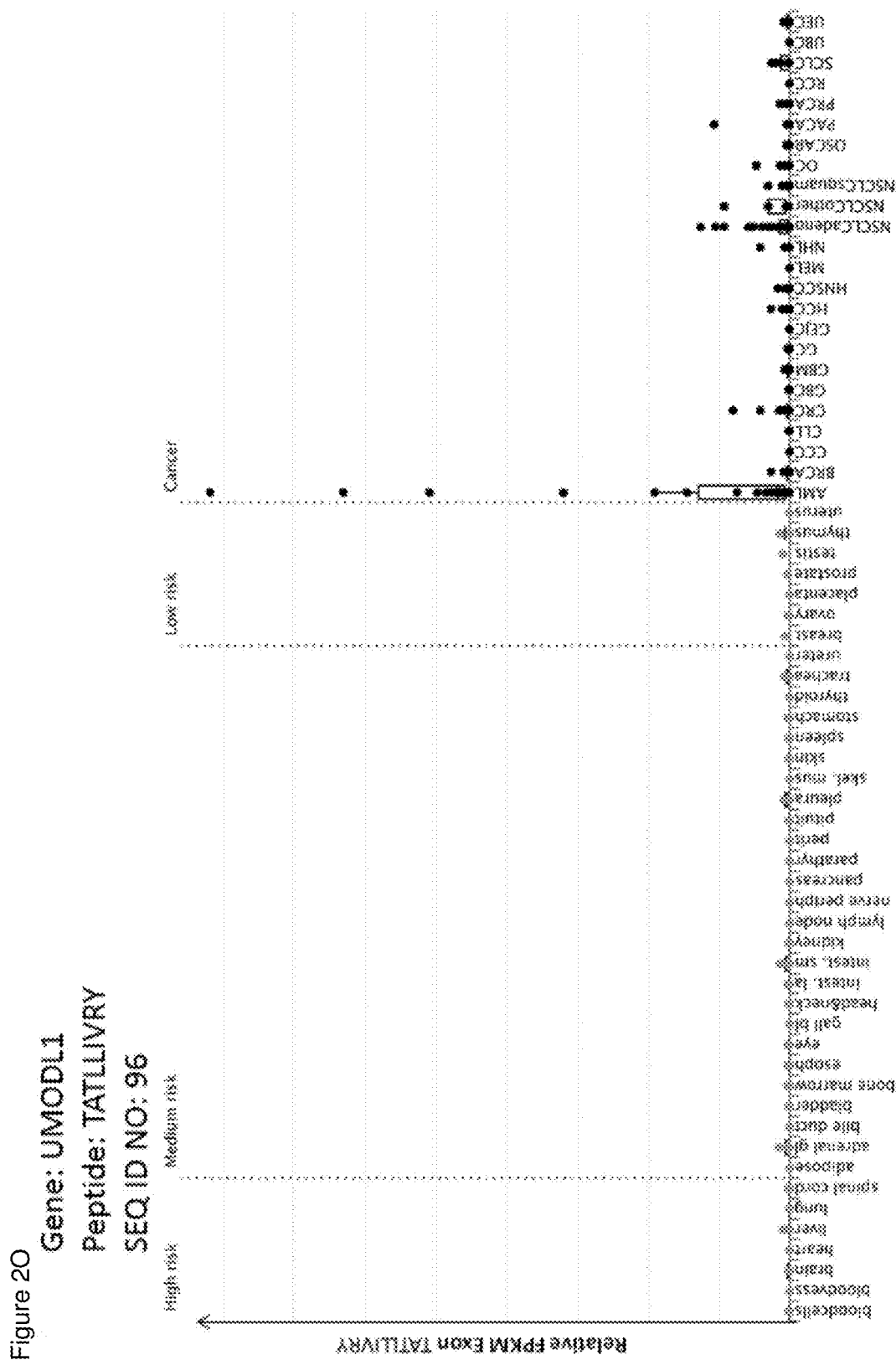

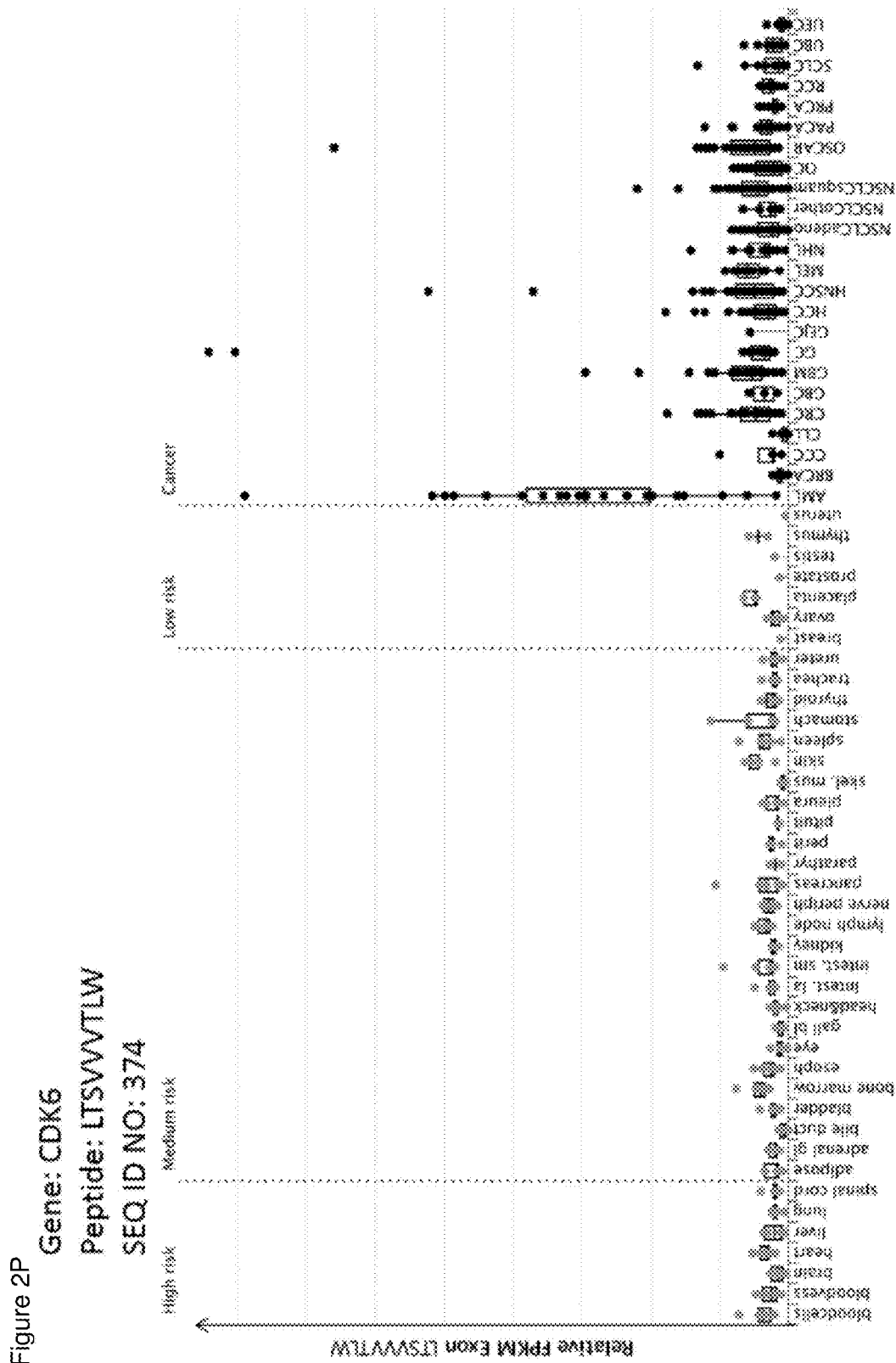

IMMUNOTHERAPY WITH A*01 RESTRICTED PEPTIDES AND COMBINATION OF PEPTIDES AGAINST CANCERS AND RELATED METHODS

CROSS-REFERENCE TO RELATED APPLICATIONS

This patent application is a Continuation of U.S. patent application Ser. No. 16/575,250, filed on 18 Sep. 2019, which claims the benefit of U.S. Provisional Patent Application No. 62/732,863, filed on 18 Sep. 2018 and German Application No. 10 2018 122 900.3, filed on 18 Sep. 2018, the contents of which are hereby incorporated by reference in their entireties.

This application is related to International Application No. PCT/EP2019/075065, filed 18 Sep. 2019.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-099002_ST25.txt" created on 30 Jun. 2020, and 68,247 bytes in size) is submitted concurrently with the instant application, and the entire contents of the Sequence Listing are incorporated herein by reference.

BACKGROUND

Field

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

Description of Related Art

According to the World Health Organization (WHO), cancer ranged among the four major non-communicable deadly diseases worldwide in 2012. For the same year, colorectal cancer, breast cancer and respiratory tract cancers were listed within the top 10 causes of death in high income countries.

Epidemiology

In 2012, 14.1 million new cancer cases, 32.6 million patients suffering from cancer (within 5 years of diagnosis) and 8.2 million cancer deaths were estimated worldwide (Bray et al., 2013; Ferlay et al., 2013).

Within the groups of brain cancer, leukemia and lung cancer the current invention specifically focuses on glioblastoma (GBM), chronic lymphocytic leukemia (CLL) and acute myeloid leukemia (AML), non-small cell and small cell lung cancer (NSCLC and SCLC), respectively.

GBM is the most common central nervous system malignancy with an age-adjusted incidence rate of 3.19 per 100,000 inhabitants within the United States. GBM has a very poor prognosis with a 1-year survival rate of 35% and a 5-year survival rate lower than 5%. Male gender, older age and ethnicity appear to be risk factors for GBM (Thakkar et al., 2014).

CLL is the most common leukemia in the Western world where it comprises about one third of all leukemia. Incidence rates are similar in the US and Europe, and estimated new cases are about 16,000 per year. CLL is more common in Caucasians than in Africans, rarer in Hispanics and Native Americans and seldom in Asians. In people of Asian origin, CLL incidence rates are 3-fold lower than in Caucasians (Gunawardana et al., 2008). The five-year overall survival for patients with CLL is about 79%.

AML is the second most common type of leukemia diagnosed in both adults and children. Estimated new cases in the United States are about 21,000 per year. The five-year survival rate of people with AML is approximately 25%.

Lung cancer is the most common type of cancer worldwide and the leading cause of death from cancer in many countries. Lung cancer is subdivided into small cell lung cancer and non-small cell lung cancer. NSCLC includes the histological types adenocarcinoma, squamous cell carcinoma and large cell carcinoma and accounts for 85% of all lung cancers in the United States. The incidence of NSCLC is closely correlated with smoking prevalence, including current and former smokers and the five-year survival rate was reported to be 15% (Molina et al., 2008; World Cancer Report, 2014).

Considering the severe side-effects and expense associated with treating cancer, there is a need to identify factors that can be used in the treatment of cancer in general and acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer in particular. There is also a need to identify factors representing biomarkers for cancer in general and acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer in particular, leading to better diagnosis of cancer, assessment of prognosis, and prediction of treatment success for people with the A*01 allele.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor- (-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses(Gnjatic et al., 2003). At the tumor site, T helper cells, support a cytotoxic T cell– (CTL–) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Longer (elongated) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated.

Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell-based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

BRIEF SUMMARY OF THE INVENTION

In a first aspect of the present invention, the present invention relates to a peptide comprising an amino acid sequence selected from the group consisting of SEQ ID NO: 1 to SEQ ID NO: 398 or a variant sequence thereof which is at least 77%, preferably at least 88%, homologous (preferably at least 77% or at least 88% identical) to SEQ ID NO: 1 to SEQ ID NO: 398, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 398 or a variant thereof, which is at least 77%, preferably at least 88%, homologous (preferably at least 77% or at least 88% identical) to SEQ ID NO: 1 to SEQ ID NO: 398, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. In Table 1, peptides with SEQ ID NO: 1 to SEQ ID NO: 385 bind to HLA-A*01. The peptides in Table have been disclosed before in large listings as results of high-throughput screenings with high error rates or calculated using algorithms but have not been associated with cancer at all before. In Table 2, peptides with SEQ ID NO: 386 to SEQ ID NO: 398 bind to HLA-A*01. The peptides in Table are additional peptides that may be useful in combination with the other peptides of the invention. In Table 3, peptides with SEQ ID NO: 399 to SEQ ID NO: 431 bind to HLA-A*01.

TABLE 1

Peptides according to the present invention.

| SEQ ID No. | Sequence | Gene(s) | HLA allotype |
|---|---|---|---|
| 1 | TLDSTRTLY | TRPM8 | A*01 |
| 2 | VDPIGHLY | MAGEA3 | A*01 |
| 3 | FGTTPAAEYF | SLC6A3 | A*01 |
| 4 | RIEAIRAEY | TRIM51, TRIM51EP, TRIM51GP, TRIM51HP | A*01 |
| 5 | FMVIAGMPLFY | SLC6A3 | A*01 |
| 6 | ARDPITFSF | UMODL1 | A*01 |
| 7 | ASDDVRIEVGLY | UMODL1 | A*01 |
| 8 | TSRAANIPGY | C7orf72 | A*01 |
| 9 | QLDSTLDSY | CYP4Z1, CYP4Z2P | A*01 |
| 10 | VSERTGISY | ITIH6 | A*01 |
| 11 | ASDHWRGRY | SLC45A3 | A*01 |
| 12 | YTDFVGEGLY | SLC45A3 | A*01 |
| 13 | NTHTGTRPY | CTCFL | A*01 |
| 14 | QSEKEPGQQY | RHOXF2, RHOXF2B | A*01 |
| 15 | YLDSSKPAVY | ESR1 | A*01 |
| 16 | NSDISIPEY | SCGB2A1 | A*01 |
| 17 | ASWAVLCYY | ANO7 | A*01 |
| 18 | RSDPVSLRY | COL20A1 | A*01 |
| 19 | LTEGHSGNY | FCRL5 | A*01 |
| 20 | LSAQHRMLA | EML6 | A*01 |
| 21 | LSSAVNPIIY | NMUR2 | A*01 |
| 22 | VMDTLGLFY | TRPM8 | A*01 |
| 23 | DTDPLKAAGL | SOX14 | A*01 |
| 24 | NLDHYTNAY | GLYATL3 | A*01 |
| 25 | AMMQEAQLAY | SOX1 | A*01 |
| 26 | ASDDFRSKY | KRT34, LOC100653049 | A*01 |
| 27 | PSEVPVDSHY | LOXL4 | A*01 |
| 28 | PSEVPVDSHYY | LOXL4 | A*01 |
| 29 | TLEDLDNLYNY | EPYC | A*01 |
| 30 | VTTDKPRAY | ITIH6 | A*01 |
| 31 | VSDHLQAGMLGQY | HEPHL1 | A*01 |
| 32 | GTDKQNSTLRY | HMCN1 | A*01 |
| 33 | SMDPVTGYQY | PAX3 | A*01 |
| 34 | SSWSAGENDSY | HRNR | A*01 |
| 35 | SWSAGENDSYS | HRNR | A*01 |
| 36 | MTSTEQSLY | GREB1 | A*01 |
| 37 | MTSTEQSLYY | GREB1 | A*01 |
| 38 | KSWSQSSSLMY | F5 | A*01 |
| 39 | WSQSSSLMY | F5 | A*01 |
| 40 | TSDQLGYSY | DCT | A*01 |
| 41 | HSDLLEDSKY | NAT1 | A*01 |
| 42 | ASDVDTLLK | PTPRZ1 | A*01 |
| 43 | ETEPERHLGSY | NKX3-1 | A*01 |
| 44 | IPSFNEMVY | PTPRZ1 | A*01 |
| 45 | NLDPNKIY | STK31 | A*01 |
| 46 | RSDPGGGGLAYAAY | MEX3B | A*01 |
| 47 | WSDGVPLLY | BCAN | A*01 |
| 48 | FTTQDELLVY | SEMG2 | A*01 |
| 49 | GSFSIQHTY | SEMG2 | A*01 |
| 50 | ITDEDEDMLSY | TSPY1, TSPY10, TSPY2, TSPY3, TSPY4, TSPY8, TSPY9P | A*01 |
| 51 | STEERRLNY | SEMG2 | A*01 |
| 52 | TTQDELLVY | SEMG2 | A*01 |
| 53 | YLEDRPLSQLY | LOXL4 | A*01 |
| 54 | EVDIHTIHY | HEPHL1 | A*01 |
| 55 | ATEGDVLNY | COL19A1 | A*01 |
| 56 | VTEYAEEIYQY | CCNA1 | A*01 |
| 57 | ASDPASSTSCY | CYP1A1 | A*01 |
| 58 | YLENSASWY | DLX5 | A*01 |
| 59 | FTDSQGNDIK | SLC45A2 | A*01 |
| 60 | MTEKFLFLY | ERVV-1, ERVV-2 | A*01 |
| 61 | SSDIVALGGFLY | KLHDC7B | A*01 |
| 62 | VSELVTTGHY | VCAN | A*01 |
| 63 | TSEISQNALMY | ROS1 | A*01 |
| 64 | TSEISQNALMYY | ROS1 | A*01 |
| 65 | SSDFDPLVY | RNF43, SUPT4H1 | A*01 |
| 66 | IATVIQLFY | HAS2, HAS3 | A*01 |
| 67 | NVDQNQNSY | HMCN1 | A*01 |

TABLE 1-continued

Peptides according to the present invention.

| SEQ ID No. | Sequence | Gene(s) | HLA allotype |
|---|---|---|---|
| 68 | QSLPEFGLTY | FERMT1 | A*01 |
| 69 | QSLPEFGLTYY | FERMT1 | A*01 |
| 70 | YTELVEEKY | CAPN6 | A*01 |
| 71 | LTDSTTRTTY | MUC3A | A*01 |
| 72 | VTDSTTKIAY | LOC101060740 | A*01 |
| 73 | STDSASYY | APOB | A*01 |
| 74 | EMEQQSQEY | KRT13, KRT16 | A*01 |
| 75 | FTDYELKAY | ABCB11 | A*01 |
| 76 | QTDVERIKDTY | LAMA3 | A*01 |
| 77 | FTSDTGLEY | DNMT3B | A*01 |
| 78 | QLDSAVKNLY | ZNF215 | A*01 |
| 79 | ASDLEPRELLSY | PCDHGB1 | A*01 |
| 80 | ELCPLPGTSAY | FBN3 | A*01 |
| 81 | YSDLHTPGRY | PTCHD4 | A*01 |
| 82 | LTEKSHIRY | C8orf48 | A*01 |
| 83 | DTEFHGGLHY | LOC100124692 | A*01 |
| 84 | ESEMIKFASYY | ABCB11 | A*01 |
| 85 | SSDNYEHWLY | SFMBT1 | A*01 |
| 86 | VDPASNTY | MAGEA4 | A*01 |
| 87 | AFDDIATYF | SSX1 | A*01/C*04 |
| 88 | KEVDPAGHSYI | MAGEA8, MAGEA9, MAGEA9B | A*01/B*49 |
| 89 | EVYDGREHSAY | MAGEA1 | A*01/A*25 |
| 90 | YEDHFPLLF | MAGEA10 | A*01/B*18 |
| 91 | CLVLVIVLLY | SLC6A3 | A*01 |
| 92 | TTDDTTAMASAS | MAGEA10 | A*01 |
| 93 | HLKILSPIY | UMODL1 | A*01 |
| 94 | KPSAVKDSIY | MMP26 | A*01/A*26 |
| 95 | SSDPKAVMF | MMP12 | A*01/C*05 |
| 96 | TATLLIVRY | UMODL1 | A*01 |
| 97 | FPAPPAHWFY | CYP4Z1, CYP4Z2P | A*01 |
| 98 | NFSDLVFTY | SOX11 | A*01/A*29 |
| 99 | AADSNPSEL | RLN1 | A*01/C*05 |
| 100 | TTSSAISWILY | CYP4Z1 | A*01 |
| 101 | SITDVDFIY | DNAH8 | A*01 |
| 102 | STIRGELFF | MMP11 | A*01/B*57 |
| 103 | ITDTLIHLM | ESR1 | A*01/C*05 |
| 104 | ITDTLIHL | ESR1 | A*01/C*05 |
| 105 | VVFDKSDLAKY | SLC45A3 | A*01/A*29 |
| 106 | EVVEGKEWGSFY | NPSR1 | A*01/A*26 |
| 107 | TTENSGNYY | FCRL5 | A*01 |
| 108 | NSNLKFLEV | NLRP7 | A*01 |
| 109 | ISEDKSISF | LOC100996718, OR9G1, OR9G9 | A*01/B*15 |
| 110 | IGDKVDAVY | MMP13 | A*01 |
| 111 | TPIPFDKILY | COL10A1 | A*01/B*35 |
| 112 | KASSVSAEDGY | TTC6 | A*01/B*57 |
| 113 | ASCRSSAEY | LAMC2 | A*01 |
| 114 | AVAAAAGASLY | MSX1 | A*01 |
| 115 | NEIDIHSIYFY | HEPHL1 | A*01/B*18 |
| 116 | RSDIGEFEW | FAM111B | A*01/B*58 |
| 117 | SPAKQFNIY | FAM111B | A*01/B*35 |
| 118 | LTWAHSAKY | LOXL4 | A*01 |
| 119 | TVFDENLSRY | HEPHL1 | A*01/C*12 |
| 120 | LVDENQSWY | HEPHL1 | A*01 |
| 121 | SADEAHGLL | NFE2L3 | A*01/C*05 |
| 122 | ISEAPLTEV | SLC45A2 | A*01/C*08 |
| 123 | LLKAKDILY | ACSM1 | A*01 |
| 124 | FLKVTGYDKDDY | HMCN1 | A*01 |
| 125 | FQYELRELY | HMCN1 | A*01/B*15 |
| 126 | TTDPKKFQY | HMCN1 | A*01 |
| 127 | VPFNLITEY | SLC45A2 | A*01/B*35 |
| 128 | YTEFVDATFTK | HEPHL1 | A*01 |
| 129 | STIDFRAGF | HMCN1 | A*01/B*57 |
| 130 | YIGLKGLYF | SLC45A2 | A*01/A*23 |
| 131 | LEDGIEQSAY | G2E3 | A*01 |
| 132 | RTHIGYKVY | HMCN1 | A*01 |
| 133 | ITDVGPGNY | LOXL4 | A*01 |
| 134 | SAPSSSGSPLY | T | A*01 |
| 135 | TFDKQIVLL | F5 | A*01/C*04 |
| 136 | RRLNFSGFGY | ASCL1 | A*01/B*27 |
| 137 | EAYLERIGY | NAT1, NAT2 | A*01/B*15 |

TABLE 1-continued

Peptides according to the present invention.

| SEQ ID No. | Sequence | Gene(s) | HLA allotype |
|---|---|---|---|
| 138 | IPVHDSVGVTY | PTPRZ1 | A*01/B*35 |
| 139 | PVHDSVGVTY | PTPRZ1 | A*01 |
| 140 | SQHIFTVSY | PTPRZ1 | A*01/B*15 |
| 141 | DAVAPGREY | F5 | A*01/B*35 |
| 142 | IEKFAVLY | PTPRZ1 | A*01/B*18 |
| 143 | HVSGQMLYF | PGR | A*01/A*29 |
| 144 | RTIEGDFLW | BCAN | A*01/A*32 |
| 145 | LSDAVHVEF | FCRL3 | A*01/C*05 |
| 146 | LCATVCGTEQY | MMP16 | A*01 |
| 147 | AQVQDTGRY | HMCN1 | A*01 |
| 148 | GTKQWVHARY | FCER2 | A*01/A*30 |
| 149 | PIMSSSQALY | HMCN1 | A*01 |
| 150 | FTTLSDLQTNMA | MEIOB | A*01 |
| 151 | YEVDTKLLSL | MEIOB | A*01 |
| 152 | YLEDRPLSQ | LOXL4 | A*01 |
| 153 | HSIEVFTHY | LOXL4 | A*01 |
| 154 | SIEVFTHY | LOXL4 | A*01 |
| 155 | HTMEVTVY | PMEL | A*01/B*15 |
| 156 | STALSILLL | BCAN | A*01 |
| 157 | GLIEVVTGY | IGF1R | A*01/B*15 |
| 158 | EVTDRNMLAF | TRPS1 | A*01/A*25 |
| 159 | RQAPGPARDY | KRT13, KRT17 | A*01/B*15 |
| 160 | EVLGEEMYAY | LOC101060117, TTC6 | A*01 |
| 161 | EAAPDIMHY | GREB1 | A*01/B*35 |
| 162 | IADNPQLSFY | ABCC11 | A*01 |
| 163 | KIRAEVLSHY | RALGPS2 | A*01/A*30 |
| 164 | KLAGTVFQY | ADAMTS12 | A*01 |
| 165 | VSVYNSYPY | NKX3-1 | A*01 |
| 166 | YHRICELLSDY | POTEE, POTEF | A*01 |
| 167 | RAVQPGETY | F5 | A*01/B*15 |
| 168 | VQPGETYTY | F5 | A*01/B*35 |
| 169 | TVDNANILL | JUP, KRT13, KRT17 | A*01/C*05 |
| 170 | VQIAKGMNY | EGFR | A*01/B*15 |
| 171 | ITDFGLAKL | EGFR | A*01/C*05 |
| 172 | FSEPFHLIV | FCRLA | A*01/C*12 |
| 173 | QSTTGVSHY | VCAN | A*01 |
| 174 | TSEVEGLAFVSY | VCAN | A*01 |
| 175 | GLEYEAPKLY | DNMT3B | A*01 |
| 176 | HTDLESPSAVY | BTBD16 | A*01 |
| 177 | LVDGKWQEF | BTBD16 | A*01 |
| 178 | TQRTSFQFY | ROS1 | A*01/B*15 |
| 179 | SSTDFTFASW | FERMT1 | A*01/A*25 |
| 180 | AQISDTGRY | HMCN1 | A*01 |
| 181 | SVTDLIGGKW | HTR7, HTR7P1 | A*01/B*57 |
| 182 | TQPELSSRY | ADAMTS12 | A*01/B*15 |
| 183 | LADTDLGMTF | OR51B4 | A*01/C*12 |
| 184 | KTIQEVAGY | EGFR | A*01/B*57 |
| 185 | NSDESADSEPHKY | PRDM15 | A*01 |
| 186 | AVSSGLFFY | CTLA4 | A*01/A*29 |
| 187 | TQKSVQVLAY | PTPRZ1 | A*01/B*15 |
| 188 | DIPDYLLQY | ELL3 | A*01/A*26 |
| 189 | FRGVFVHRY | STAG3 | A*01/C*07 |
| 190 | VSSTVHNLY | GREB1 | A*01/B*57 |
| 191 | FTRAFDQLRM | TKTL2 | A*01/A*26 |
| 192 | LAFYYGMY | SLC7A11 | A*01/B*15 |
| 193 | SQNGQLIHY | SLC5A4 | A*01 |
| 194 | CYTADNEMGY | ROS1 | A*01 |
| 195 | YTADNEMGYY | ROS1 | A*01 |
| 196 | RLAQYTIERY | GABRP | A*01/B*15 |
| 197 | NDEIDKLTGY | PDE11A | A*01 |
| 198 | KLTDYINANY | PTPRZ1 | A*01/B*15 |
| 199 | LCAAVLAKY | UGT1A3, UGT1A5 | A*01 |
| 200 | SLPEFGLTY | FERMT1 | A*01/B*15 |
| 201 | SLPEFGLTYY | FERMT1 | A*01/B*46 |
| 202 | QTDINGGSLK | GPR143 | A*01 |
| 203 | LSQDELSKF | NLRP2, PYDC2 | A*01 |
| 204 | NVKEAPTEY | BTLA | A*01/C*12 |
| 205 | RMQEGSEVY | BTLA | A*01/B*15 |
| 206 | RVFAVTLY | ABCC4 | A*01/B*15 |
| 207 | LLEGEDAHLTQY | JUP, KRT13, | A*01 |

TABLE 1-continued

Peptides according to the present invention.

| SEQ ID No. | Sequence | Gene(s) | HLA allotype |
|---|---|---|---|
| | | KRT17 | |
| 208 | LLISKAEDY | IGF1R | A*01/B*35 |
| 209 | EADPFLKYL | CCNA1 | A*01/B*35 |
| 210 | LLEADPFLKY | CCNA1 | A*01 |
| 211 | YLNEWGSRF | CDH3 | A*01 |
| 212 | MMTDLTSVY | LOC101060622, MUC3A | A*01/A*29 |
| 213 | VSDSTTEITY | MUC3A | A*01 |
| 214 | VQDPSLPVY | SOX30 | A*01 |
| 215 | DTLEAATSLY | PLEKHG4B | A*01 |
| 216 | NSMLDPLVY | HCAR1 | A*01 |
| 217 | LMDEGAVLTL | L1TD1 | A*01/C*17 |
| 218 | FTAQLQLY | ROS1 | A*01 |
| 219 | KTELETALYY | GOLGA6L2 | A*01 |
| 220 | DVERIKDTY | LAMA3 | A*01 |
| 221 | TDVERIKDTY | LAMA3 | A*01 |
| 222 | GSPDAVVSY | MAGEB6 | A*01/B*35 |
| 223 | NAVDVVPSSF | NLRP2 | A*01 |
| 224 | RTDEGDNRVW | LY6K | A*01/B*57 |
| 225 | STDPNIVRK | TAF7L | A*01/A*11 |
| 226 | QITPKHNGLY | PSG11 | A*01/B*15 |
| 227 | ESAPKEVSRY | PDE10A | A*01/A*26 |
| 228 | KSFDDIAKY | SSX7 | A*01/B*15 |
| 229 | MTDVFIDY | ABCB11 | A*01 |
| 230 | CVIETFHKY | TCHHL1 | A*01 |
| 231 | LLPLLVMAY | CXCR3 | A*01 |
| 232 | RYLNIVHATQLY | CXCR3 | A*01 |
| 233 | RINSATGQY | CLNK | A*01/A*30 |
| 234 | YTDLTTIQV | LRRC15 | A*01 |
| 235 | SIEIDHTQY | MYH4 | A*01 |
| 236 | VLDSLLAQY | IGF2BP1 | A*01 |
| 237 | AQEAAVFLTLY | DNAH8 | A*01 |
| 238 | ETDWGLLKGHTY | CAPN6 | A*01 |
| 239 | SSERGSPIEKY | TRPS1 | A*01 |
| 240 | EVLDSLLAQY | IGF2BP1 | A*01/A*25 |
| 241 | SLMVASLTY | TNFSF4 | A*01/B*15 |
| 242 | GTNLPTLLW | CDKAL1 | A*01/B*57 |
| 243 | LTSEDTGAY | CDKAL1 | A*01 |
| 244 | VTKYIAGPY | PSG4, PSG5, PSG6, PSG7, PSG9 | A*01 |
| 245 | LSDNAANRY | MED12L | A*01 |
| 246 | ARLEGEIATY | KRT36 | A*01 |
| 247 | SMIRVGTNY | RCOR2 | A*01/B*15 |
| 248 | VTDIDELGK | CDK6 | A*01 |
| 249 | GVGFTELEY | C9orf57 | A*01 |
| 250 | GYVCNACGLY | TRPS1 | A*01 |
| 251 | GIEMTYETY | SYCP2 | A*01 |
| 252 | DTTSHTYLQY | ADCY8 | A*01/A*25 |
| 253 | YLESHGLAY | CPA5 | A*01 |
| 254 | FLFNDALLY | FGD6 | A*01/A*29 |
| 255 | WELDSLEY | KIF26B | A*01 |
| 256 | HAFESNNFIY | MET | A*01/B*35 |
| 257 | KSEMNVNMKY | MET | A*01 |
| 258 | RPSSVLTIY | SLC44A5 | A*01/B*15 |
| 259 | APDEVVALL | KLHL35 | A*01 |
| 260 | KPTEDSANVY | DCC | A*01 |
| 261 | MTEGSTVNTEY | TEX15 | A*01 |
| 262 | NVKHFLNDLY | TEX15 | A*01 |
| 263 | DCMDTEGSYM | FBN3 | A*01 |
| 264 | YRDPVFVSL | CYP2W1 | A*01/B*39 |
| 265 | LSDIDSRYI | PRAMEF20, PRAMEF21 | A*01 |
| 266 | LTDSFLLRF | TTPA | A*01/B*57 |
| 267 | IVADDTVY | ADAM7 | A*01 |
| 268 | AILHHLYFY | ABCC4 | A*01/A*29 |
| 269 | LPSPAATIWDY | MACC1 | A*01/B*35 |
| 270 | DLKIDLAAQY | DNAH17 | A*01/A*25 |
| 271 | VAEPPVVCSY | LOC730110, ZNF492, ZNF98 | A*01 |
| 272 | IPQDECLRY | PRAMEF1, PRAMEF13, PRAMEF14, PRAMEF2 | A*01 |
| 273 | CGPNEINHFY | OR5M8 | A*01 |
| 274 | YADIHGDLL | PARD6B | A*01/C*05 |
| 275 | ESDEMENLLTY | SERHL, SERHL2 | A*01 |

TABLE 1-continued

Peptides according to the present invention.

| SEQ ID No. | Sequence | Gene(s) | HLA allotype |
|---|---|---|---|
| 276 | QITSFASGTSY | MED12L | A*01 |
| 277 | LPAPGFLFY | GDPGP1 | A*01/B*35 |
| 278 | AATVKSDIY | TEX14 | A*01 |
| 279 | LMTVLLKY | SLC16A14 | A*01 |
| 280 | TTEMVSNESVDY | MET | A*01 |
| 281 | YPDLSELLM | NUP155 | A*01/B*35 |
| 282 | QAMPSWPTAAY | NRG3 | A*01 |
| 283 | ETILVSSSY | SLC10A5 | A*01 |
| 284 | TCSHTFVYY | VWDE | A*01 |
| 285 | VLPHHSEGACVY | FRAS1 | A*01/B*15 |
| 286 | ATDMEGNLNY | CDH4 | A*01 |
| 287 | ENSIEDLQY | CCDC83 | A*01 |
| 288 | TEEKFVSY | TSPEAR | A*01 |
| 289 | YTSHEDIGY | SLC16A14 | A*01 |
| 290 | GQFTGTAGACRY | WT1 | A*01/B*15 |
| 291 | TSDVTGSLTY | GPR31 | A*01 |
| 292 | VLDFAPPGASAY | WT1 | A*01 |
| 293 | IISVLIAIY | SLC6A5 | A*01 |
| 294 | MMEMEGMY | DNAH8 | A*01 |
| 295 | GQRLDEAMISY | MYO3B | A*01/B*15 |
| 296 | HMLAAMAY | OR8G1, OR8G2, OR8G5 | A*01 |
| 297 | RLDEAMISY | MYO3B | A*01 |
| 298 | KFDVINHYF | OR8G5 | A*01 |
| 299 | EVDSVALSL | VRTN | A*01 |
| 300 | VSINPNSGDIY | PCDH19 | A*01 |
| 301 | ESQTCASDY | DCBLD1 | A*01 |
| 302 | FYLSTPENYHY | MYO10 | A*01/A*29 |
| 303 | GFGGLSSQGVYY | NKX6-3 | A*01 |
| 304 | FSENLIYTYI | MYO1H | A*01 |
| 305 | YADLLIYTY | MYO3B | A*01 |
| 306 | KSFETTVRY | FMN1 | A*01/C*12 |
| 307 | DTDDRELRY | FREM2 | A*01 |
| 308 | ELAAGQVVY | FREM2 | A*01/B*18 |
| 309 | EVDRNLIQY | FREM2 | A*01 |
| 310 | KAFQELGVRY | FREM2 | A*01/B*57 |
| 311 | TVTDGTHTDFY | FREM2, FREM3 | A*01 |
| 312 | VTDGINPLI | FREM2 | A*01 |
| 313 | VTDGTHTDFY | FREM2, FREM3 | A*01 |
| 314 | PPEANSLQGALY | DBX2 | A*01 |
| 315 | VLKIELETY | CCDC6 | A*01/B*15 |
| 316 | YTCEECGQAF | ZNF479, ZNF679, ZNF727, ZNF733P, ZNF734P | A*01 |
| 317 | EDLLEVLDMY | KCNH7 | A*01/B*18 |
| 318 | YMTSMALNY | ITGAE | A*01 |
| 319 | FTDPHIITF | VWDE | A*01/C*04 |
| 320 | QALQDKLQTFY | VWDE | A*01 |
| 321 | DGIADASNLSYY | LOC100124692, LOC93432 | A*01 |
| 322 | FSELNPLALY | TDRD5 | A*01 |
| 323 | KTLQKPVLPLY | DNMBP | A*01/A*30 |
| 324 | RTGIFPYRF | DNMBP | A*01/B*57 |
| 325 | LQKPVLPLY | DNMBP | A*01/B*15 |
| 326 | STSRLTLFS | DMXL1 | A*01 |
| 327 | IMLSVDQHLY | RAPGEF5 | A*01 |
| 328 | LLDEDNNIKL | HUNK | A*01 |
| 329 | NTDSMTLNNTAY | EFCAB5 | A*01 |
| 330 | EGELSEGEHWY | ZNF827 | A*01 |
| 331 | YLYQAPGSLALY | IRX2 | A*01 |
| 332 | SLISFKYTSY | FRAS1 | A*01 |
| 333 | LSDPQAELQFY | PCDHGB6 | A*01 |
| 334 | PSSMPECLSY | SOX30 | A*01 |
| 335 | PSSMPECLSYY | SOX30 | A*01 |
| 336 | ATNIQLNIDTY | CCDC175 | A*01 |
| 337 | FTESNQYNIY | FSTL4 | A*01 |
| 338 | YSPDSFNVSW | USH2A | A*01 |
| 339 | ESMDIFPLGW | SFMBT1 | A*01/A*25 |
| 340 | SVDSNLVAY | DMXL1 | A*01 |
| 341 | PANYLGKMTY | ARHGEF38 | A*01/B*15 |
| 342 | QTYMDGLLHY | LAMA3 | A*01/B*15 |
| 343 | YFGNYFTYY | C5orf34 | A*01 |
| 344 | AVNALQSVY | CPA6 | A*01/B*15 |

TABLE 1-continued

Peptides according to the present invention.

| SEQ ID No. | Sequence | Gene(s) | HLA allotype |
|---|---|---|---|
| 345 | NTMDAVPRIDHY | SLC12A2 | A*01 |
| 346 | VAGLEAGVLY | UMODL1 | A*01 |
| 347 | SADHPGLTF | FREM2 | A*01/C*05 |
| 348 | DSTDGCLLSF | TBC1D16 | A*01 |
| 349 | HLLSVSLYY | OR5AC2, OR5H14, OR5H2, OR5H6 | A*01 |
| 350 | LTDPQVSYV | FARP2 | A*01 |
| 351 | VLDPMLDFY | FAM46D | A*01 |
| 352 | YPVVVAESMY | FAM46D | A*01 |
| 353 | RLNGSVASY | FAM46D | A*01 |
| 354 | EIIRYIFAY | HPGDS | A*01/A*26 |
| 355 | MADRGEARL | RMI2 | A*01/C*04 |
| 356 | NSENHILKY | C12orf56 | A*01 |
| 357 | MSPDIALLYL | OVCH1 | A*01 |
| 358 | YMSPDIALLY | OVCH1 | A*01 |
| 359 | NKEINYFMY | ADCY10 | A*01/A*32 |
| 360 | RFDDINQEF | DNAH17 | A*01/C*04 |
| 361 | FTAEEGQLY | AR | A*01 |
| 362 | SGALDEAAAY | AR | A*01 |
| 363 | LTDRDVSFY | MROH2B | A*01 |
| 364 | DTGYLQLYY | STON2 | A*01 |
| 365 | FVDTKVPEH | ABCC12 | A*01 |
| 366 | ITVDVRDEF | STON2 | A*01/B*57 |
| 367 | LTDTGYLQLY | STON2 | A*01 |
| 368 | ESAATGQLDY | TNR | A*01 |
| 369 | AVMEAAFVY | TXNDC16 | A*01/A*29 |
| 370 | RLSTIRHLY | MXRA5 | A*01/A*32 |
| 371 | WSDSTSQTIY | SH3PXD2A | A*01 |
| 372 | SRSDFEWVY | DEGS2 | A*01/C*07 |
| 373 | FHADSDDESF | CDCA7 | A*01/B*38 |
| 374 | LTSVVVTLW | CDK6 | A*01/B*57 |
| 375 | ASSLDSLHY | PTPRT | A*01 |
| 376 | EDDEDEDLY | HSD17B4 | A*01 |
| 377 | YADPSANRDLL | ST8SIA5 | A*01/B*35 |
| 378 | TAKAPSTEY | GALNT5 | A*01/B*15 |
| 379 | SLIIDDTEY | FSIP2 | A*01/B*35 |
| 380 | VACGNNPVY | FSIP2 | A*01/B*15 |
| 381 | ETSFSTSHY | NRG1 | A*01/A*26 |
| 382 | YEPATMEQY | MYO10 | A*01 |
| 383 | PPDHAVGRTKY | GCNT2 | A*01 |
| 384 | RFRSITQSYY | RAB30 | A*01/A*30 |
| 385 | SANALILTY | RAB30 | A*01/B*35 |

TABLE 2

Additional peptides according to the present invention with no prior known cancer association.

| SEQ ID No. | Sequence | Gene(s) | HLA allotype |
|---|---|---|---|
| 386 | NSALNPLLY | KISS1R | A*01 |
| 387 | LMEKEDYHSLY | TYR, TYRL | A*01 |
| 388 | YTAHVGYSMY | MSX1 | A*01 |
| 389 | YYDLVESTF | DNTT | A*01 |
| 390 | FSEPFHLIVSY | FCRLA | A*01 |
| 391 | GSNPARYEF | MAGEA4 | A*01/B*57 |
| 392 | TQHFVQENY | MAGEA3 | A*01/B*15 |
| 393 | QVWGGQPVY | PMEL | A*01/B*35 |
| 394 | QVPLDCVLY | PMEL | A*01 |
| 395 | ILKGGSGTY | PMEL | A*01/B*15 |
| 396 | LPDPNVQKY | PRDM15 | A*01/C*04 |
| 397 | NSAINPLIY | NPSR1 | A*01 |
| 398 | YYYDTHTNTY | SLC12A2 | A*01/C*14 |

TABLE 3

Peptides useful for e.g. personalized cancer therapies.

| SEQ ID No. | Sequence | Gene(s) | HLA allotype |
|---|---|---|---|
| 399 | YVGKEHMFY | MAGEA9, MAGEA9B | A*01 |
| 400 | NTDNNLAVY | CXorf61 | A*01 |
| 401 | VWSNVTPLKF | MMP12 | A*01 |
| 402 | VLYPVPLESY | PRAME | A*01 |
| 403 | SADDIRGIQSLY | MMP12 | A*01 |
| 404 | FVDNQYWRY | MMP12 | A*01 |

TABLE 3-continued

Peptides useful for e.g. personalized cancer therapies.

| SEQ ID No. | Sequence | Gene(s) | HLA allotype |
|---|---|---|---|
| 405 | STDIGALMY | MMP1 | A*01 |
| 406 | SDVTPLTF | MMP11 | A*01 |
| 407 | VSIRNTLLY | FLT3 | A*01 |
| 408 | VWSDVTPLTF | MMP11 | A*01 |
| 409 | YTFRYPLSL | MMP11 | A*01 |
| 410 | KTWAHCMSY | KISS1R | A*01 |
| 411 | LLDAEPPILY | ESR1 | A*01 |
| 412 | AAAANAQVY | ESR1 | A*01 |
| 413 | TDTLIHLM | ESR1 | A*01 |
| 414 | LTEGHSGNYY | FCRL5 | A*01 |
| 415 | VWSDVTPLNF | MMP13 | A*01 |
| 416 | LSSPVHLDF | FCRL5 | A*01 |
| 417 | KLDRSVFTAY | FAM111B | A*01 |
| 418 | LLDEGAMLLY | NLRP7 | A*01 |
| 419 | FPTEVTPHAF | PTPRZ1 | A*01 |
| 420 | VTDLEMPHY | PTPRZ1 | A*01 |
| 421 | RSDPGGGGLAY | MEX3B | A*01 |
| 422 | ALNPYQYQY | DLX5 | A*01 |
| 423 | LLDEGAKLLY | NLRP2 | A*01 |
| 424 | NVDPVQHTY | AGRN | A*01 |
| 425 | VTEEPQRLFY | BMF | A*01 |
| 426 | RSFNGLLTMY | LAMB3 | A*01 |
| 427 | LTDYINANY | PTPRZ1 | A*01 |
| 428 | IINESLLFY | GPR143 | A*01 |
| 429 | VSDSECLSRY | LAMA1 | A*01 |
| 430 | NTDPTAPPY | CDH3 | A*01 |
| 431 | ASSTDSASYY | APOB | A*01 |
| 432 | LQSSGLTLLL | MSLNL | A*01 |

As can be seen from the above tables, many of the preferred peptides of the invention are surprisingly able to bind to at last two HLA allotypes. This allows for, in particular, broader applicability of these peptides.

The present invention furthermore generally relates to the peptides according to the present invention for use in the treatment of proliferative diseases, such as, for example, acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

Particularly preferred are the peptides—alone or in combination—according to the present invention selected from the group consisting of SEQ ID NO: 1 to SEQ ID NO: 398. More preferred are the peptides—alone or in combination—selected from the group consisting of SEQ ID NO: 1 to SEQ ID NO: 21 (see Table), and their uses in the immunotherapy of acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer, and preferably acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

Thus, another aspect of the present invention relates to the use of the peptides according to the present invention for the—preferably combined—treatment of a proliferative disease selected from the group of acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 398.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii) or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 398, preferably containing SEQ ID No. 1 to SEQ ID No. 21, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer, and preferably acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer cells.

The present invention further relates to biomarkers based on the peptides according to the present invention, herein called "targets" that can be used in the diagnosis of cancer, preferably acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length but can be as short as 8 amino acids in length, and as long as 10, 11, 12, 13, or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 4

Expression frequencies F of HLA-A*02, HLA-A*01, HLA-A*03, HLA-A*24, HLA-B*07, HLA-B*08 and HLA-B*44 serotypes. Haplotype frequencies Gf are derived from a study which used HLA-typing data from a registry of more 6.5 million volunteer donors in the U.S. (Gragert et al., 2013). The haplotype frequency is the frequency of a distinct allele on an individual chromosome. Due to the diploid set of chromosomes within mammalian cells, the frequency of genotypic occurrence of this allele is higher and can be the calculated employing the Hardy-Weinberg principle ($F = 1 - (1-Gf)^2$).

| Allele | Population | Calculated phenotype from allele frequency (F) |
|---|---|---|
| A*02 | African (N = 28557) | 32.3% |
|  | European Caucasian (N = 1242890) | 49.3% |
|  | Japanese (N = 24582) | 42.7% |
|  | Hispanic, S + Cent Amer. (N = 146714) | 46.1% |
|  | Southeast Asian (N = 27978) | 30.4% |
| A*01 | African (N = 28557) | 10.2% |
|  | European Caucasian (N = 1242890) | 30.2% |
|  | Japanese (N = 24582) | 1.8% |
|  | Hispanic, S + Cent Amer. (N = 146714) | 14.0% |
|  | Southeast Asian (N = 27978) | 21.0% |
| A*03 | African (N = 28557) | 14.8% |
|  | European Caucasian (N = 1242890) | 26.4% |
|  | Japanese (N = 24582) | 1.8% |
|  | Hispanic, S + Cent Amer. (N = 146714) | 14.4% |
|  | Southeast Asian (N = 27978) | 10.6% |
| A*24 | African (N = 28557) | 2.0% |
|  | European Caucasian (N = 1242890) | 8.6% |
|  | Japanese (N = 24582) | 35.5% |
|  | Hispanic, S + Cent Amer. (N = 146714) | 13.6% |
|  | Southeast Asian (N = 27978) | 16.9% |
| B*07 | African (N = 28557) | 14.7% |
|  | European Caucasian (N = 1242890) | 25.0% |
|  | Japanese (N = 24582) | 11.4% |
|  | Hispanic, S + Cent Amer. (N = 146714) | 12.2% |
|  | Southeast Asian (N = 27978) | 10.4% |
| B*08 | African (N = 28557) | 6.0% |
|  | European Caucasian (N = 1242890) | 21.6% |
|  | Japanese (N = 24582) | 1.0% |
|  | Hispanic, S + Cent Amer. (N = 146714) | 7.6% |
|  | Southeast Asian (N = 27978) | 6.2% |
| B*44 | African (N = 28557) | 10.6% |
|  | European Caucasian (N = 1242890) | 26.9% |
|  | Japanese (N = 24582) | 13.0% |
|  | Hispanic, S + Cent Amer. (N = 146714) | 18.2% |
|  | Southeast Asian (N = 27978) | 13.1% |

The peptides of the invention, preferably when included into a vaccine of the invention as described herein bind to A*01. A vaccine may also include pan-binding MHC class II peptides. Therefore, the vaccine of the invention can be used to treat cancer in patients that are A*01-positive, whereas no selection for MHC class II allotypes is necessary due to the pan-binding nature of these peptides.

If A*01 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

TABLE 5

HLA alleles coverage in European Caucasian population (calculated from (Gragert et al., 2013)).

| | coverage (at least one A-allele) | combined with B*07 | combined with B*44 | combined with B*07 and B*44 |
|---|---|---|---|---|
| A*02/A*01 | 70% | 78% | 78% | 84% |
| A*02/A*03 | 68% | 76% | 76% | 83% |
| A*02/A*24 | 61% | 71% | 71% | 80% |
| A*01/A*03 | 52% | 64% | 65% | 75% |
| A*01/A*24 | 44% | 58% | 59% | 71% |
| A*03/A*24 | 40% | 55% | 56% | 69% |
| A*02/A*01/A*03 | 84% | 88% | 88% | 91% |
| A*02/A*01/A*24 | 79% | 84% | 84% | 89% |
| A*02/A*03/A*24 | 77% | 82% | 83% | 88% |
| A*01/A*03/A*24 | 63% | 72% | 73% | 81% |
| A*02/A*01/A*03/A*24 | 90% | 92% | 93% | 95% |

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid (s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 398 or a variant thereof which is 88% homologous to SEQ ID NO: 1 to SEQ ID NO: 398, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 398. For example, a peptide may be modified so that it at least maintains, if not improves, the ability to interact with and bind to the binding groove of a suitable MHC molecule, such as HLA-A*02 or -DR, and in that way, it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Godkin et al., 1997; Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 398, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

In an aspect, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, A→I, T→V, A→M, T→I, A→V, T→G, and/or T→S.

In an aspect, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another aspect, conservative substitutions may be made in accordance with Table A. Methods for predicting tolerance to protein modification may be found in, for example, Guo et al., *Proc. Natl. Acad. Sci., USA*, 101(25):9205-9210 (2004), the contents of which are incorporated by reference in their entirety.

TABLE A

Conservative Amino Acid Substitutions

| Amino Acid | Substitutions (others are known in the art) |
| --- | --- |
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In another aspect, conservative substitutions may be those shown in Table B under the heading of "conservative substitutions." If such substitutions result in a change in biological activity, then more substantial changes, denominated "exemplary substitutions" in Table B, may be introduced and the products screened if needed.

TABLE B

Amino Acid Substitutions

| Original Residue (naturally occurring amino acid) | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 1, 4, 9, 10, and 12.

| Position | 1 | 2 | 3 | 4 | 5 | 6 | 7 | 8 | 9 | 10 |
|---|---|---|---|---|---|---|---|---|---|---|
| Seq ID No 1 | T | L | D | S | T | R | T | L | Y | |
| Variant |  |  | S |  |  |  |  |  |  |  |
|  |  |  | S |  |  |  |  |  | A |  |
|  |  |  | S |  | E |  |  |  |  |  |
|  |  |  | S |  | E |  |  |  | A |  |
|  |  |  | T |  |  |  |  |  |  |  |
|  |  |  | T |  |  |  |  |  | A |  |
|  |  |  | T |  | E |  |  |  |  |  |
|  |  |  | T |  | E |  |  |  | A |  |
| Seq ID No 4 | R | I | E | A | I | R | A | E | Y | |
| Variant |  |  | S | D |  |  |  |  |  |  |
|  |  |  | S | D |  |  |  |  | A |  |
|  |  |  | S |  |  |  |  |  |  |  |
|  |  |  | S |  |  |  |  |  | A |  |
|  |  |  | T | D |  |  |  |  |  |  |
|  |  |  | T | D |  |  |  |  | A |  |
|  |  |  | T |  |  |  |  |  |  |  |
|  |  |  | T |  |  |  |  |  | A |  |
| Seq ID No 9 | Q | L | D | S | T | L | D | S | Y | |
| Variant |  |  | S |  |  |  |  |  |  |  |
|  |  |  | S |  |  |  |  |  | A |  |
|  |  |  | S |  | E |  |  |  |  |  |
|  |  |  | S |  | E |  |  |  | A |  |
|  |  |  | T |  |  |  |  |  |  |  |
|  |  |  | T |  |  |  |  |  | A |  |
|  |  |  | T |  | E |  |  |  |  |  |
|  |  |  | T |  | E |  |  |  | A |  |
| Seq ID No 10 | V | S | E | R | T | G | I | S | Y | |
| Variant |  |  | D |  |  |  |  |  |  |  |
|  |  |  | D |  |  |  |  |  | A |  |
|  |  |  |  |  |  |  |  |  | A |  |
|  |  |  | T | D |  |  |  |  |  |  |
|  |  |  | T | D |  |  |  |  | A |  |
|  |  |  | T |  |  |  |  |  |  |  |
|  |  |  | T |  |  |  |  |  | A |  |
| Seq ID No 12 | T | T | D | F | V | G | E | G | L | Y |
| Variant |  |  |  | S |  |  |  |  |  |  |
|  |  |  |  | S |  |  |  |  |  | A |
|  |  |  |  | S | E |  |  |  |  |  |
|  |  |  |  | S | E |  |  |  |  | A |
|  |  |  |  |  |  |  |  |  |  | A |

TABLE 6-continued

Variants and motif of the peptides according to SEQ ID NO: 1, 4, 9, 10, and 12.

| Position | 1 | 2 | 3 | 4 | 5 | 6 | 7 | 8 | 9 | 10 |
|---|---|---|---|---|---|---|---|---|---|---|
|  |  |  |  |  | E |  |  |  |  |  |
|  |  |  |  |  | E |  |  |  |  | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to an MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 398.

"Consisting essentially of" shall mean that a peptide according to the present invention, in addition to the sequence according to any of SEQ ID NO: 1 to SEQ ID NO 398 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid, residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004(Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Another embodiment of the present invention relates to a non-naturally occurring peptide wherein said peptide consists or consists essentially of an amino acid sequence according to SEQ ID NO: 1 to SEQ ID NO: 398 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $K_1$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, Lit, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$, such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981), and by references as cited therein. Temporary N-amino group protection is afforded by the 9-fluorenylmethyloxycarbonyl (Fmoc) group. Repetitive cleavage of this highly base-labile protecting group is done using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by anyone, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1, FIGS. 1A-1N).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer samples (N=155 samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 155 acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer tissue samples were purified and HLA-associated peptides were isolated and analyzed by LC-MS (see example 1). All TUMAPs contained in the present application were identified with this approach on acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer samples confirming their presentation on acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

TUMAPs identified on multiple acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Besides over-presentation of the peptide, mRNA expression of the underlying gene was tested. mRNA data were obtained via RNASeq analyses of normal tissues and cancer tissues (cf. Example 2, FIGS. 2A-2P). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

The present invention provides peptides that are useful in treating cancers/tumors, preferably acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer that over- or exclusively present the peptides of the invention. These peptides were shown by mass spectrometry to be naturally presented by HLA molecules on primary human acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy blood cells, blood vessels, brain, heart, liver, lung, bile duct, bladder, bone marrow, esophagus, large intestine, kidney, peripheral nerve, pancreas, skin, spinal cord, spleen, stomach, thyroid, trachea cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer, but not on normal tissues (see Example 1).

HLA-bound peptides can be recognized by the immune system, specifically T lymphocytes. T cells can destroy the cells presenting the recognized HLA/peptide complex, e.g. acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill and can be found in the respective literature as well (see also below). Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides according to the invention capable of binding to TCRs and antibodies when presented by an MHC molecule.

The present description also relates to fragments of the TCRs according to the invention that are capable of binding to a peptide antigen according to the present invention when presented by an HLA molecule. The term particularly relates to soluble TCR fragments, for example TCRs missing the transmembrane parts and/or constant regions, single chain TCRs, and fusions thereof to, for example, with Ig.

The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V) and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise, the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A1-restricted pathogens have KD values that are generally about 10-fold lower when compared to TCRs specific for HLA-A1-restricted tumor-associated self-antigens (this holds true for other alleles as well). It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to peptides can be enhanced by methods well known in the art.

The present description further relates to a method of identifying and isolating a TCR according to the present description, said method comprising incubating PBMCs from HLA-A*01-negative healthy donors with A*01/peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with a peptide, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs(Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced (Schmitt et al., 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3 (CD3 fusion) (Schmitt et al., 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 398, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbas and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment, the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen and would thus be considered useful in the medicament of the present invention. Suitable adjuvants include, but are not limited to, 1018 ISS, aluminum salts, AMPLIVAX®, AS15, BCG, CP-870,893, CpG7909, CyaA, dSLIM, flagellin or TLR5 ligands derived from flagellin, FLT3 ligand, GM-CSF, 1030, 1031, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also, cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, immune checkpoint inhibitors including ipilimumab, nivolumab, pembrolizumab, atezolizumab, avelumab, durvalumab, and cemiplimab, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, atezolizumab, bevacizumab, interferon-alpha, interferon-beta, CpG oligonucleotides and derivatives, poly-(I:C) and derivatives, RNA, sildenafil, particulate formulations with PLG, virosomes, interleukin (IL)-1, IL-2, IL-4, IL-7, IL-12, IL-13, IL-15, IL-21, and IL-23.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 398, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen (preferably a peptide according to the present invention), the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is thus a further aspect of the invention to provide an antibody that specifically binds to a human major histocompatibility complex (MHC) class I or II being complexed with an HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 398, or a variant thereof which is at least 88% homologous (preferably identical) to SEQ ID NO: 1 to SEQ ID NO: 398 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 398 or a variant thereof which is at least 88% homologous (preferably identical) to SEQ ID NO: 1 to SEQ ID NO: 398, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 398.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 398 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

In an aspect, the activated T cells may be produced by contacting in vitro T cells with antigen loaded human class I or II MHC molecules presented on the surface of a suitable antigen-presenting cell or an artificial construct mimicking an antigen-presenting cell for a period of time sufficient to activate said T cells.

The present invention further relates to a method of killing target cells in a patient, in which the target cells aberrantly express a polypeptide comprising any amino acid sequence according to the present invention, the method comprising administering to the patient an effective number of T cells as according to the present invention.

The present invention further relates to a method of treating a patient who has cancer, in which the cancer cells aberrantly express a polypeptide comprising any amino acid sequence according to the present invention, the method comprising administering to the patient an effective number of T cells as produced according to the present invention.

The present invention further relates to a method of eliciting an immune response in a patient who has cancer, in which the cancer cells aberrantly express a polypeptide comprising any amino acid sequence according to the present invention, the method comprising administering to the patient an effective number of T cells as produced according to the present invention.

In an aspect, the T cells may be autologous to the patient. In another aspect, the T cells may be obtained from a healthy donor. In another aspect, the T cells may be derived from tumor infiltrating lymphocytes or peripheral blood mononuclear cells. In another aspect, the immune response may include cytotoxic T cell response.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer cells or other solid or hematological tumor cells such as acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, pancreatic cancer, prostate cancer, renal cell carcinoma, urinary bladder carcinoma, uterine and endometrial cancer.

The present invention further relates to particular marker proteins and biomarkers based on the peptides according to the present invention, herein called "targets" that can be used in the diagnosis and/or prognosis of acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of an acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer marker (poly)peptide, delivery of a toxin to an acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer cell expressing a cancer marker gene at an increased level, and/or inhibiting the activity of an acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer marker polypeptide) according to the invention.

Whenever possible, the antibodies of the invention may be purchased from commercial sources. The antibodies of the invention may also be generated using well-known methods. The skilled artisan will understand that either full length acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer marker polypeptides or fragments thereof may be used to generate the antibodies of the invention. A polypeptide to be used for generating an antibody of the invention may be partially or fully purified from a natural source or may be produced using recombinant DNA techniques.

For example, a cDNA encoding a peptide according to the present invention, such as a peptide according to SEQ ID NO: 1 to SEQ ID NO: 398 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1\times10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of an MHC class I epitope being used as an antigen; the T cells are CD8-positive T cells.

If an antigen-presenting cell is transfected to express such an epitope, preferably the cell comprises an expression vector capable of expressing a peptide containing SEQ ID NO: 1 to SEQ ID NO: 398, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, and vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 398.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but, in the tumor, it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer, the medicament of the invention is preferably used to treat acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced or may be pre-manufactured and stored. The warehouse (e.g. in the form of a database) is composed of tumor-associated peptides which were highly overexpressed in the tumor tissue of acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer patients with various HLA-A HLA-B and HLA-C alleles. It may contain MHC class I and MHC class II peptides or elongated MHC class I peptides. In addition to the tumor associated peptides collected from several acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer tissues, the warehouse may contain HLA-A*02, HLA-A*01, HLA-A*03, HLA-A*24, HLA-B*07, HLA-B*08 and HLA-B*44 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer samples from patients and blood from healthy donors were analyzed in a stepwise approach:

1. HLA ligands from the malignant material were identified by mass spectrometry

2. Genome-wide messenger ribonucleic acid (mRNA) expression analysis was used to identify genes over-expressed in the malignant tissue (acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer) compared with a range of normal organs and tissues 3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs 5. The relevance of over-expression at the mRNA level was confirmed by redetection of selected TUMAPs from step 3 on tumor tissue and lack of (or infrequent) detection on healthy tissues.

6. In order to assess, whether an induction of in vivo T-cell responses by the selected peptides may be feasible, in vitro immunogenicity assays were performed using human T cells from healthy donors as well as from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patient's tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

FIG. 1A) Peptide: NSDISIPEY (SEQ ID NO.: 16), FIG. 1B) Peptide: TSDQLGYSY (SEQ ID NO.: 40), FIG. 1C) Peptide: HSDLLEDSKY (SEQ ID NO.: 41), FIG. 1D) Peptide: SSDFDPLVY (SEQ ID NO.: 65), FIG. 1E) Peptide: YTELVEEKY (SEQ ID NO.: 70), FIG. 1F) Peptide: QTDVERIKDTY (SEQ ID NO.: 76), FIG. 1G) Peptide: QLDSAVKNLY (SEQ ID NO.: 78), FIG. 1H) Peptide: HMLAAMAY (SEQ ID NO.: 296), FIG. 1I) Peptide: YTCEECGQAF (SEQ ID NO.: 316), FIG. 1J) Peptide: NTDSMTLNNTAY (SEQ ID NO.: 329), FIG. 1K) Peptide: TLDSTRTLY (SEQ ID NO.: 1), FIG. 1L) Peptide:

YLDSSKPAVY (SEQ ID NO.: 15), FIG. 1M) Peptide: PSEVPVDSHYY (SEQ ID NO.:28), and FIG. 1N) Peptide: LMEKEDYHSLY (SEQ ID NO.: 387).

FIGS. 2A through 2P show exemplary expression profile of source genes of the present invention that are overexpressed in different cancer samples. Tumor (black dots) and normal (grey dots) samples are grouped according to organ of origin. Box-and-whisker plots represent median FPKM value, 25th and 75th percentile (box) plus whiskers that extend to the lowest data point still within 1.5 interquartile range (IQR) of the lower quartile and the highest data point still within 1.5 IQR of the upper quartile. Normal organs are ordered according to risk categories. FPKM: fragments per kilobase per million mapped reads. Normal samples: blood cells; bloodvess (blood vessels); brain; heart; liver; lung; adipose (adipose tissue); adrenal gl (adrenal gland); bile duct; bladder; bone marrow, esoph (esophagus); eye; gall bl (gallbladder); head&neck; intest. la (large intestine); intest. sm (small intestine); kidney; lymph node; nerve periph (peripheral nerve); pancreas; parathyr (parathyroid gland); petit (peritoneum); pituit (pituitary); pleura; skel. mus (skeletal muscle); skin; spleen; stomach; thyroid; trachea; ureter; breast; ovary; placenta; prostate; testis; thymus; uterus. Tumor samples: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); HCC (hepatocellular carcinoma); HNSCC (head and neck squamous cell carcinoma); MEL (melanoma); NHL (non-Hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); other (other cancers, e.g. multiple myeloma), PACA (pancreatic cancer); PRCA (prostate cancer); RCC (renal cell carcinoma); SCLC (small cell lung cancer); UBC (urinary bladder carcinoma); UEC (uterine and endometrial cancer).

Figure 2B:
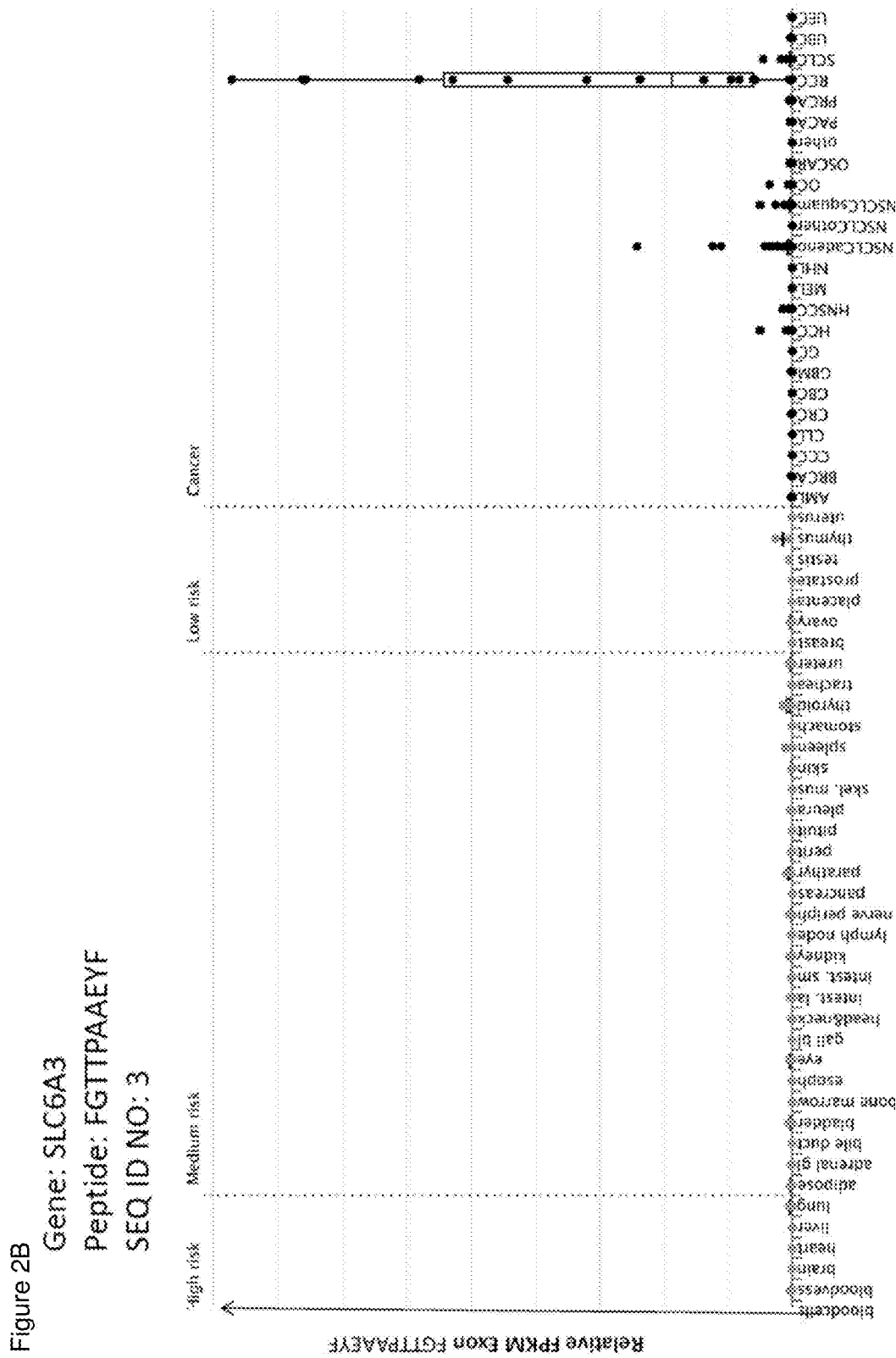
Figure 2C:
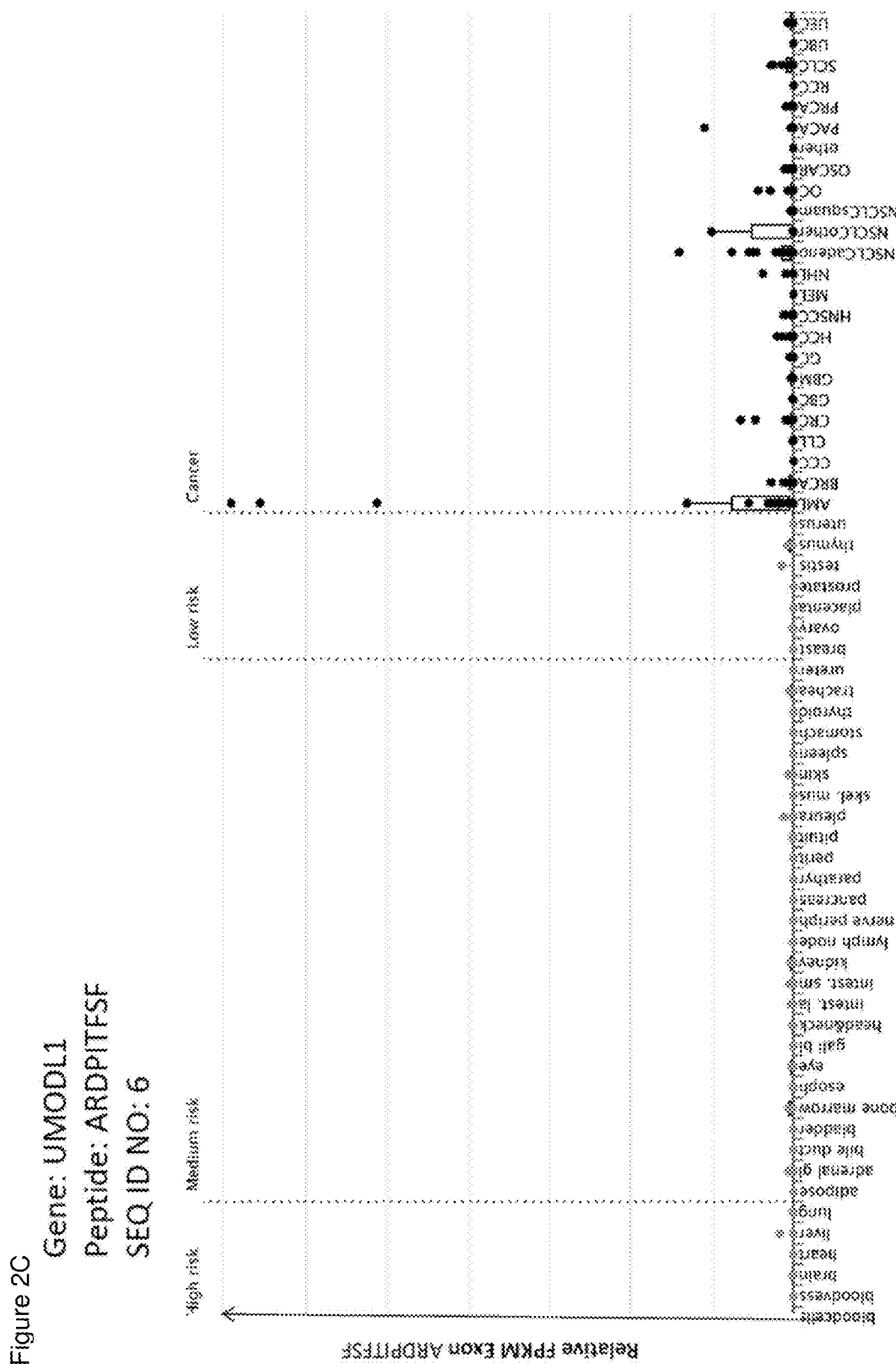
Figure 2D:
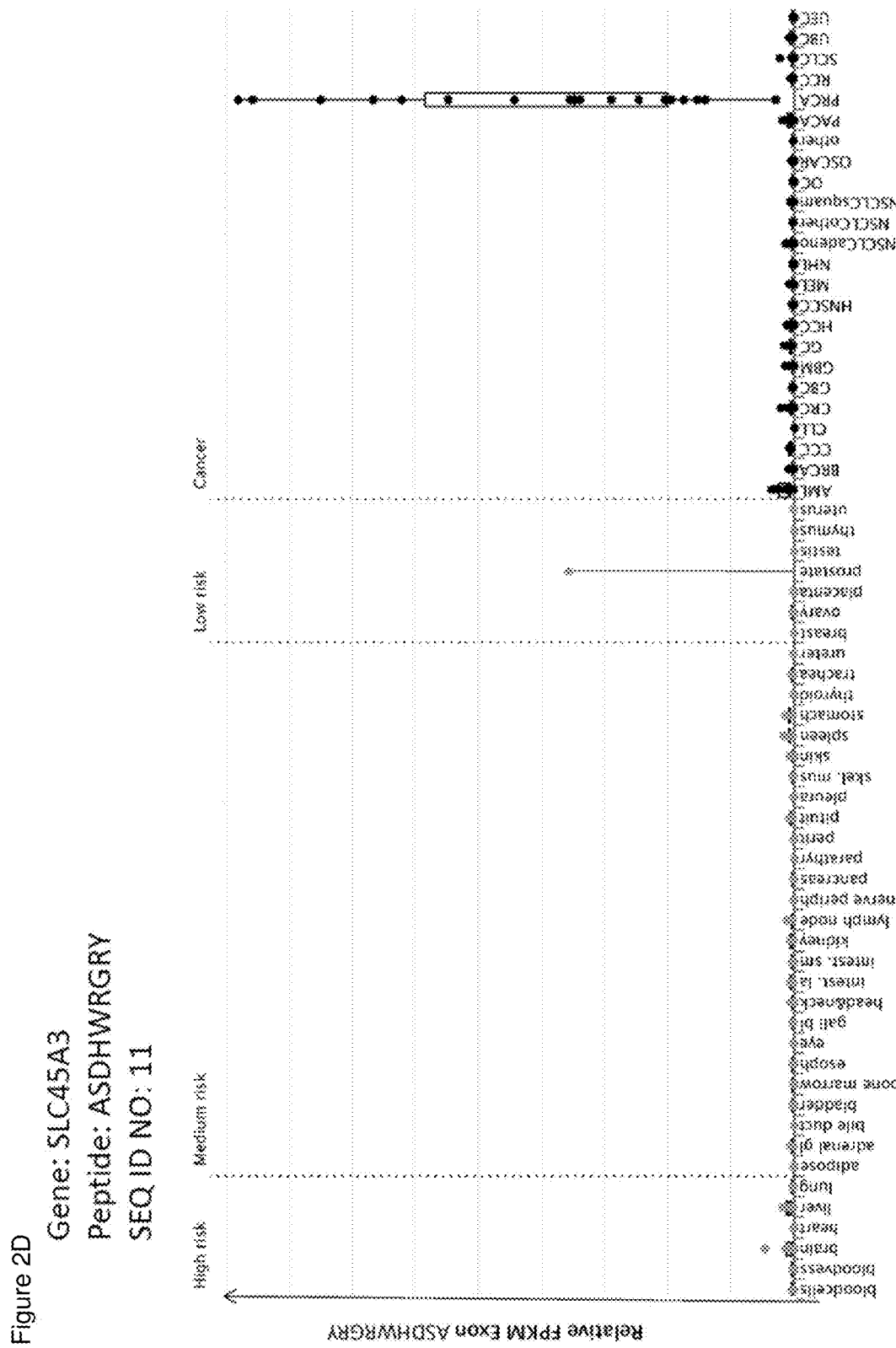
Figure 2E:
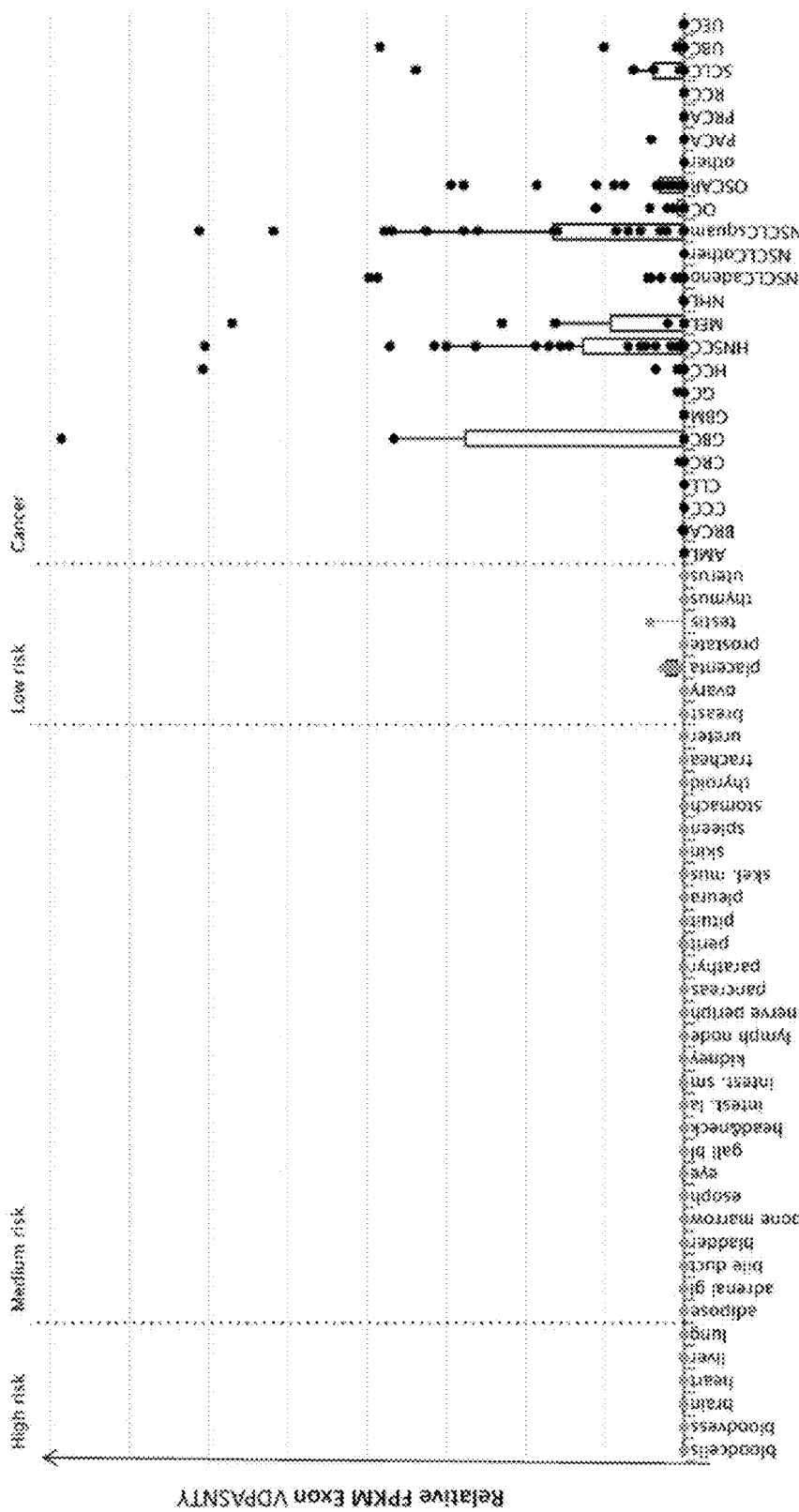
Figure 2F:
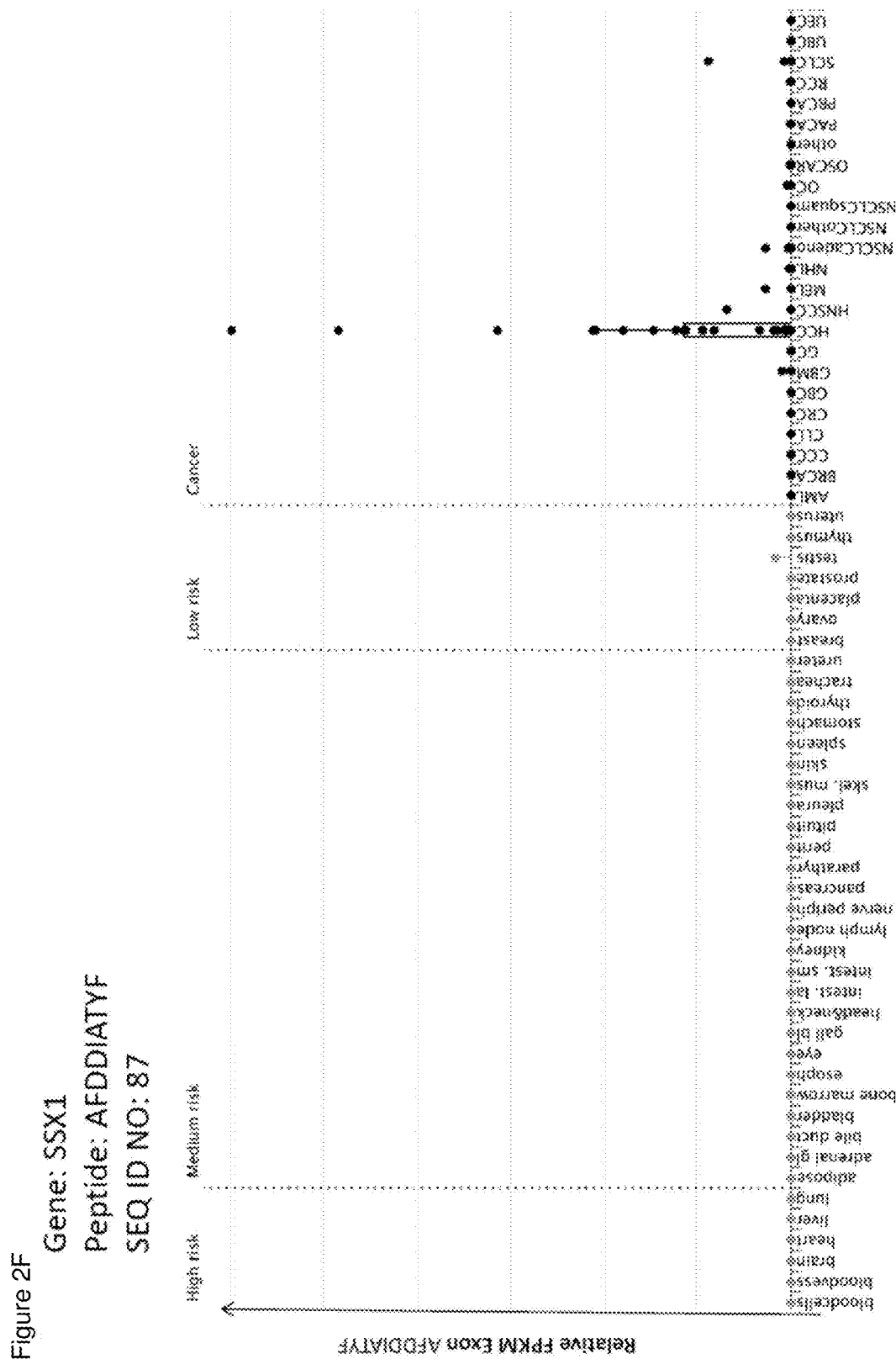
Figure 2J:
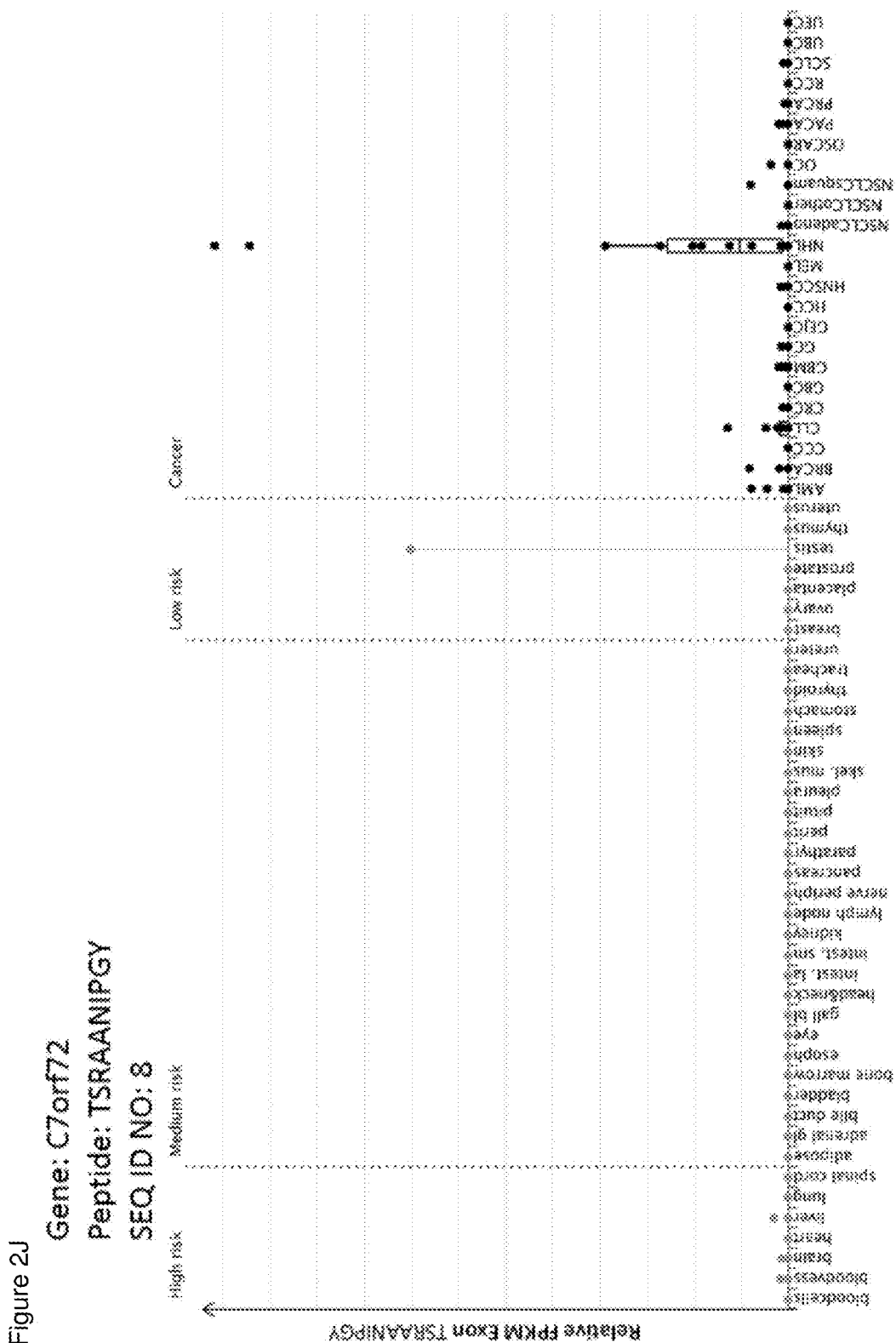
Figure 2L:
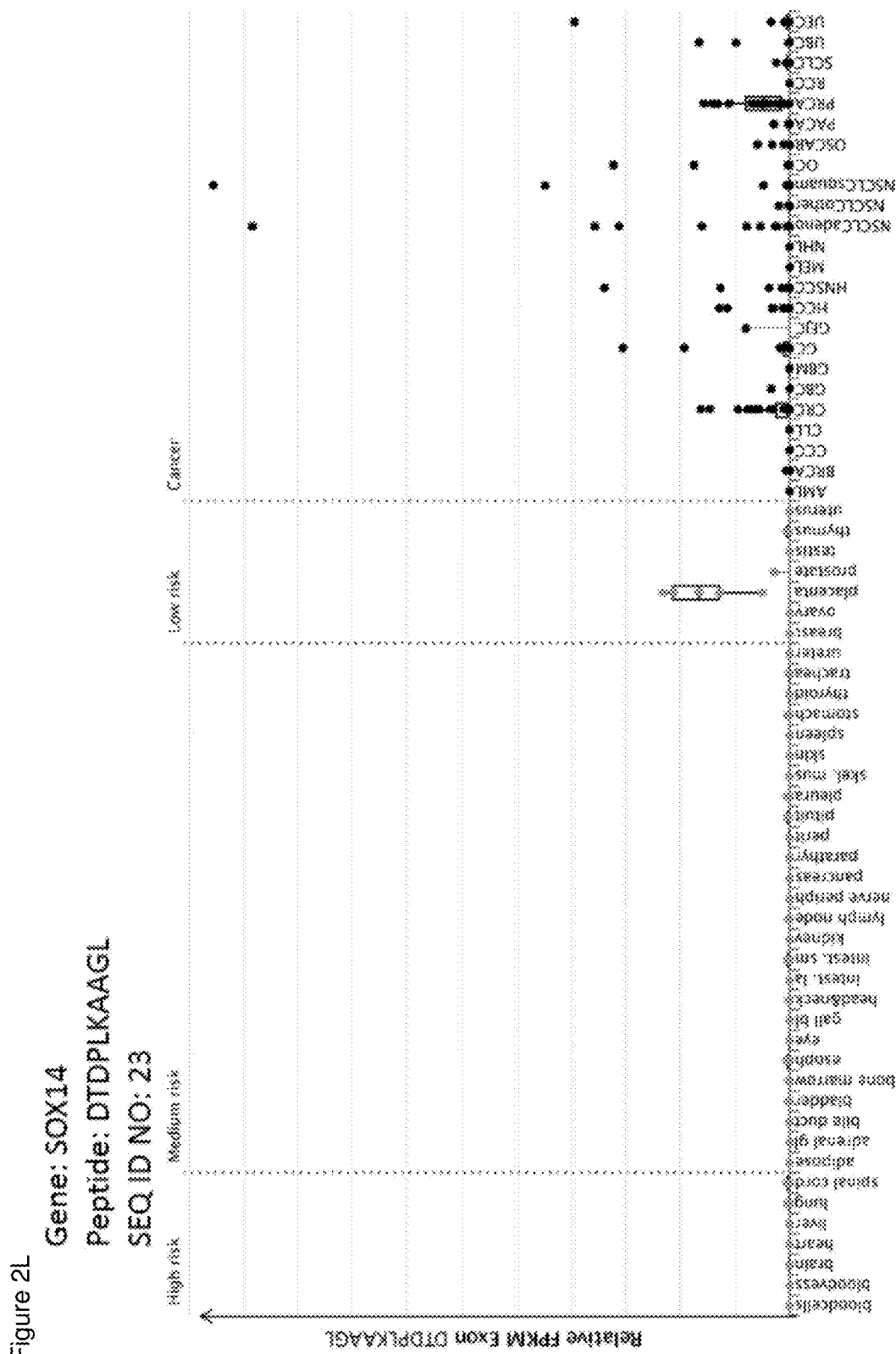
Figure 2M:
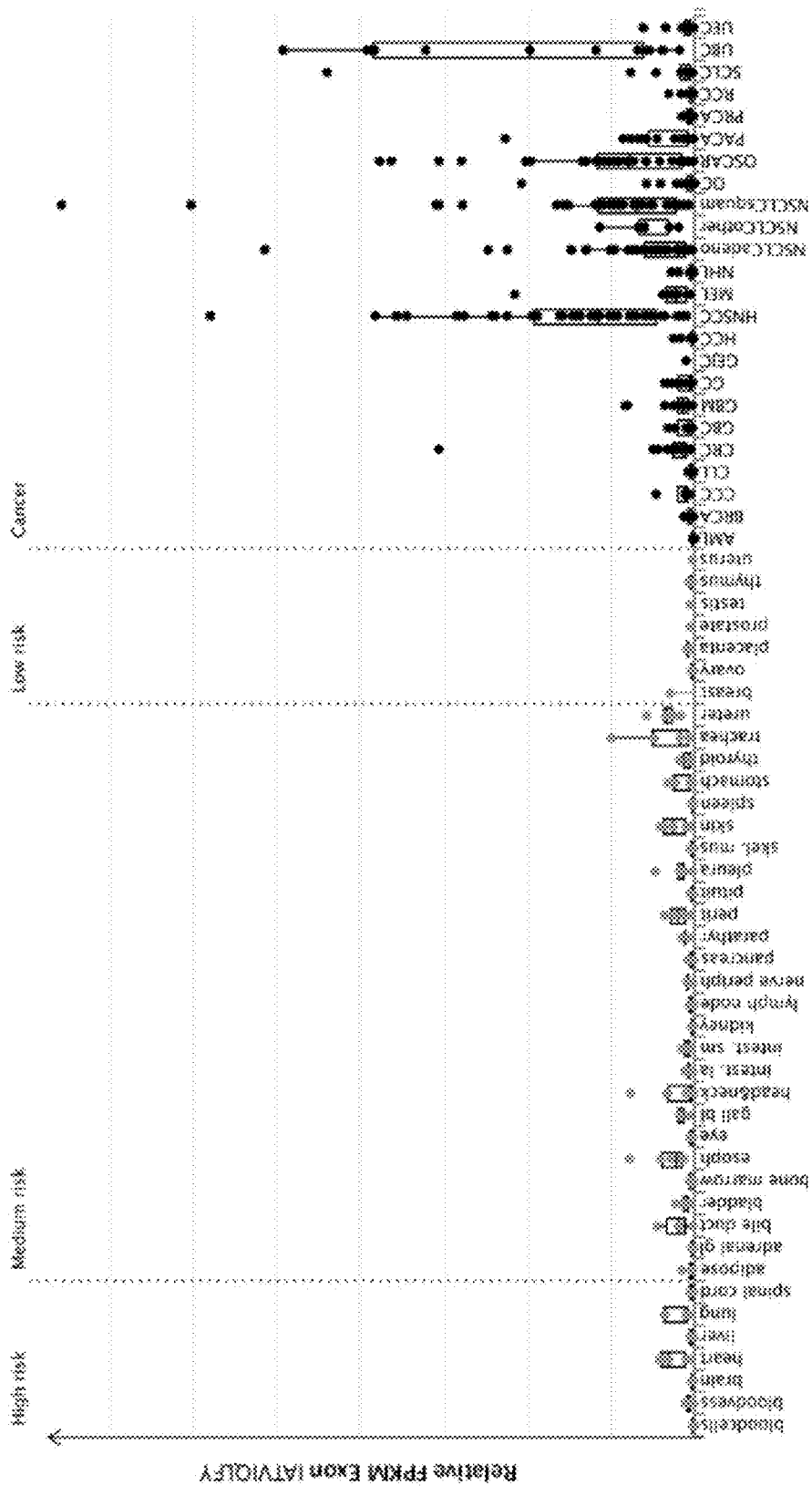

FIG. 2A) Gene symbol: MAGEA3, Peptide: VDPIGHLY (SEQ ID No.: 2), FIG. 2B) Gene symbol: SLC6A3, Peptide: FGTTPAAEYF (SEQ ID No.:3), FIG. 2C) Gene symbol: UMODL1, Peptide: ARDPITFSF (SEQ ID No.: 6), FIG. 2D) Gene symbol: SLC45A3, Peptide: ASDHWRGRY (SEQ ID No.: 11), FIG. 2E) Gene symbol: MAGEA4, Peptide: VDPASNTY (SEQ ID No.: 86), FIG. 2F) Gene symbol: SSX1, Peptide: AFDDIATYF (SEQ ID No.: 87), FIG. 2G) Gene symbol: MAGEA1, Peptide: EVYDGREHSAY (SEQ ID No.: 89), FIG. 2H) Gene symbol: MMP12, Peptide: SSDPKAVMF (SEQ ID No.: 95), FIG. 2I) Gene symbol: UMODL1, Peptide: ASDDVRIEVGLY (SEQ ID No.: 7), FIG. 2J) Gene symbol: C7orf72, Peptide: TSRAANIPGY (SEQ ID No.: 8), FIG. 2K) Gene symbol: CTCFL, Peptide: NTHTGTRPY (SEQ ID No.: 13), FIG. 2L) Gene symbol: SOX14, Peptide: DTDPLKAAGL (SEQ ID No.: 23), FIG. 2M) Gene symbol: HAS2, HAS3, Peptide: IATVIQLFY (SEQ ID No.: 66), FIG. 2N) Gene symbol: SLC6A3, Peptide: CLVLVIVLLY (SEQ ID No.: 91), FIG. 2O) Gene symbol: UMODL1, Peptide: TATLLIVRY (SEQ ID No.: 96), and FIG. 2P) Gene symbol: CDK6, Peptide: LTSVVVTLW (SEQ ID No.: 374).

Figure 3A:
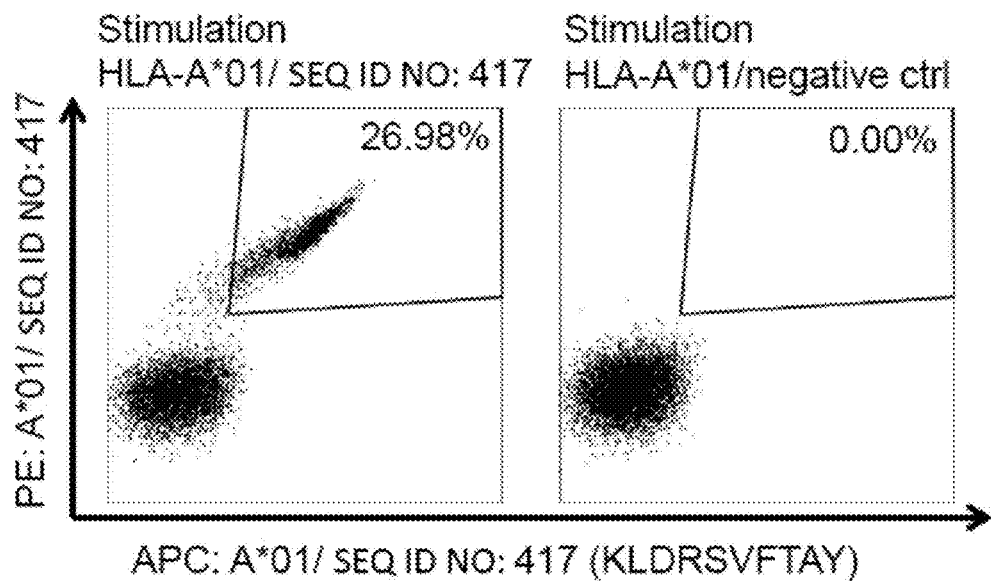
Figure 3B:
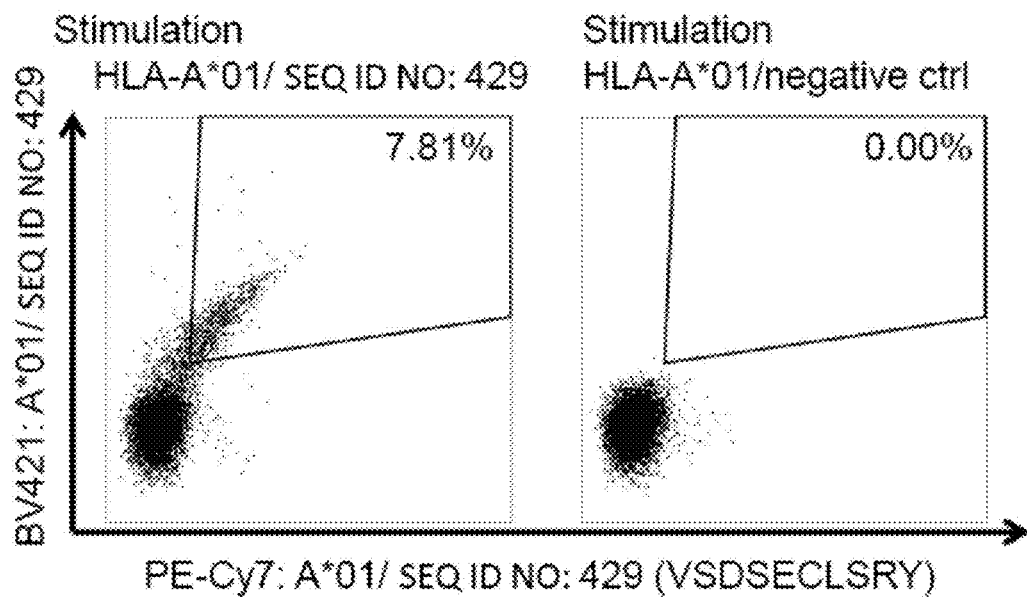
Figure 3C:
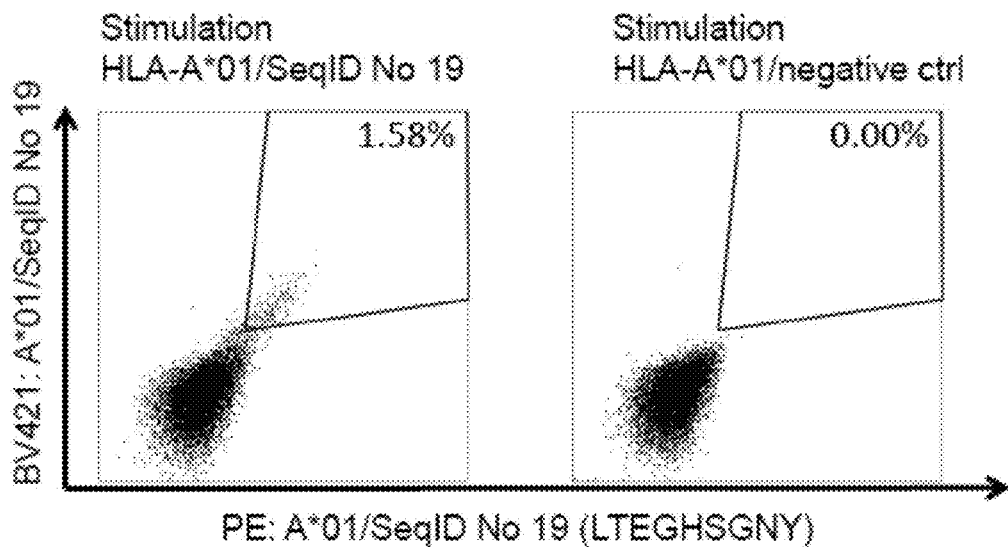
Figure 3D:
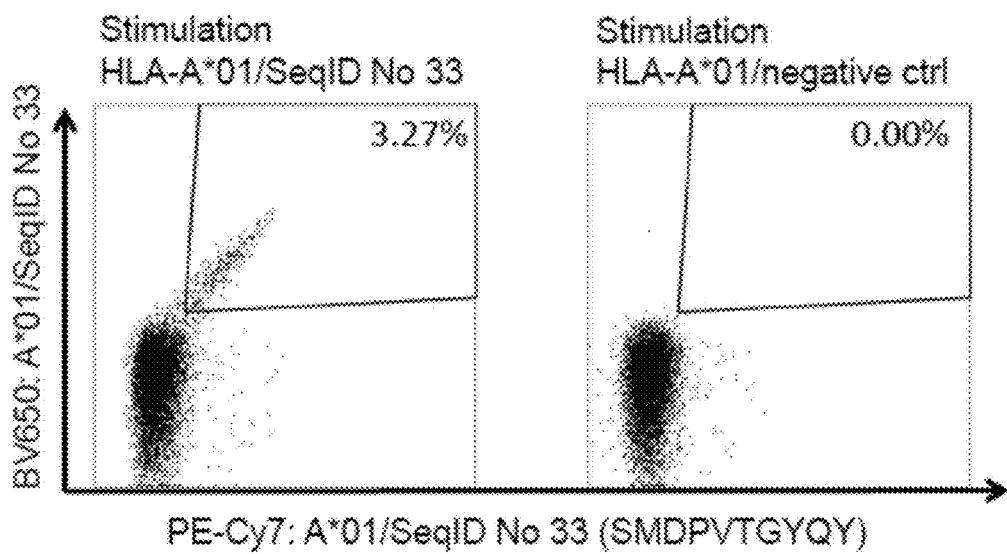
Figure 3E:
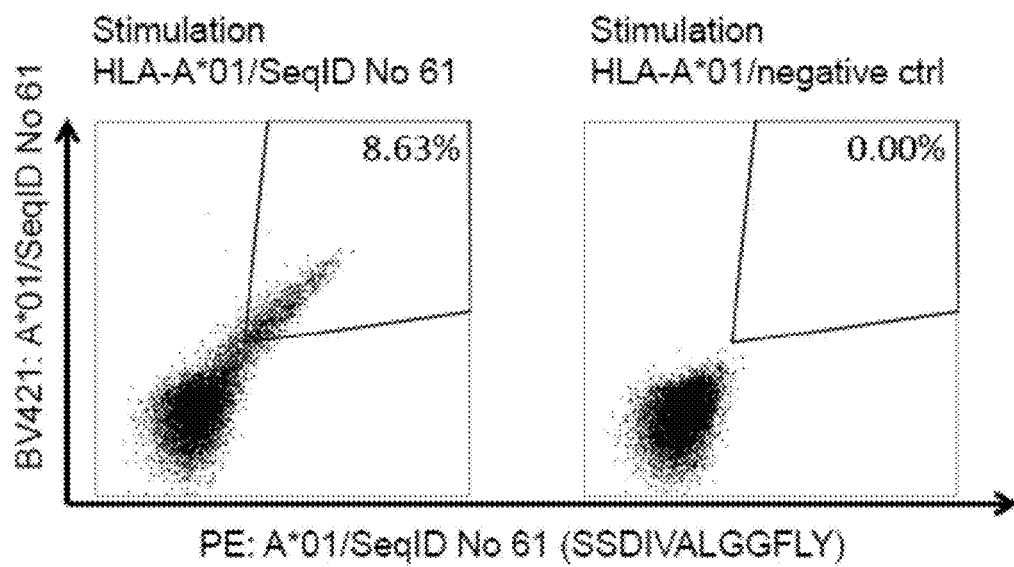
Figure 3F:
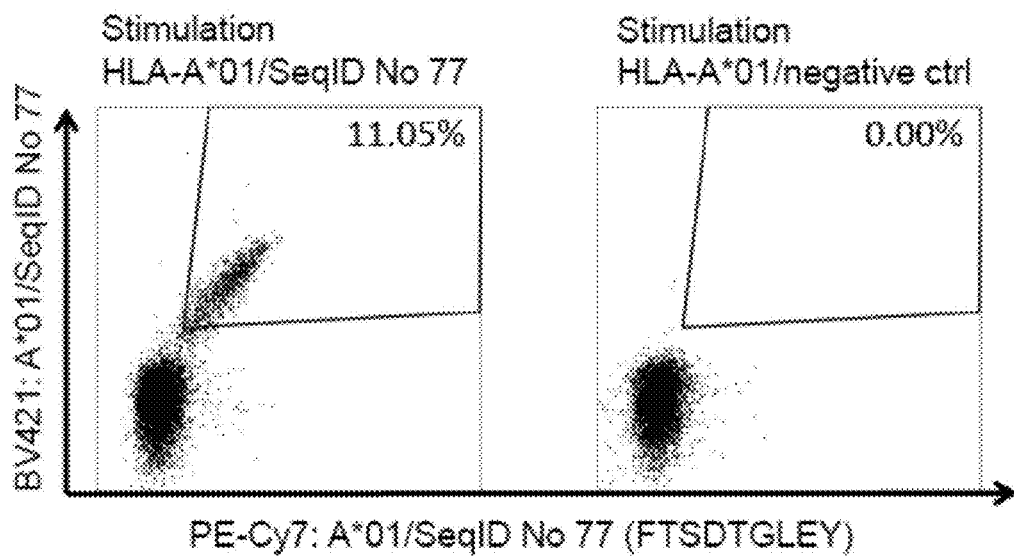
Figure 3G:
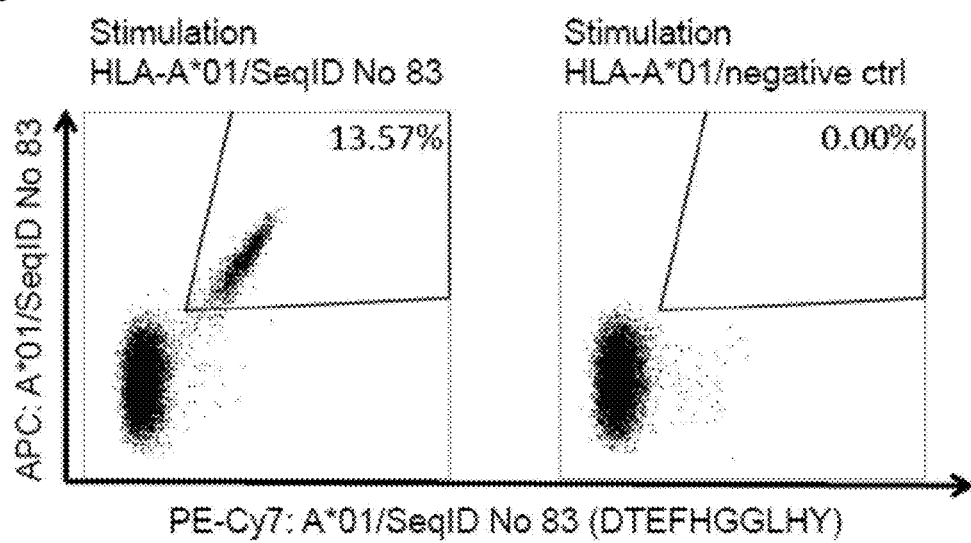

FIGS. 3A through 3G show exemplary results of peptide-specific in vitro CD8+ T cell responses of a healthy HLA-A*01+ donor. CD8+ T cells were primed using artificial APCs coated with anti-CD28 mAb and HLA-A*01 in complex with SeqID No 417 peptide (KLDRSVFTAY) (FIG. 3A, left panel), Seq ID NO: 429 peptide (VSDSECLSRY) (FIG. 3B, left panel), Seq ID NO: 19 peptide (LTEGHSGNY) (FIG. 3C, left panel), Seq ID NO: 33 peptide (SMDPVTGYQY) (FIG. 3D, left panel), Seq ID NO: 61 peptide (SSDIVALGGFLY) (FIG. 3E, left panel), Seq ID NO: 77 peptide (FTSDTGLEY) (FIG. 3F, left panel), or Seq ID NO: 83 peptide (DTEFHGGLHY) (FIG. 3G, left panel). After three cycles of stimulation, the detection of peptide-reactive cells was performed by 2D multimer staining with A*01/SeqID No 417 (FIG. 3A), or A*01/SeqID No 429 (FIG. 3B), A*01/SeqID No 19 (FIG. 3C), A*01/SeqID No 33 (FIG. 3D), A*01/SeqID No 61 (FIG. 3E), A*01/SeqID No 77 (FIG. 3F), or A*01/SeqID No 83 (FIG. 3G). Right panels show control staining of cells stimulated with irrelevant A*01/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Identification and Quantitation of Tumor Associated Peptides Presented on the Cell Surface Tissue Samples Patients' tumor tissues were obtained from: Asterand (Detroit, Mich., USA & Royston, Herts, UK), Bio-Options Inc. (Brea, Calif., USA), BioServe (Beltsville, Md., USA), Geneticist Inc. (Glendale, Calif., USA), Leiden University Medical Center (LUMC) (Leiden, Netherlands), ProteoGenex Inc. (Culver City, Calif., USA); Saint Savas Hospital (Athens, Greece), Tissue Solutions Ltd (Glasgow, UK), University Hospital Bonn (Bonn, Germany), University Hospital Geneva (Geneva, Switzerland), University Hospital Heidelberg (Heidelberg, Germany), Osaka City University (OCU) (Osaka, Japan), University Hospital Tübingen (Tübingen, Germany). Normal tissues were obtained from Asterand (Detroit, Mich., USA & Royston, Herts, UK), BioServe (Beltsville, Md., USA), Capital BioScience Inc. (Rockville, Md., USA), Centre for Clinical Transfusion Medicine Tuebingen (Tübingen, Germany), Geneticist Inc. (Glendale, Calif., USA), ProteoGenex Inc. (Culver City, Calif., USA), Tissue Solutions Ltd (Glasgow, UK), University Hospital Heidelberg (Heidelberg, Germany), University Hospital Tübingen (Tübingen, Germany).

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol(Falk et al., 1991; Seeger et al., 1999) using the HLA-A*02-specific antibody BB7.2, the HLA-A, —B, C-specific antibody W6/32, the HLA-DR specific antibody L243 and the HLA DP specific antibody B7/21, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.×

250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST at a fixed false discovery rate (q0.05) and additional manual control. In cases where the identified peptide sequence was uncertain it was additionally validated by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus, each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer samples to a baseline of normal tissue samples.

Figure 1A:
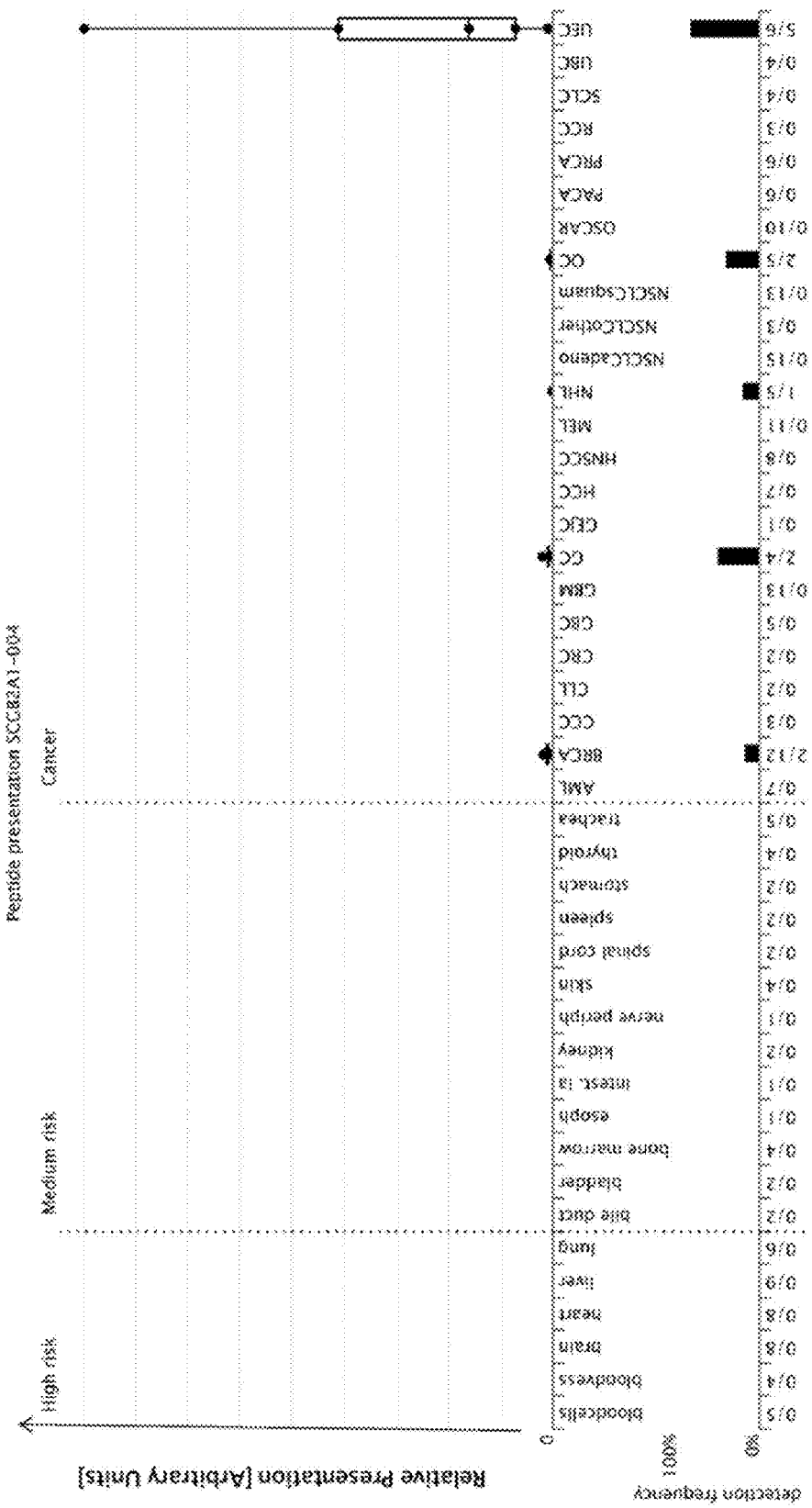
FIGS. 1A through 1N show the over-presentation of various peptides in different cancer tissues (black dots). Upper part: Median MS signal intensities from technical replicate measurements are plotted as dots for single HLA-A*01 positive normal (grey dots, left part of figure) and tumor samples (black dots, right part of figure) on which the peptide was detected. Boxes display median, 25th and 75th percentile of normalized signal intensities, while whiskers extend to the lowest data point still within 1.5 interquartile range (IQR) of the lower quartile, and the highest data point still within 1.5 IQR of the upper quartile. Normal organs are ordered according to risk categories (blood cells, blood vessels, brain, liver, lung: high risk, grey dots; reproductive organs, breast, prostate: low risk, grey dots; all other organs: medium risk; grey dots). Lower part: The relative peptide detection frequency in every organ is shown as spine plot. Numbers below the panel indicate number of samples on which the peptide was detected out of the total number of samples analyzed for each organ (N=72 for normal samples, N=155 for tumor samples). If the peptide has been detected on a sample but could not be quantified for technical reasons, the sample is included in this representation of detection frequency, but no dot is shown in the upper part of the figure. Tissues (from left to right): Normal samples: blood cells; bloodvess (blood vessels); brain; heart; liver; lung; bile duct; bladder; bone marrow; esoph (esophagus); intest. la (large intestine); kidney; nerve periph (peripheral nerve); skin; spinal cord; spleen; stomach; thyroid; trachea. Tumor samples: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine and endometrial cancer).
Figure 1C:
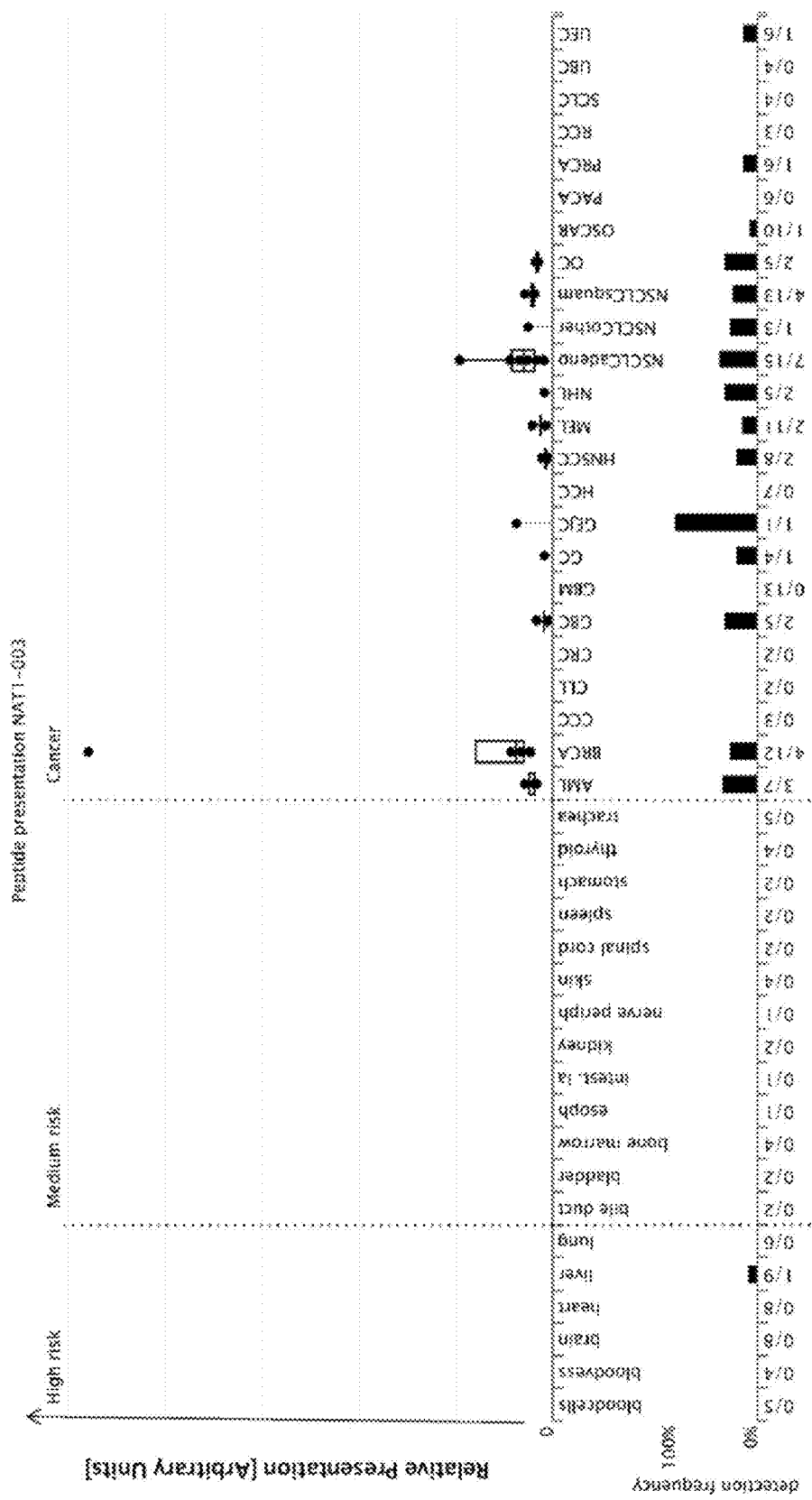
Figure 1E:
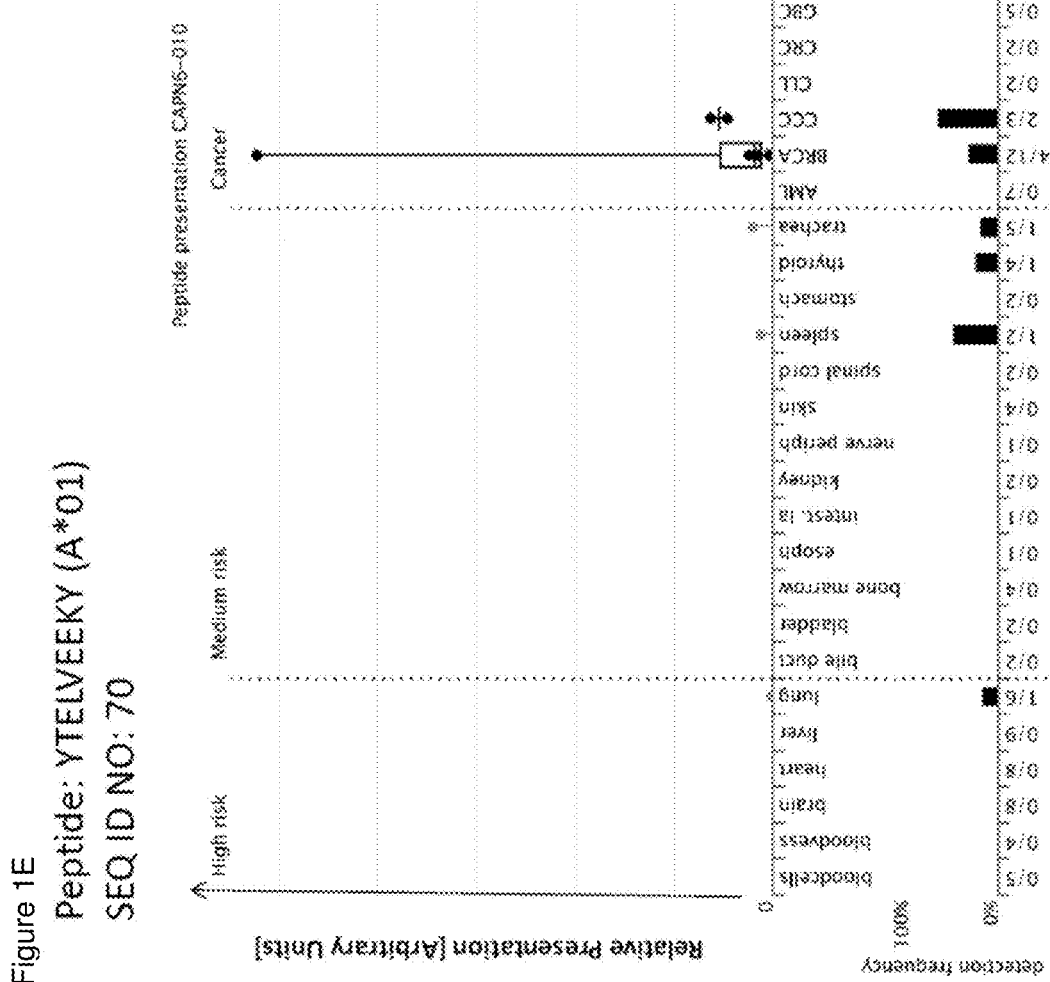
Figure 1F:
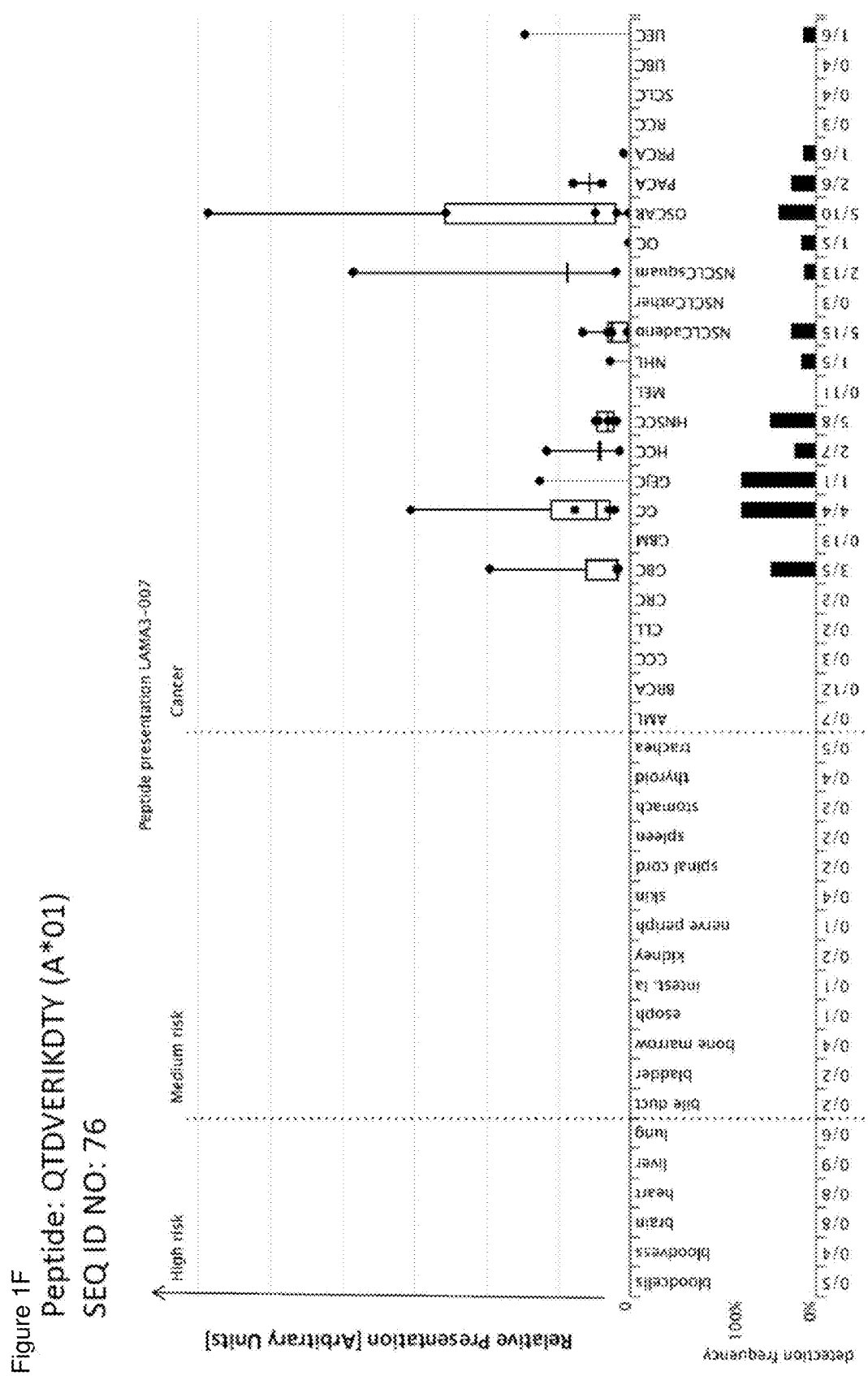
Figure 1G:
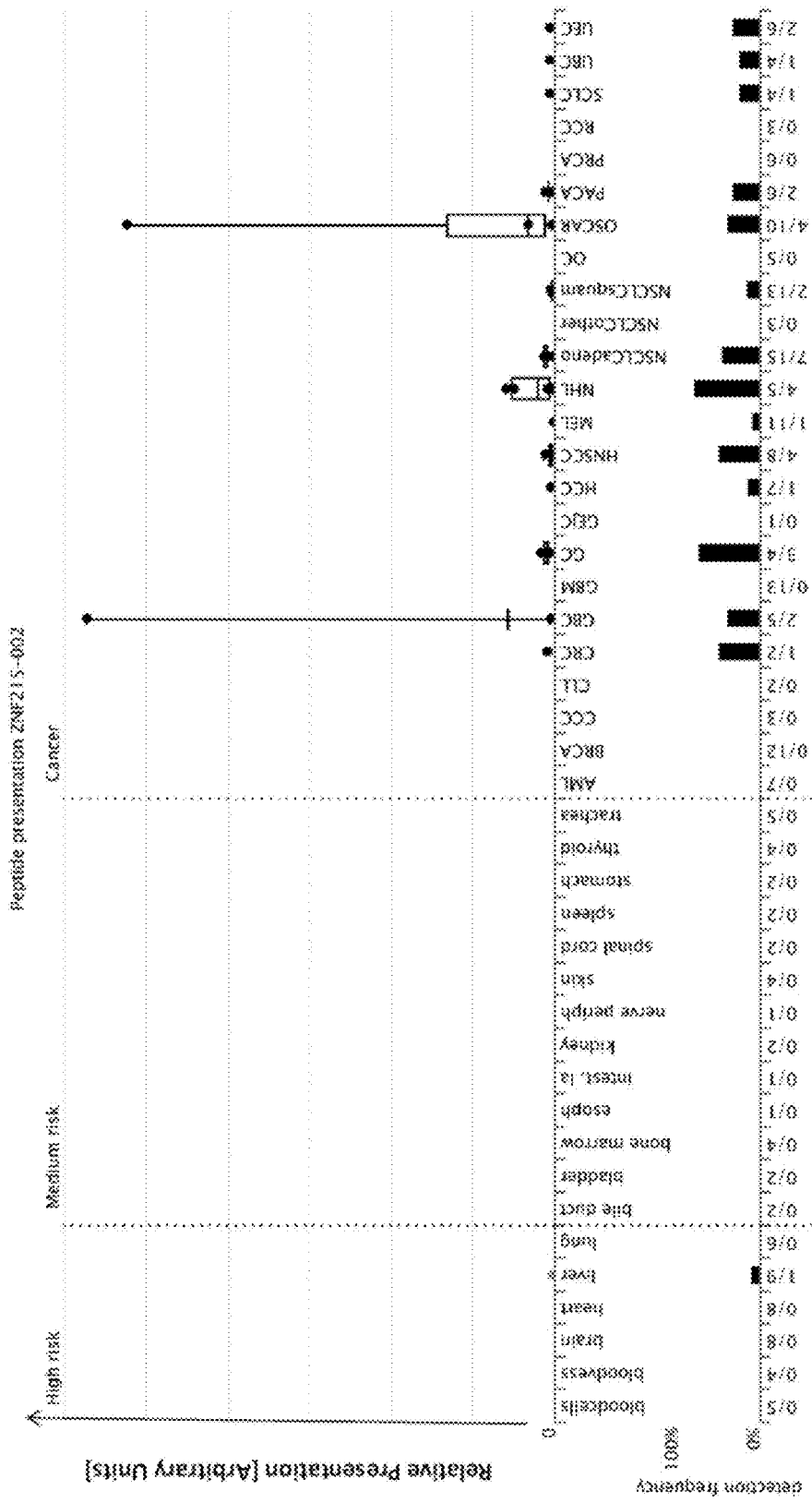
Figure 1H:
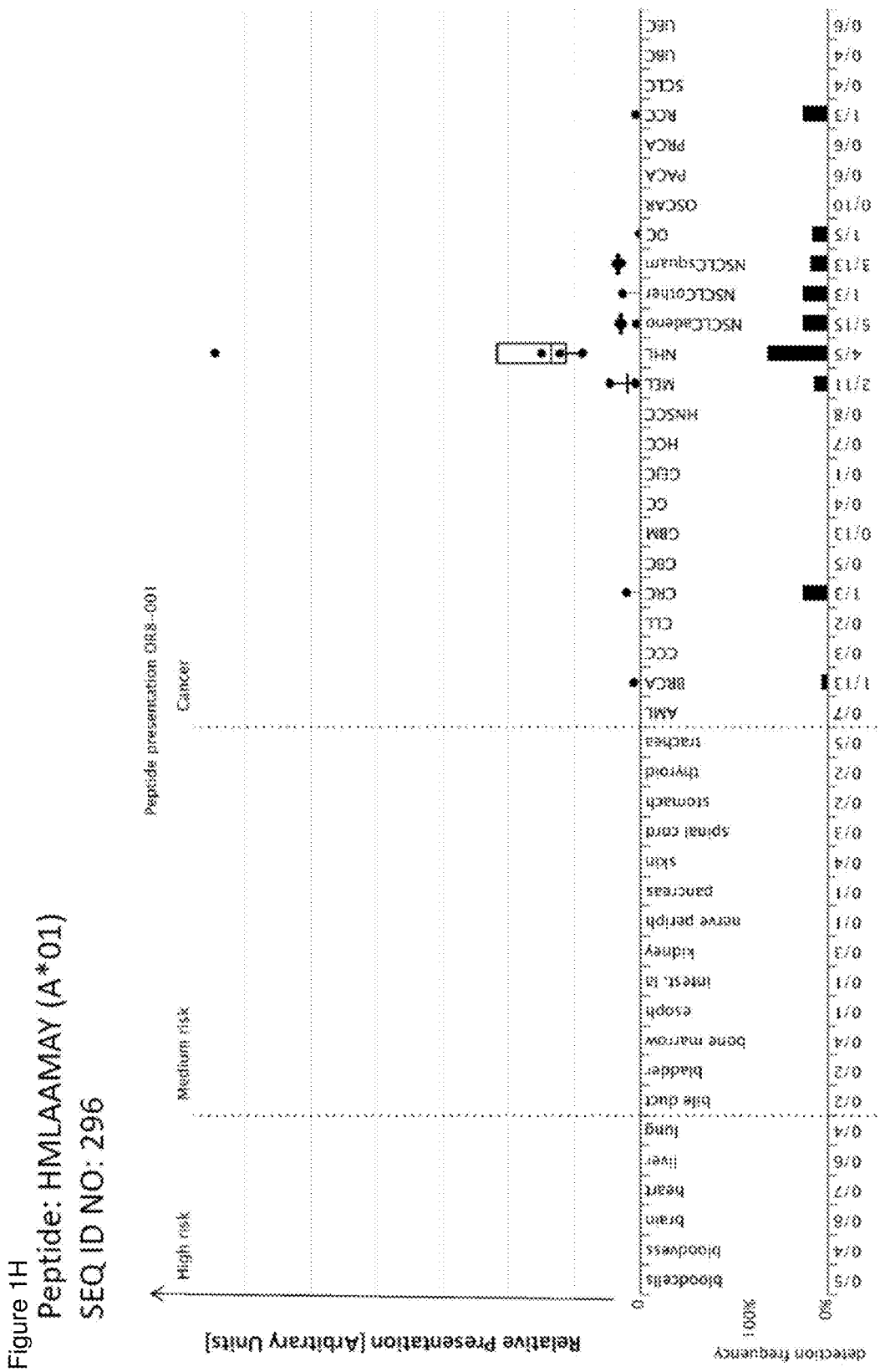
Figure 1J:
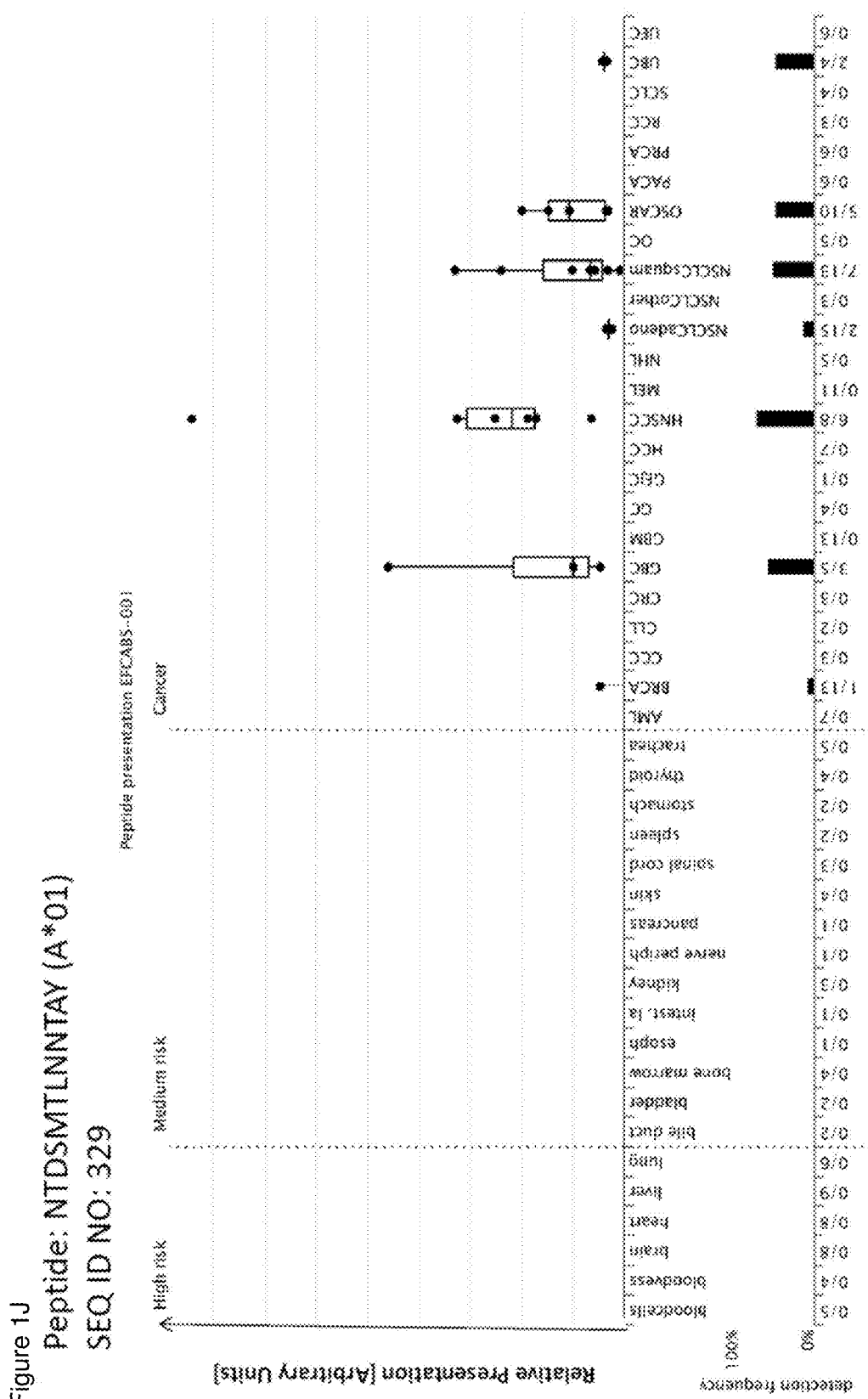
Figure 1N:
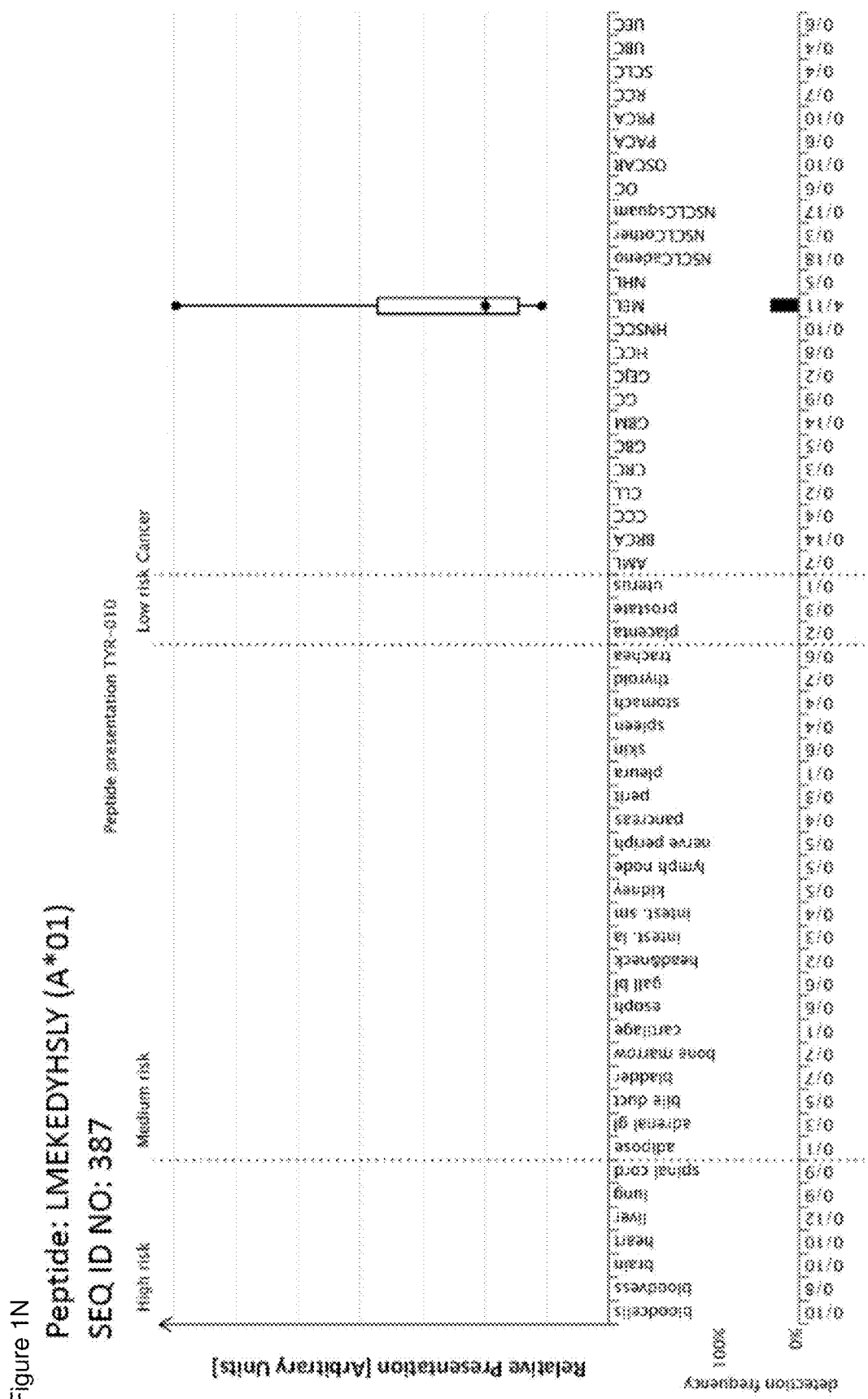

Presentation profiles of exemplary over-presented peptides are shown in FIGS. 1A-1N.

Table 8 shows the presentation on various cancer entities for selected peptides, and thus the particular relevance of the peptides as mentioned for the diagnosis and/or treatment of the cancers as indicated (e.g. peptide SEQ ID No. 21 for breast cancer and prostate cancer, peptide SEQ ID No. 47 for melanoma, non-small cell lung cancer, and ovarian cancer).

TABLE 8

Overview of presentation of selected tumor-associated peptides of the present invention across entities.

| SEQ ID No. | Sequence | Peptide Presentation on cancer entities |
|---|---|---|
| 1 | TLDSTRTLY | PRCA |
| 2 | VDPIGHLY | HCC |
| 3 | FGTTPAAEYF | OSCAR |
| 4 | RIEAIRAEY | MEL |
| 5 | FMVIAGMPLFY | NSCLCsquam |
| 6 | ARDPITFSF | HNSCC, NSCLCadeno |
| 7 | ASDDVRIEVGLY | AML, NSCLCother |
| 8 | TSRAANIPGY | MEL |
| 9 | QLDSTLDSY | BRCA |
| 10 | VSERTGISY | MEL |
| 11 | ASDHWRGRY | PRCA |
| 12 | YTDFVGEGLY | BRCA, PRCA |
| 13 | NTHTGTRPY | NSCLCsquam |
| 14 | QSEKEPGQQY | HCC |
| 15 | YLDSSKPAVY | BRCA, UEC |
| 16 | NSDISIPEY | BRCA, GC, NHL, OC, SCLC, UEC |
| 17 | ASWAVLCYY | NSCLCsquam |
| 18 | RSDPVSLRY | GBM |
| 19 | LTEGHSGNY | NHL |
| 20 | LSAQHRMLA | GBM |
| 21 | LSSAVNPIIY | MEL |
| 22 | VMDTLGLFY | BRCA, MEL, PRCA |
| 23 | DTDPLKAAGL | GBC, GBM, GC, MEL, NSCLCadeno, NSCLCsquam, OC, OSCAR, UEC |
| 24 | NLDHYTNAY | UEC |
| 25 | AMMQEAQLAY | NSCLCadeno, NSCLCother, SCLC, UEC |
| 26 | ASDDFRSKY | OSCAR |
| 27 | PSEVPVDSHY | GBM, MEL |
| 28 | PSEVPVDSHYY | CCC, HCC, HNSCC, MEL, NSCLCadeno, NSCLCother, OC |
| 29 | TLEDLDNLYNY | NSCLCadeno |
| 30 | VTTDKPRAY | HNSCC |
| 31 | VSDHLQAGMLGQY | HNSCC, OSCAR |
| 32 | GTDKQNSTLRY | MEL, NSCLCadeno |
| 33 | SMDPVTGYQY | MEL |

TABLE 8-continued

Overview of presentation of selected tumor-associated peptides of the present invention across entities.

| SEQ ID No. | Sequence | Peptide Presentation on cancer entities |
|---|---|---|
| 34 | SSWSAGENDSY | BRCA, CCC, GBC, GBM, GC, HNSCC, MEL, NSCLCsquam, OC, OSCAR, PACA, UEC |
| 35 | SWSAGENDSYS | BRCA, NSCLCadeno, NSCLCsquam, UEC |
| 36 | MTSTEQSLY | HCC, MEL |
| 37 | MTSTEQSLYY | MEL |
| 38 | KSWSQSSSLMY | HCC, HNSCC, MEL |
| 39 | WSQSSSLMY | AML, GBC, GC, HCC, NSCLCsquam |
| 40 | TSDQLGYSY | MEL |
| 41 | HSDLLEDSKY | AML, BRCA, CLL, GBC, GC, HCC, HNSCC, MEL, NHL, NSCLCadeno, NSCLCother, NSCLCsquam, OC, OSCAR, PACA, PRCA, SCLC, UBC, UEC |
| 42 | ASDVDTLLK | GBM |
| 43 | ETEPERHLGSY | PRCA |
| 44 | IPSFNEMVY | GBM, NSCLCadeno, NSCLCsquam |
| 45 | NLDPNKIY | MEL, OSCAR |
| 46 | RSDPGGGLAYAAY | AML, BRCA |
| 47 | WSDGVPLLY | GBM, MEL |
| 50 | ITDEDEDMLSY | HCC |
| 53 | YLEDRPLSQLY | MEL, OC |
| 54 | EVDIHTIHY | GBC, HNSCC, OSCAR |
| 55 | ATEGDVLNY | MEL, NHL, NSCLCsquam |
| 56 | VTEYAEEIYQY | AML |
| 57 | ASDPASSTSCY | HCC |
| 58 | YLENSASWY | UEC |
| 59 | FTDSQGNDIK | MEL |
| 60 | MTEKFLFLY | HNSCC, OSCAR |
| 61 | SSDIVALGGFLY | AML, BRCA, NSCLCsquam |
| 62 | VSELVTTGHY | AML, CRC, GBC, GBM, NSCLCadeno, NSCLCsquam, OC, OSCAR |
| 63 | TSEISQNALMY | NSCLCadeno, NSCLCother, NSCLCsquam |
| 64 | TSEISQNALMYY | NSCLCadeno |
| 65 | SSDFDPLVY | BRCA, GBC, GBM, GC, HCC, MEL, NSCLCadeno, NSCLCsquam, UEC |
| 67 | NVDQNQNSY | GBM, HNSCC, MEL, NSCLCadeno |
| 68 | QSLPEFGLTY | CCC, OSCAR |
| 69 | QSLPEFGLTYY | OSCAR |
| 70 | YTELVEEKY | BRCA, CCC, CRC, GC, HCC, HNSCC, MEL, NHL, NSCLCadeno, NSCLCother, NSCLCsquam, OC, OSCAR, PACA, PRCA, RCC, UEC |
| 71 | LTDSTTRTTY | CRC, GC, NSCLCadeno, NSCLCsquam, PACA |
| 72 | VTDSTTKIAY | GC, NSCLCsquam, PACA, SCLC |
| 73 | STDSASYY | HCC |
| 74 | EMEQQSQEY | HNSCC, OSCAR |
| 75 | FTDYELKAY | HCC |
| 76 | QTDVERIKDTY | CCC, CRC, GBC, GC, HCC, HNSCC, NHL, NSCLCadeno, NSCLCother, NSCLCsquam, OC, OSCAR, PACA, PRCA, UEC |
| 77 | FTSDTGLEY | AML, NSCLCadeno |
| 78 | QLDSAVKNLY | BRCA, CRC, GBC, GC, HCC, HNSCC, MEL, NHL, NSCLCadeno, NSCLCsquam, OSCAR, PACA, SCLC, UBC, UEC |
| 79 | ASDLEPRELLSY | BRCA |
| 80 | ELCPLPGTSAY | GBC, GBM, GC, HCC, HNSCC |
| 81 | YSDLHTPGRY | AML, SCLC |
| 82 | LTEKSHIRY | BRCA, GBM, MEL, NSCLCadeno, NSCLCsquam |
| 83 | DTEFHGGLHY | BRCA, GC, OSCAR, PACA |
| 84 | ESEMIKFASYY | HCC |
| 85 | SSDNYEHWLY | BRCA, MEL, NSCLCadeno |
| 87 | AFDDIATYF | SCLC |
| 88 | KEVDPAGHSYI | NHL |
| 89 | EVYDGREHSAY | MEL, OSCAR |
| 90 | YEDHFPLLF | MEL, OSCAR |
| 91 | CLVLVIVLLY | NSCLCadeno |
| 92 | TTDDTTAMASAS | GBC, MEL, NSCLCsquam |
| 93 | HLKILSPIY | BRCA |
| 95 | SSDPKAVMF | CRC |
| 96 | TATLLIVRY | AML |
| 97 | FPAPPAHWFY | BRCA |
| 98 | NFSDLVFTY | BRCA |

TABLE 8-continued

Overview of presentation of selected tumor-associated peptides of the present invention across entities.

| SEQ ID No. | Sequence | Peptide Presentation on cancer entities |
|---|---|---|
| 99 | AADSNPSEL | PRCA |
| 100 | TTSSAISWILY | BRCA |
| 101 | SITDVDFIY | UEC |
| 102 | STIRGELFF | BRCA |
| 103 | ITDTLIHLM | BRCA |
| 104 | ITDTLIHL | BRCA |
| 107 | TTENSGNYY | CLL |
| 108 | NSNLKFLEV | SCLC |
| 109 | ISEDKSISF | CRC |
| 111 | TPIPFDKILY | OSCAR |
| 112 | KASSVSAEDGY | GBM, UEC |
| 113 | ASCRSSAEY | OC |
| 114 | AVAAAAGASLY | AML, MEL, OSCAR |
| 115 | NEIDIHSIYFY | OSCAR |
| 116 | RSDIGEFEW | AML |
| 117 | SPAKQFNIY | GBC |
| 119 | TVFDENLSRY | OSCAR |
| 120 | LVDENQSWY | NHL |
| 121 | SADEAHGLL | MEL |
| 122 | ISEAPLTEV | MEL |
| 123 | LLKAKDILY | HNSCC |
| 124 | FLKVTGYDKDDY | HCC |
| 125 | FQYELRELY | OC |
| 126 | TTDPKKFQY | MEL, NSCLCsquam, OC |
| 127 | VPFNLITEY | MEL |
| 128 | YTEFVDATFTK | HNSCC |
| 130 | YIGLKGLYF | MEL |
| 131 | LEDGIEQSAY | NHL |
| 132 | RTHIGYKVY | NSCLCsquam |
| 134 | SAPSSSGSPLY | NSCLCsquam |
| 135 | TFDKQIVLL | NSCLCother |
| 136 | RRLNFSGFGY | SCLC |
| 137 | EAYLERIGY | BRCA |
| 138 | IPVHDSVGVTY | MEL |
| 139 | PVHDSVGVTY | GC, SCLC, UEC |
| 140 | SQHIFTVSY | GBM, NSCLCsquam |
| 141 | DAVAPGREY | GBC |
| 142 | IEKFAVLY | HNSCC |
| 143 | HVSGQMLYF | BRCA |
| 144 | RTIEGDFLW | GBM |
| 145 | LSDAVHVEF | CLL |
| 146 | LCATVCGTEQY | HNSCC |
| 147 | AQVQDTGRY | MEL |
| 148 | GTKQWVHARY | CLL |
| 149 | PIMSSSQALY | NSCLCsquam |
| 150 | FTTLSDLQTNMA | HNSCC, MEL, NHL |
| 151 | YEVDTKLLSL | MEL |
| 155 | HTMEVTVY | MEL |
| 156 | STALSILLL | MEL |
| 157 | GLIEVVTGY | MEL, OC |
| 158 | EVTDRNMLAF | HNSCC, OC, OSCAR |
| 159 | RQAPGPARDY | NSCLCsquam |
| 160 | EVLGEEMYAY | PRCA |
| 161 | EAAPDIMHY | MEL, OSCAR |
| 162 | IADNPQLSFY | BRCA |
| 163 | KIRAEVLSHY | CLL |
| 164 | KLAGTVFQY | NSCLCsquam |
| 165 | VSVYNSYPY | BRCA |
| 166 | YHRICELLSDY | GC |
| 167 | RAVQPGETY | NSCLCother, NSCLCsquam |
| 168 | VQPGETYTY | GBC |
| 169 | TVDNANILL | UBC |
| 170 | VQIAKGMNY | NSCLCsquam |
| 171 | ITDFGLAKL | NSCLCadeno |
| 172 | FSEPFHLIV | MEL |
| 173 | QSTTGVSHY | CCC |
| 174 | TSEVEGLAFVSY | NSCLCsquam |
| 175 | GLEYEAPKLY | GBM |
| 176 | HTDLESPSAVY | HCC, UBC |
| 178 | TQRTSFQFY | NSCLCadeno, NSCLCsquam, OC |
| 179 | SSTDFTFASW | HNSCC, OC, OSCAR |
| 180 | AQISDTGRY | MEL |

TABLE 8-continued

Overview of presentation of selected tumor-associated peptides of the present invention across entities.

| SEQ ID No. | Sequence | Peptide Presentation on cancer entities |
|---|---|---|
| 181 | SVTDLIGGKW | OSCAR |
| 182 | TQPELSSRY | NSCLCadeno |
| 183 | LADTDLGMTF | OSCAR |
| 184 | KTIQEVAGY | GBM, HNSCC |
| 185 | NSDESADSEPHKY | BRCA |
| 186 | AVSSGLFFY | BRCA |
| 187 | TQKSVQVLAY | GBM |
| 189 | FRGVFVHRY | MEL |
| 190 | VSSTVHNLY | BRCA |
| 191 | FTRAFDQLRM | NSCLCadeno |
| 192 | LAFYYGMY | GC, MEL, NHL, NSCLCsquam, OC, PRCA, RCC, UEC |
| 193 | SQNGQLIHY | OC |
| 194 | CYTADNEMGY | HCC |
| 195 | YTADNEMGYY | NSCLCadeno, NSCLCother |
| 196 | RLAQYTIERY | HCC |
| 197 | NDEIDKLTGY | MEL |
| 198 | KLTDYINANY | GBM |
| 199 | LCAAVLAKY | MEL |
| 200 | SLPEFGLTY | GBM, RCC |
| 201 | SLPEFGLTYY | OSCAR |
| 202 | QTDINGGSLK | MEL |
| 203 | LSQDELSKF | NSCLCsquam |
| 204 | NVKEAPTEY | NSCLCother |
| 205 | RMQEGSEVY | MEL |
| 206 | RVFVAVTLY | OC, PRCA |
| 207 | LLEGEDAHLTQY | HNSCC |
| 208 | LLISKAEDY | MEL |
| 209 | EADPFLKYL | AML |
| 210 | LLEADPFLKY | AML |
| 211 | YLNEWGSRF | NSCLCadeno |
| 212 | MMTDLTSVY | MEL |
| 213 | VSDSTTEITY | PACA |
| 214 | VQDPSLPVY | NSCLCsquam |
| 215 | DTLEAATSLY | HCC |
| 216 | NSMLDPLVY | BRCA, HNSCC, NSCLCsquam, UBC |
| 217 | LMDEGAVLTL | HNSCC |
| 218 | FTAQLQLY | GBC |
| 219 | KTELETALYY | HCC |
| 220 | DVERIKDTY | NSCLCsquam |
| 221 | TDVERIKDTY | HCC, NSCLCsquam |
| 222 | GSPDAVVSY | NSCLCsquam |
| 223 | NAVDVVPSSF | GBC |
| 224 | RTDEGDNRVW | OSCAR |
| 226 | QITPKHNGLY | NSCLCsquam, OC |
| 228 | KSFDDIAKY | OC |
| 229 | MTDVFIDY | NSCLCsquam |
| 230 | CVIETFHKY | GBC |
| 231 | LLPLLVMAY | OC |
| 232 | RYLNIVHATQLY | CLL |
| 233 | RINSATGQY | CLL |
| 234 | YTDLTTIQV | HNSCC |
| 235 | SIEIDHTQY | CCC, MEL, NSCLCadeno |
| 236 | VLDSLLAQY | GC |
| 237 | AQEAAVFLTLY | SCLC |
| 238 | ETDWGLLKGHTY | BRCA |
| 239 | SSERGSPIEKY | OSCAR |
| 240 | EVLDSLLAQY | OSCAR |
| 241 | SLMVASLTY | OC |
| 242 | GTNLPTLLW | HCC, OSCAR |
| 243 | LTSEDTGAY | NSCLCadeno |
| 244 | VTKYIAGPY | BRCA |
| 245 | LSDNAANRY | AML |
| 246 | ARLEGEIATY | NSCLCsquam |
| 247 | SMIRVGTNY | NSCLCsquam, OC |
| 248 | VTDIDELGK | GBM |
| 249 | GVGFTELEY | GC |
| 250 | GYVCNACGLY | HNSCC |
| 251 | GIEMTYETY | GBC |
| 252 | DTTSHTYLQY | OSCAR |
| 253 | YLESHGLAY | NSCLCsquam |
| 254 | FLFNDALLY | BRCA |
| 255 | WELDSLEY | GBM |

TABLE 8-continued

Overview of presentation of selected tumor-associated peptides of the present invention across entities.

| SEQ ID No. | Sequence | Peptide Presentation on cancer entities |
|---|---|---|
| 256 | HAFESNNFIY | GBC |
| 257 | KSEMNVNMKY | BRCA, GBC, NSCLCsquam, PRCA, UEC |
| 258 | RPSSVLTIY | GBM, MEL, NSCLCsquam |
| 259 | APDEVVALL | MEL |
| 260 | KPTEDSANVY | OSCAR |
| 261 | MTEGSTVNTEY | GBC, GC |
| 263 | DCMDTEGSYM | UEC |
| 264 | YRDPVFVSL | OC |
| 266 | LTDSFLLRF | HCC |
| 267 | IVADDTVY | NSCLCadeno, NSCLCother |
| 268 | AILHHLYFY | BRCA |
| 269 | LPSPAATIWDY | GBC |
| 270 | DLKIDLAAQY | OSCAR |
| 271 | VAEPPVVCSY | HCC |
| 272 | IPQDECLRY | GBC, HNSCC |
| 273 | CGPNEINHFY | NSCLCsquam |
| 274 | YADIHGDLL | RCC |
| 275 | ESDEMENLLTY | BRCA |
| 276 | QITSFASGTSY | GC |
| 277 | LPAPGFLFY | GBC |
| 278 | AATVKSDIY | NSCLCsquam |
| 279 | LMTVLLKY | BRCA |
| 280 | TTEMVSNESVDY | GBC |
| 281 | YPDLSELLM | AML, RCC, UEC |
| 282 | QAMPSWPTAAY | NSCLCsquam |
| 283 | ETILVSSSY | NSCLCadeno |
| 284 | TCSHTFVYY | NSCLCadeno, SCLC |
| 285 | VLPHHSEGACVY | NSCLCadeno, OC |
| 286 | ATDMEGNLNY | BRCA, GBM, NSCLCadeno |
| 287 | ENSIEDLQY | HCC |
| 289 | YTSHEDIGY | NSCLCadeno |
| 290 | GQFTGTAGACRY | NSCLCadeno, OC |
| 291 | TSDVTGSLTY | BRCA, HNSCC, MEL, NHL, NSCLCadeno, NSCLCother |
| 292 | VLDFAPPGASAY | OC |
| 293 | IISVLIAIY | BRCA |
| 294 | MMEMEGMY | NSCLCsquam |
| 295 | GQRLDEAMISY | OC |
| 296 | HMLAAMAY | BRCA, MEL, NHL, NSCLCadeno, NSCLCother, NSCLCsquam, OC, RCC |
| 297 | RLDEAMISY | UBC |
| 298 | KFDVINHYF | BRCA |
| 299 | EVDSVALSL | MEL |
| 300 | VSINPNSGDIY | GC |
| 301 | ESQTCASDY | GBC, NSCLCother |
| 302 | FYLSTPENYHY | BRCA |
| 303 | GFGGLSSQGVYY | CCC, HNSCC |
| 304 | FSENLIYTYI | MEL |
| 305 | YADLLIYTY | NSCLCadeno, UBC |
| 306 | KSFETTVRY | MEL, OSCAR |
| 307 | DTDDRELRY | GBM, HCC, UEC |
| 308 | ELAAGQVVY | CLL, OSCAR |
| 309 | EVDRNLIQY | UEC |
| 311 | TVTDGTHTDFY | NSCLCsquam |
| 312 | VTDGINPLI | OSCAR |
| 313 | VTDGTHTDFY | MEL |
| 314 | PPEANSLQGALY | CCC, OC |
| 315 | VLKIELETY | GBM, GC, NSCLCadeno, NSCLCsquam, OC, PACA, PRCA, RCC |
| 316 | YTCEECGQAF | BRCA, GBM, GC, HCC, HNSCC, NHL, NSCLCadeno, NSCLCsquam, OSCAR, PACA, UEC |
| 317 | EDLLEVLDMY | UEC |
| 318 | YMTSMALNY | NSCLCsquam |
| 319 | FTDPHIITF | BRCA |
| 320 | QALQDKLQTFY | BRCA |
| 321 | DGIADASNLSYY | MEL, NSCLCadeno, NSCLCsquam |
| 322 | FSELNPLALY | GC, HNSCC, NSCLCsquam, OSCAR |
| 323 | KTLQKPVLPLY | CLL |
| 324 | RTGIFPYRF | GBC |
| 325 | LQKPVLPLY | CLL, NSCLCsquam |
| 326 | STSRLTLFS | GBM, HNSCC |
| 327 | IMLSVDQHLY | HNSCC, MEL |

TABLE 8-continued

Overview of presentation of selected tumor-associated peptides of the present invention across entities.

| SEQ ID No. | Sequence | Peptide Presentation on cancer entities |
|---|---|---|
| 328 | LLDEDNNIKL | GBC |
| 329 | NTDSMTLNNTAY | BRCA, GBC, HNSCC, NSCLCadeno, NSCLCsquam, OSCAR, UBC |
| 331 | YLYQAPGSLALY | NSCLCadeno |
| 332 | SLISFKYTSY | OC |
| 333 | LSDPQAELQFY | GBM |
| 334 | PSSMPECLSY | NSCLCsquam |
| 335 | PSSMPECLSYY | NSCLCadeno |
| 336 | ATNIQLNIDTY | OC |
| 337 | FTESNQYNIY | BRCA, MEL, NSCLCadeno, NSCLCsquam |
| 338 | YSPDSFNVSW | OSCAR |
| 339 | ESMDIFPLGW | HNSCC, OC, OSCAR |
| 340 | SVDSNLVAY | NSCLCadeno |
| 341 | PANYLGKMTY | MEL, NSCLCadeno, OC, PRCA |
| 343 | YFGNYFTYY | BRCA |
| 344 | AVNALQSVY | AML, GBC, GBM, GC, NSCLCadeno, NSCLCother, NSCLCsquam, OC, PACA, PRCA, UEC |
| 345 | NTMDAVPRIDHY | GBC, GC |
| 346 | VAGLEAGVLY | BRCA, GBM, HCC, MEL, OC, UBC, UEC |
| 347 | SADHPGLTF | CRC |
| 349 | HLLSVSLYY | NSCLCsquam |
| 350 | LTDPQVSYV | MEL |
| 351 | VLDPMLDFY | HCC |
| 352 | YPVVAESMY | MEL |
| 353 | RLNGSVASY | OC |
| 355 | MADRGEARL | AML |
| 356 | NSENHILKY | GC, OSCAR |
| 358 | YMSPDIALLY | GBM, HCC, NSCLCadeno |
| 359 | NKEINYFMY | CCC |
| 360 | RFDDINQEF | HNSCC |
| 361 | FTAEEGQLY | BRCA, GBC, GBM, HCC, NSCLCadeno, NSCLCother, NSCLCsquam, PACA, PRCA, RCC, SCLC, UBC, UEC |
| 362 | SGALDEAAAY | GBM, NSCLCadeno, PRCA |
| 363 | LTDRDVSFY | HCC |
| 364 | DTGYLQLYY | BRCA |
| 365 | FVDTKVPEH | HCC, NHL, NSCLCsquam |
| 366 | ITVDVRDEF | GBM |
| 367 | LTDTGYLQLY | GBM, HNSCC, OC, OSCAR, UBC |
| 368 | ESAATGQLDY | OC |
| 369 | AVMEAAFVY | BRCA |
| 370 | RLSTIRHLY | HNSCC, MEL |
| 371 | WSDSTSQTIY | OSCAR |
| 372 | SRSDFEWVY | BRCA, OSCAR |
| 373 | FHADSDDESF | NHL |
| 374 | LTSVVVTLW | HCC |
| 375 | ASSLDSLHY | BRCA |
| 376 | EDDEDEDLY | NSCLCsquam |
| 377 | YADPSANRDLL | OC |
| 378 | TAKAPSTEY | GBC, NSCLCadeno, NSCLCother, NSCLCsquam |
| 379 | SLIIDDTEY | GBC, NSCLCsquam |
| 380 | VACGNNPVY | NSCLCadeno |
| 381 | ETSFSTSHY | HNSCC |
| 382 | YEPATMEQY | NSCLCsquam |
| 383 | PPDHAVGRTKY | UBC |
| 384 | RFRSITQSYY | CLL |
| 385 | SANALILTY | BRCA, MEL |
| 386 | NSALNPLLY | BRCA, NSCLCadeno |
| 387 | LMEKEDYHSLY | MEL |
| 388 | YTAHVGYSMY | NSCLCadeno |
| 389 | YDLVESTF | AML |
| 390 | FSEPFHLIVSY | CLL, MEL |
| 392 | TQHFVQENY | MEL |

TABLE 8-continued

Overview of presentation of selected tumor-associated peptides of the present invention across entities.

| SEQ ID No. | Sequence | Peptide Presentation on cancer entities |
|---|---|---|
| 393 | QVWGGQPVY | MEL |
| 394 | QVPLDCVLY | HNSCC, OSCAR |
| 395 | ILKGGSGTY | MEL |
| 396 | LPDPNVQKY | MEL |
| 397 | NSAINPLIY | NSCLCadeno, RCC, UEC |
| 398 | YYYDTHTNTY | HNSCC, PRCA |

AML: acute myeloid leukemia;
BRCA: breast cancer;
CCC: cholangiocellular carcinoma;
CLL: chronic lymphocytic leukemia;
CRC: colorectal cancer;
GBC: gallbladder cancer;
GBM: glioblastoma;
GC: gastric cancer;
HCC: hepatocellular carcinoma;
HNSCC: head and neck squamous cell carcinoma;
MEL: melanoma;
NHL: non-Hodgkin lymphoma;
NSCLCadeno: non-small cell lung cancer adenocarcinoma;
NSCLCother: NSCLC samples that could not unambiguously be assigned to NSCLCadeno or NSCLCsquam;
NSCLCsquam: squamous cell non-small cell lung cancer;
OC: ovarian cancer;
OSCAR: esophageal cancer;
PACA: pancreatic cancer;
PRCA: prostate cancer;
RCC: renal cell carcinoma;
SCLC: small cell lung cancer;
UBC: urinary bladder carcinoma;
UEC: uterine and endometrial cancer.

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, Mich., USA & Royston, Herts, UK); Bio-Options Inc. (Brea, Calif., USA); Geneticist Inc. (Glendale, Calif., USA); ProteoGenex Inc. (Culver City, Calif., USA); Tissue Solutions Ltd (Glasgow, UK).

Total RNA from tumor tissues for RNASeq experiments was obtained from: Asterand (Detroit, Mich., USA & Royston, Herts, UK); BioCat GmbH (Heidelberg, Germany); BioServe (Beltsville, Md., USA); Geneticist Inc. (Glendale, Calif., USA); Istituto Nazionale Tumori "Pascale" (Naples, Italy); ProteoGenex Inc. (Culver City, Calif., USA); University Hospital Heidelberg (Heidelberg, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer are shown in FIGS. 2A-2P. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 1 | TLDSTRTLY | | GBM | PRCA |
| 2 | VDPIGHLY | CRC, NHL, OC, PACA | GBC, NSCLCadeno, UEC | GC, HCC, HNSCC, MEL, NSCLCsquam, OSCAR, SCLC, UBC |
| 3 | FGTTPAAEYF | NSCLCadeno, NSCLCsquam, SCLC | | RCC |
| 4 | RIEAIRAEY | | | MEL |
| 5 | FMVIAGMPLFY | NSCLCadeno, NSCLCsquam | | RCC |
| 6 | ARDPITFSF | BRCA, CRC, OC, SCLC | NSCLCadeno, NSCLCother | AML |
| 7 | ASDDVRIEVGLY | BRCA, CRC, OC, SCLC | NSCLCadeno, NSCLCother | AML |
| 8 | TSRAANIPGY | BRCA, CLL | | NHL |
| 9 | QLDSTLDSY | OC | | BRCA |
| 10 | VSERTGISY | | MEL | |
| 11 | ASDHWRGRY | | PRCA | |
| 12 | YTDFVGEGLY | | PRCA | |
| 13 | NTHTGTRPY | GBC, MEL, NHL | OC | |
| 14 | QSEKEPGQQY | GBC | HCC | |
| 15 | YLDSSKPAVY | | BRCA, OC, UEC | |
| 16 | NSDISIPEY | | OC, UEC | |
| 17 | ASWAVLCYY | | PRCA | |
| 18 | RSDPVSLRY | | GBM | |
| 19 | LTEGHSGNY | | CLL, NHL | |
| 20 | LSAQHRMLA | CLL, SCLC | NHL | |
| 21 | LSSAVNPIIY | NSCLCsquam, UEC | GC, PACA | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 22 | VMDTLGLFY | HCC | PRCA | |
| 23 | DTDPLKAAGL | GBC, HCC, HNSCC, NSCLCadeno, NSCLCother, SCLC, UBC, UEC | CRC, GC, PRCA | |
| 24 | NLDHYTNAY | | SCLC, UEC | |
| 25 | AMMQEAQLAY | GBM | SCLC | |
| 26 | ASDDFRSKY | NSCLCsquam, OSCAR, UBC | HNSCC, MEL | |
| 27 | PSEVPVDSHY | CCC | MEL | |
| 28 | PSEVPVDSHYY | CCC | MEL | |
| 29 | TLEDLDNLYNY | CRC, GBC, NHL, UBC, UEC | BRCA, GC, HNSCC, MEL, NSCLCadeno, NSCLCsquam, OC, OSCAR, PACA | |
| 30 | VTTDKPRAY | | MEL | |
| 31 | VSDHLQAGMLGQY | NSCLCother, OSCAR | HNSCC | |
| 32 | GTDKQNSTLRY | | MEL | |
| 33 | SMDPVTGYQY | | MEL | |
| 34 | SSWSAGENDSY | NHL | HNSCC, MEL | |
| 35 | SWSAGENDSYS | NHL | HNSCC, MEL | |
| 36 | MTSTEQSLY | BRCA, HCC, MEL, OC, SCLC, UEC | PRCA | |
| 37 | MTSTEQSLYY | BRCA, HCC, MEL, OC, SCLC, UEC | PRCA | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 38 | KSWSQSSSLMY | CCC | HCC | |
| 39 | WSQSSSLMY | CCC | HCC | |
| 40 | TSDQLGYSY | | MEL | |
| 41 | HSDLLEDSKY | | BRCA | |
| 42 | ASDVDTLLK | | GBM | |
| 43 | ETEPERHLGSY | | PRCA | |
| 44 | IPSFNEMVY | | GBM | |
| 45 | NLDPNKIY | CRC, GC, MEL, NSCLCadeno, NSCLCsquam, OC, OSCAR, PACA | GBC | |
| 46 | RSDPGGGGLAYAAY | GBM, SCLC | AML | |
| 47 | WSDGVPLLY | | GBM | |
| 48 | FTTQDELLVY | | PRCA | |
| 49 | GSFSIQHTY | | PRCA | |
| 50 | ITDEDEDMLSY | | GBC, HCC | |
| 51 | STEERRLNY | | PRCA | |
| 52 | TTQDELLVY | | PRCA | |
| 53 | YLEDRPLSQLY | | MEL | |
| 54 | EVDIHTIHY | OSCAR | HNSCC | |
| 55 | ATEGDVLNY | NHL | CLL | |
| 56 | VTEYAEEIYQY | OC, OSCAR | AML, UEC | |
| 57 | ASDPASSTSCY | | NSCLCother | |
| 58 | YLENSASWY | | UEC | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 59 | FTDSQGNDIK | | MEL | |
| 60 | MTEKFLFLY | BRCA, CLL, NHL, RCC | UBC | |
| 61 | SSDIVALGGFLY | BRCA, NSCLCsquam, OSCAR, UBC | HNSCC | |
| 62 | VSELVTTGHY | | GBM | |
| 63 | TSEISQNALMY | NSCLCother, NSCLCsquam | NSCLCadeno | |
| 64 | TSEISQNALMYY | NSCLCother, NSCLCsquam | NSCLCadeno | |
| 65 | SSDFDPLVY | HCC | CRC | |
| 66 | IATVIQLFY | HNSCC, NSCLCsquam, OSCAR | UBC | |
| 67 | NVDQNQNSY | | MEL | |
| 68 | QSLPEFGLTY | GC, HNSCC, OSCAR, UBC | CRC | |
| 69 | QSLPEFGLTYY | GC, HNSCC, OSCAR, UBC | CRC | |
| 70 | YTELVEEKY | | UEC | |
| 71 | LTDSTTRTTY | | PACA | |
| 72 | VTDSTTKIAY | | PACA | |
| 73 | STDSASYY | | HCC | |
| 74 | EMEQQSQEY | OSCAR | HNSCC | |
| 75 | FTDYELKAY | | HCC | |
| 76 | QTDVERIKDTY | CCC, GC, HNSCC, NSCLCother, NSCLCsquam, UBC | OSCAR | |
| 77 | FTSDTGLEY | AML | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 78 | QLDSAVKNLY | CRC, NHL | | |
| 79 | ASDLEPRELLSY | GBM | | |
| 80 | ELCPLPGTSAY | GBM, OC, SCLC | | |
| 81 | YSDLHTPGRY | MEL, NSCLCadeno, SCLC | | |
| 82 | LTEKSHIRY | MEL | | |
| 83 | DTEFHGGLHY | GBC, GC, PACA | | |
| 84 | ESEMIKFASYY | HCC | | |
| 85 | SSDNYEHWLY | CLL | | |
| 86 | VDPASNTY | BRCA, CRC, GC, UEC | HCC, NSCLCadeno | GBC, HNSCC, MEL, NSCLCsquam, OC, OSCAR, SCLC, UBC |
| 87 | AFDDIATYF | MEL, NHL, NSCLCadeno | SCLC | HCC |
| 88 | KEVDPAGHSYI | CRC, PACA | BRCA, GC, HCC, NHL, NSCLCadeno, OC, UEC | GBC, HNSCC, MEL, NSCLCsquam, OSCAR, SCLC, UBC |
| 89 | EVYDGREHSAY | BRCA, CCC, OC, UBC | GBC, GC, HNSCC, NHL, NSCLCadeno, SCLC | HCC, MEL, NSCLCsquam, OSCAR |
| 90 | YEDHFPLLF | HCC, NSCLCadeno, UEC | GBC, GC, HNSCC, NSCLCsquam, OC, OSCAR, SCLC | MEL, UBC |
| 91 | CLVLVIVLLY | NSCLCadeno, NSCLCsquam | | RCC |
| 92 | TTDDTTAMASAS | HCC, UEC | GBC, GC, HNSCC, NSCLCadeno, | MEL, UBC |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| | | | NSCLCsquam, OC, OSCAR, SCLC | |
| 93 | HLKILSPIY | BRCA, CRC, NHL, OC, SCLC, UEC | NSCLCadeno, NSCLCother | AML |
| 94 | KPSAVKDSIY | OC | PRCA, SCLC | UEC |
| 95 | SSDPKAVMF | HCC, RCC | CCC, GC, MEL, NHL, NSCLCadeno, OC, PACA, UEC | CRC, GBC, HNSCC, NSCLCother, NSCLCsquam, OSCAR, SCLC, UBC |
| 96 | TATLLIVRY | BRCA, CRC, SCLC | NSCLCadeno, NSCLCother | AML |
| 97 | FPAPPAHWFY | OC | BRCA | |
| 98 | NFSDLVFTY | CLL, HNSCC, MEL, NHL, NSCLCadeno, NSCLCsquam, OC, PACA, RCC, UBC | BRCA, SCLC | GBM |
| 99 | AADSNPSEL | | PRCA | |
| 100 | TTSSAISWILY | | BRCA | |
| 101 | SITDVDFIY | CRC, SCLC | PRCA | |
| 102 | STIRGELFF | HCC, OC, RCC, SCLC | BRCA, CCC, CRC, GBC, GC, HNSCC, NSCLCadeno, NSCLCsquam, OSCAR, PACA, UBC, UEC | |
| 103 | ITDTLIHLM | | BRCA, OC, UEC | |
| 104 | ITDTLIHL | | BRCA, OC, UEC | |
| 105 | VVFDKSDLAKY | | PRCA | |
| 106 | EVVEGKEWGSFY | | CRC, GBC, GC, PACA | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 107 | TTENSGNYY | | CLL, NHL | |
| 108 | NSNLKFLEV | BRCA, CRC, GC, MEL, NHL, NSCLCadeno, NSCLCother, OSCAR, PACA, SCLC, UEC | HNSCC, NSCLCsquam, OC | |
| 109 | ISEDKSISF | | MEL | |
| 110 | IGDKVDAVY | NSCLCadeno, UBC | HNSCC, NSCLCsquam, OSCAR | |
| 111 | TPIPFDKILY | CRC, NSCLCsquam, OC, UBC, UEC | BRCA, CCC, GBC, GC, HNSCC, NSCLCadeno, OSCAR, PACA | |
| 112 | KASSVSAEDGY | BRCA, SCLC, UBC | PRCA | |
| 113 | ASCRSSAEY | GBC, GC, NSCLCadeno, NSCLCother, PACA, UEC | CCC, HNSCC, NSCLCsquam, OSCAR, UBC | |
| 114 | AVAAAAGASLY | | UEC | |
| 115 | NEIDIHSIYFY | NSCLCother, OSCAR | HNSCC | |
| 116 | RSDIGEFEW | AML, BRCA, CCC, CRC, GBC, GBM, GC, HCC, HNSCC, MEL, NHL, NSCLCadeno, NSCLCother, NSCLCsquam, OC, OSCAR, PACA, UBC, UEC | CLL, SCLC | |
| 117 | SPAKQFNIY | AML, BRCA, CCC, CRC, GBC, GBM, GC, HCC, HNSCC, MEL, NHL, NSCLCadeno, | CLL, SCLC | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
| --- | --- | --- | --- | --- |
| | | over-expressed (+) | highly over-expressed (++) | very highly over-expressed (+++) |
| | | NSCLCother, NSCLCsquam, OC, OSCAR, PACA, UBC, UEC | | |
| 118 | LTWAHSAKY | CCC | MEL | |
| 119 | TVFDENLSRY | NSCLCother, OSCAR | HNSCC | |
| 120 | LVDENQSWY | NSCLCother, OSCAR | HNSCC | |
| 121 | SADEAHGLL | BRCA, GC, HNSCC, MEL, NHL, NSCLCadeno, NSCLCother, NSCLCsquam, OC, OSCAR, PACA, RCC, UBC, UEC | CCC, CRC, GBC | |
| 122 | ISEAPLTEV | | MEL | |
| 123 | LLKAKDILY | | HCC, PRCA | |
| 124 | FLKVTGYDKDDY | | MEL | |
| 125 | FQYELRELY | | MEL | |
| 126 | TTDPKKFQY | | MEL | |
| 127 | VPFNLITEY | HCC | MEL | |
| 128 | YTEFVDATFTK | OSCAR | HNSCC | |
| 129 | STIDFRAGF | | MEL | |
| 130 | YIGLKGLYF | HCC | MEL | |
| 131 | LEDGIEQSAY | AML | CLL | |
| 132 | RTHIGYKVY | | MEL | |
| 133 | ITDVGPGNY | | MEL | |
| 134 | SAPSSSGSPLY | CLL | SCLC | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 135 | TFDKQIVLL | CCC | HCC | |
| 136 | RRLNFSGFGY | | SCLC | |
| 137 | EAYLERIGY | | BRCA | |
| 138 | IPVHDSVGVTY | | GBM | |
| 139 | PVHDSVGVTY | | GBM | |
| 140 | SQHIFTVSY | | GBM | |
| 141 | DAVAPGREY | CCC | HCC | |
| 142 | IEKFAVLY | | GBM | |
| 143 | HVSGQMLYF | BRCA | UEC | |
| 144 | RTIEGDFLW | | GBM | |
| 145 | LSDAVHVEF | | CLL, NHL | |
| 146 | LCATVCGTEQY | BRCA | GBM, MEL | |
| 147 | AQVQDTGRY | | MEL | |
| 148 | GTKQWVHARY | | CLL, NHL | |
| 149 | PIMSSSQALY | | MEL | |
| 150 | FTTLSDLQTNMA | AML, GBC, HCC, HNSCC, NSCLCadeno, OC, OSCAR | MEL, SCLC | |
| 151 | YEVDTKLLSL | GBC, HCC, HNSCC, NSCLCadeno, NSCLCsquam, OC, OSCAR | MEL, SCLC | |
| 152 | YLEDRPLSQ | | MEL | |
| 153 | HSIEVFTHY | | MEL | |
| 154 | SIEVFTHY | | MEL | |
| 155 | HTMEVTVY | | MEL | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 156 | STALSILLL | | GBM | |
| 157 | GLIEVVTGY | | BRCA | |
| 158 | EVTDRNMLAF | OC | BRCA | |
| 159 | RQAPGPARDY | NSCLCsquam, UBC | HNSCC, OSCAR | |
| 160 | EVLGEEMYAY | BRCA | PRCA | |
| 161 | EAAPDIMHY | BRCA, HCC, MEL, OC | PRCA | |
| 162 | IADNPQLSFY | PRCA | BRCA | |
| 163 | KIRAEVLSHY | | CLL | |
| 164 | KLAGTVFQY | BRCA, CRC, GC, HNSCC, MEL, NSCLCadeno, NSCLCother, NSCLCsquam, OSCAR, PACA, SCLC, UBC | CCC, GBC | |
| 165 | VSVYNSYPY | | PRCA | |
| 166 | YHRICELLSDY | BRCA, GBC, NSCLCsquam, OC, OSCAR, PACA, SCLC | PRCA | |
| 167 | RAVQPGETY | CCC | HCC | |
| 168 | VQPGETYTY | CCC | HCC | |
| 169 | TVDNANILL | NSCLCsquam, UBC | HNSCC, OSCAR | |
| 170 | VQIAKGMNY | HNSCC | GBM | |
| 171 | ITDFGLAKL | HNSCC | GBM | |
| 172 | FSEPFHLIV | MEL | CLL, NHL | |
| 173 | QSTTGVSHY | | GBM | |
| 174 | TSEVEGLAFVSY | | GBM | |
| 175 | GLEYEAPKLY | | AML | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 176 | HTDLESPSAVY | | UBC | |
| 177 | LVDGKWQEF | | UBC | |
| 178 | TQRTSFQFY | NSCLCother, NSCLCsquam | NSCLCadeno | |
| 179 | SSTDFTFASW | GC, HNSCC, NSCLCsquam, OSCAR, UBC | CRC | |
| 180 | AQISDTGRY | | MEL | |
| 181 | SVTDLIGGKW | AML, NSCLCsquam, OSCAR | HNSCC, UBC | |
| 182 | TQPELSSRY | BRCA, CRC, GC, HNSCC, NSCLCadeno, NSCLCother, NSCLCsquam, OSCAR, PACA, UBC | CCC, GBC | |
| 183 | LADTDLGMTF | HNSCC, MEL, NHL, NSCLCadeno, NSCLCother, SCLC | GBC | |
| 184 | KTIQEVAGY | | GBM | |
| 185 | NSDESADSEPHKY | | NHL | |
| 186 | AVSSGLFFY | NHL | CLL | |
| 187 | TQKSVQVLAY | | GBM | |
| 188 | DIPDYLLQY | | NHL | |
| 189 | FRGVFVHRY | MEL, NSCLCadeno, OC, SCLC | GBC, NHL | |
| 190 | VSSTVHNLY | BRCA, OC | PRCA | |
| 191 | FTRAFDQLRM | | CLL | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 192 | LAFYYGMY | GBM, HNSCC, NSCLCadeno, OSCAR | NSCLCsquam | |
| 193 | SQNGQLIHY | | MEL | |
| 194 | CYTADNEMGY | NSCLCother, NSCLCsquam | NSCLCadeno | |
| 195 | YTADNEMGYY | NSCLCother, NSCLCsquam | NSCLCadeno | |
| 196 | RLAQYTIERY | GBC, GC, UEC | PACA | |
| 197 | NDEIDKLTGY | | PRCA | |
| 198 | KLTDYINANY | | GBM | |
| 199 | LCAAVLAKY | | HCC | |
| 200 | SLPEFGLTY | GC, HNSCC, OSCAR, UBC | CRC | |
| 201 | SLPEFGLTYY | GC, HNSCC, OSCAR, UBC | CRC | |
| 202 | QTDINGGSLK | | MEL | |
| 203 | LSQDELSKF | BRCA, CCC, NHL, NSCLCsquam, OC, OSCAR, UBC, UEC | GBC | |
| 204 | NVKEAPTEY | NHL | CLL | |
| 205 | RMQEGSEVY | NHL | CLL | |
| 206 | RVFVAVTLY | | PRCA | |
| 207 | LLEGEDAHLTQY | NSCLCsquam, UBC | HNSCC, OSCAR | |
| 208 | LLISKAEDY | | BRCA | |
| 209 | EADPFLKYL | OC, OSCAR, UEC | AML | |
| 210 | LLEADPFLKY | OC, OSCAR, UEC | AML | |
| 211 | YLNEWGSRF | GBC, NSCLCadeno, NSCLCsquam, OSCAR, UBC | HNSCC | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 212 | MMTDLTSVY | | PACA | |
| 213 | VSDSTTEITY | | PACA | |
| 214 | VQDPSLPVY | CLL, CRC, GBM, GC, HNSCC, MEL, NSCLCadeno, NSCLCsquam, OC, OSCAR, PACA, PRCA, SCLC, UBC | NHL | |
| 215 | DTLEAATSLY | NSCLCadeno, NSCLCsquam, OC | SCLC | |
| 216 | NSMLDPLVY | UBC | BRCA | |
| 217 | LMDEGAVLTL | CLL, NHL | CRC | |
| 218 | FTAQLQLY | NSCLCother, NSCLCsquam | NSCLCadeno | |
| 219 | KTELETALYY | GBM, HNSCC, NSCLCsquam, OSCAR, PACA, RCC | CRC | |
| 220 | DVERIKDTY | CCC, GC, HNSCC, NSCLCother, NSCLCsquam, UBC | OSCAR | |
| 221 | TDVERIKDTY | CCC, GC, HNSCC, NSCLCother, NSCLCsquam, UBC | OSCAR | |
| 222 | GSPDAVVSY | CCC, CRC, GBC, GC, HCC, HNSCC, MEL, NSCLCsquam, OC, OSCAR, PACA, SCLC | | |
| 223 | NAVDVVPSSF | BRCA, CCC, GBC, NSCLCsquam, | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| | | OC, OSCAR, UBC, UEC | | |
| 224 | RTDEGDNRVW | GBC, HNSCC, NSCLCadeno, NSCLCother, NSCLCsquam, OC, OSCAR, UBC | | |
| 225 | STDPNIVRK | MEL, PRCA, SCLC | | |
| 226 | QITPKHNGLY | CCC, MEL | | |
| 227 | ESAPKEVSRY | RCC, UBC | | |
| 228 | KSFDDIAKY | GBC, HCC, NHL, NSCLCadeno, OC, PACA | | |
| 229 | MTDVFIDY | HCC | | |
| 230 | CVIETFHKY | HNSCC, MEL | | |
| 231 | LLPLLVMAY | CLL | | |
| 232 | RYLNIVHATQLY | CLL | | |
| 233 | RINSATGQY | CLL | | |
| 234 | YTDLTTIQV | BRCA, HNSCC, MEL, NHL, NSCLCadeno, OSCAR | | |
| 235 | SIEIDHTQY | HCC | | |
| 236 | VLDSLLAQY | GBC, HCC, HNSCC, NSCLCsquam, SCLC | | |
| 237 | AQEAAVFLTLY | PRCA | | |
| 238 | ETDWGLLKGHTY | UEC | | |
| 239 | SSERGSPIEKY | BRCA | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 240 | EVLDSLLAQY | GBC, HCC, HNSCC, MEL, NSCLCsquam, OC, SCLC | | |
| 241 | SLMVASLTY | AML, CCC, PACA, UEC | | |
| 242 | GTNLPTLLW | SCLC | | |
| 243 | LTSEDTGAY | SCLC | | |
| 244 | VTKYIAGPY | CCC | | |
| 245 | LSDNAANRY | AML | | |
| 246 | ARLEGEIATY | HNSCC, OSCAR | | |
| 247 | SMIRVGTNY | GBM, SCLC | | |
| 248 | VTDIDELGK | AML | | |
| 249 | GVGFTELEY | HCC | | |
| 250 | GYVCNACGLY | BRCA | | |
| 251 | GIEMTYETY | BRCA, CLL, SCLC | | |
| 252 | DTTSHTYLQY | GBM | | |
| 253 | YLESHGLAY | GBM, HCC, MEL, PACA, SCLC | | |
| 254 | FLFNDALLY | CCC, GBC, HNSCC, NHL, NSCLCadeno, NSCLCsquam, PACA | | |
| 255 | WELDSLEY | BRCA, CCC, GBC, GC, HNSCC, MEL, NHL, NSCLCadeno, NSCLCsquam, OSCAR, PACA, UBC, UEC | | |
| 256 | HAFESNNFIY | CCC, GBC, NSCLCadeno | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 257 | KSEMNVNMKY | CCC, GBC, NSCLCadeno | | |
| 258 | RPSSVLTIY | GBM, HCC, HNSCC, NSCLCadeno, NSCLCsquam, OSCAR, SCLC, UBC | | |
| 259 | APDEVVALL | BRCA, CCC, MEL, OC, UEC | | |
| 260 | KPTEDSANVY | GBM | | |
| 261 | MTEGSTVNTEY | CCC, GBC, MEL, OC, RCC, SCLC, UEC | | |
| 262 | NVKHFLNDLY | CCC, GBC, MEL, OC, RCC, SCLC, UEC | | |
| 263 | DCMDTEGSYM | GBM, NSCLCother, OC, SCLC | | |
| 264 | YRDPVFVSL | CRC | | |
| 265 | LSDIDSRYI | BRCA, CCC, GBC, HCC, HNSCC, MEL, NHL, OC, SCLC, UEC | | |
| 266 | LTDSFLLRF | HCC | | |
| 267 | IVADDTVY | PRCA | | |
| 268 | AILHHLYFY | PRCA | | |
| 269 | LPSPAATIWDY | CRC, GC, NSCLCadeno, PACA, RCC | | |
| 270 | DLKIDLAAQY | HNSCC, NSCLCsquam, OSCAR | | |
| 271 | VAEPPVVCSY | OC, SCLC | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 272 | IPQDECLRY | BRCA, GC, HCC, SCLC | | |
| 273 | CGPNEINHFY | MEL, UBC | | |
| 274 | YADIHGDLL | BRCA, CCC | | |
| 275 | ESDEMENLLTY | BRCA, PRCA | | |
| 276 | QITSFASGTSY | AML | | |
| 277 | LPAPGFLFY | BRCA | | |
| 278 | AATVKSDIY | BRCA, NHL, PRCA, SCLC | | |
| 279 | LMTVLLKY | NSCLCother | | |
| 280 | TTEMVSNESVDY | CCC, GBC, RCC | | |
| 281 | YPDLSELLM | CCC, GBC, MEL, NHL, NSCLCother, OSCAR, SCLC, UBC | | |
| 282 | QAMPSWPTAAY | MEL | | |
| 283 | ETILVSSSY | HCC | | |
| 284 | TCSHTFVYY | CCC, NSCLCother, NSCLCsquam, SCLC | | |
| 285 | VLPHHSEGACVY | PRCA | | |
| 286 | ATDMEGNLNY | GBM | | |
| 287 | ENSIEDLQY | BRCA, PRCA, UEC | | |
| 288 | TEEKFVSY | CRC, PACA, SCLC | | |
| 289 | YTSHEDIGY | NSCLCother | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 290 | GQFTGTAGACRY | OC | | |
| 291 | TSDVTGSLTY | BRCA, CCC, GC, MEL, NHL, NSCLCother, NSCLCsquam, OC, RCC | | |
| 292 | VLDFAPPGASAY | OC | | |
| 293 | IISVLIAIY | SCLC | | |
| 294 | MMEMEGMY | PRCA | | |
| 295 | GQRLDEAMISY | OC, UBC | | |
| 296 | HMLAAMAY | GBC, HCC, HNSCC, MEL, NSCLCadeno, NSCLCsquam, OC, OSCAR, UBC | | |
| 297 | RLDEAMISY | OC, UBC | | |
| 298 | KFDVINHYF | GBC, HCC, HNSCC, MEL, NSCLCadeno, NSCLCsquam, OC, OSCAR, UBC | | |
| 299 | EVDSVALSL | GC, NHL, PACA | | |
| 300 | VSINPNSGDIY | GBM, OC, UEC | | |
| 301 | ESQTCASDY | CCC, GBC, GC, HNSCC, NSCLCsquam, OSCAR, UBC, UEC | | |
| 302 | FYLSTPENYHY | MEL | | |
| 303 | GFGGLSSQGVYY | GC | | |
| 304 | FSENLIYTYI | SCLC | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 305 | YADLLIYTY | HNSCC, OC, UBC, UEC | | |
| 306 | KSFETTVRY | MEL | | |
| 307 | DTDDRELRY | GBM, SCLC | | |
| 308 | ELAAGQVVY | GBM, SCLC | | |
| 309 | EVDRNLIQY | GBM, SCLC | | |
| 310 | KAFQELGVRY | GBM, SCLC | | |
| 311 | TVTDGTHTDFY | GBM, SCLC | | |
| 312 | VTDGINPLI | GBM, SCLC | | |
| 313 | VTDGTHTDFY | GBM, SCLC | | |
| 314 | PPEANSLQGALY | GBM | | |
| 315 | VLKIELETY | OC, UEC | | |
| 316 | YTCEECGQAF | CLL | | |
| 317 | EDLLEVLDMY | SCLC | | |
| 318 | YMTSMALNY | AML | | |
| 319 | FTDPHIITF | CCC, NSCLCother, NSCLCsquam, SCLC | | |
| 320 | QALQDKLQTFY | CCC, SCLC | | |
| 321 | DGIADASNLSYY | GBC, GC, PACA | | |
| 322 | FSELNPLALY | BRCA, HNSCC, OC, OSCAR, UBC | | |
| 323 | KTLQKPVLPLY | CLL | | |
| 324 | RTGIFPYRF | CLL | | |
| 325 | LQKPVLPLY | CLL | | |
| 326 | STSRLTLFS | PRCA | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 327 | IMLSVDQHLY | CCC | | |
| 328 | LLDEDNNIKL | CRC, SCLC | | |
| 329 | NTDSMTLNNTAY | AML, CLL, CRC, MEL, NHL | | |
| 330 | EGELSEGEHWY | PRCA | | |
| 331 | YLYQAPGSLALY | BRCA, GC | | |
| 332 | SLISFKYTSY | SCLC | | |
| 333 | LSDPQAELQFY | GBM | | |
| 334 | PSSMPECLSY | CRC, NHL | | |
| 335 | PSSMPECLSYY | CRC, NHL | | |
| 336 | ATNIQLNIDTY | BRCA, CRC, GBC, GC, RCC | | |
| 337 | FTESNQYNIY | UBC | | |
| 338 | YSPDSFNVSW | MEL, OC | | |
| 339 | ESMDIFPLGW | CLL | | |
| 340 | SVDSNLVAY | PRCA | | |
| 341 | PANYLGKMTY | PRCA | | |
| 342 | QTYMDGLLHY | HNSCC, OSCAR | | |
| 343 | YFGNYFTYY | NSCLCother, SCLC | | |
| 344 | AVNALQSVY | CRC, PRCA | | |
| 345 | NTMDAVPRIDHY | CRC | | |
| 346 | VAGLEAGVLY | SCLC | | |
| 347 | SADHPGLTF | GBM | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 348 | DSTDGCLLSF | MEL | | |
| 349 | HLLSVSLYY | HCC | | |
| 350 | LTDPQVSYV | MEL | | |
| 351 | VLDPMLDFY | OC, UEC | | |
| 352 | YPVVVAESMY | OC, UEC | | |
| 353 | RLNGSVASY | OC, UEC | | |
| 354 | EIIRYIFAY | AML | | |
| 355 | MADRGEARL | GBC, NHL | | |
| 356 | NSENHILKY | HNSCC, SCLC | | |
| 357 | MSPDIALLYL | NSCLCother | | |
| 358 | YMSPDIALLY | NSCLCother | | |
| 359 | NKEINYFMY | HCC | | |
| 360 | RFDDINQEF | HNSCC, OSCAR | | |
| 361 | FTAEEGQLY | HCC, PRCA | | |
| 362 | SGALDEAAAY | HCC, PRCA | | |
| 363 | LTDRDVSFY | HCC | | |
| 364 | DTGYLQLYY | HNSCC, OC, OSCAR, UBC | | |
| 365 | FVDTKVPEH | BRCA | | |
| 366 | ITVDVRDEF | HNSCC, OC, OSCAR, UBC | | |
| 367 | LTDTGYLQLY | HNSCC, OC, OSCAR, UBC | | |
| 368 | ESAATGQLDY | GBM | | |
| 369 | AVMEAAFVY | PRCA | | |
| 370 | RLSTIRHLY | BRCA, GBC, GC, NSCLCadeno, NSCLCsquam, OSCAR, PACA | | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 371 | WSDSTSQTIY | HNSCC | | |
| 372 | SRSDFEWVY | BRCA, GC, UBC | | |
| 373 | FHADSDDESF | CRC | | |
| 374 | LTSVVVTLW | AML | | |
| 375 | ASSLDSLHY | BRCA | | |
| 376 | EDDEDEDLY | CLL | | |
| 377 | YADPSANRDLL | GBM | | |
| 378 | TAKAPSTEY | CRC, GC, NSCLCadeno, PACA | | |
| 379 | SLIIDDTEY | GC, PACA, UBC, UEC | | |
| 380 | VACGNNPVY | GC, PACA, UBC, UEC | | |
| 381 | ETSFSTSHY | HNSCC, OSCAR | | |
| 382 | YEPATMEQY | MEL | | |
| 383 | PPDHAVGRTKY | PRCA | | |
| 384 | RFRSITQSYY | BRCA, CLL | | |
| 385 | SANALILTY | BRCA, CLL | | |
| 386 | NSALNPLLY | NSCLCadeno, UEC | RCC | |
| 387 | LMEKEDYHSLY | MEL | | |
| 388 | YTAHVGYSMY | UEC | | |
| 389 | YYDLVESTF | AML | | |
| 390 | FSEPFHLIVSY | MEL | CLL, NHL | |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, bile duct, blood cells, blood vessels, bone marrow, brain, esophagus, eye, gallbladder, heart, head and neck, kidney, large intestine, liver, lung, lymph node, nerve, parathyroid, pancreas, pituitary, pleura, skeletal muscle, skin, small intestine, spleen, stomach, thyroid gland, trachea, ureter, urinary bladder. In case expression data for several samples of the same tissue type were available, the arithmetic mean of all respective samples was used for the calculation. AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; HCC: hepatocellular carcinoma; HNSCC: head and neck squamous cell carcinoma; MEL: melanoma; NHL: non-Hodgkin lymphoma; NSCLCadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

| Seq ID No | Sequence | Gene Expression in tumor samples | | |
|---|---|---|---|---|
| | | over-expressed (+) | highly over-expressed (++) | very highly over-expressed (+++) |
| 391 | GSNPARYEF | BRCA, CRC, GC, UEC | HCC, NSCLCadeno | GBC, HNSCC, MEL, NSCLCsquam, OC, OSCAR, SCLC, UBC |
| 392 | TQHFVQENY | CRC, NHL, PACA | GBC, NSCLCadeno, UEC | GC, HCC, HNSCC, MEL, NSCLCsquam, OSCAR, SCLC, UBC |
| 393 | QVWGGQPVY | | MEL | |
| 394 | QVPLDCVLY | | MEL | |
| 395 | ILKGGSGTY | | MEL | |
| 396 | LPDPNVQKY | NHL | | |
| 397 | NSAINPLIY | CRC, GBC, GC | | |
| 398 | YYYDTHTNTY | CRC | | |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*01 restricted TUMAPs of the invention, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nurnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 433) from modified Melan-A/MART-1) and A*0201/DDX5-001 (YLLPAIVHI from DDX5, SEQ ID NO. 434), respectively.

800.000 beads/200 μl were coated in 96-well plates in the presence of 4×12.5 ng different biotin-pMHC, washed and 600 ng biotin anti-CD28 were added subsequently in a volume of 200 μl. Stimulations were initiated in 96-well plates by co-incubating 1×10$^6$ CD8+ T cells with 2×10$^6$ washed coated beads in 200 μl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described(Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10x the median of the negative control stimulations).

In Vitro Immunogenicity

In vitro immunogenicity for acute myeloid leukemia, breast cancer, cholangiocellular carcinoma, chronic lymphocytic leukemia, colorectal cancer, gallbladder cancer, glioblastoma, gastric cancer, hepatocellular carcinoma, head and neck squamous cell carcinoma, melanoma, non-Hodgkin lymphoma, lung cancer (including non-small cell lung cancer adenocarcinoma, squamous cell non-small cell lung cancer, and small cell lung cancer), ovarian cancer, esophageal cancer, pancreatic cancer, prostate cancer, renal cell carcinoma, urinary bladder carcinoma, uterine and endometrial cancer peptides was examined. For tested HLA class I peptides, in vitro immunogenicity could be demonstrated by generation of peptide specific T-cell lines. Exemplary flow cytometry results after TUMAP-specific multimer staining for two peptides of the invention are shown in FIGS. 2A-2P and 3A-3G together with corresponding negative controls. Results for 13 peptides from the invention are summarized in Table 10a and results for further 28 peptides from the invention are summarized in Table 10b.

TABLE 10a in vitro immunogenicity of HLA class I peptides of the invention
Exemplary results of in vitro immunogenicity experiments conducted by the applicant for the peptides of the invention.
<20% = +; 20%-49% = ++; 50%-69% = +++; > = 70% = ++++

| Seq ID No | Sequence | Wells positive [%] |
|---|---|---|
| 399 | YVGKEHMFY | + |
| 400 | NTDNNLAVY | + |
| 401 | VWSNVTPLKF | + |
| 403 | SADDIRGIQSLY | + |
| 404 | FVDNQYWRY | + |
| 408 | VWSDVTPLTF | + |
| 414 | LTEGHSGNYY | + |
| 415 | VWSDVTPLNF | + |
| 417 | KLDRSVFTAY | ++++ |
| 420 | VTDLEMPHY | + |
| 421 | RSDPGGGGLAY | + |
| 427 | LTDYINANY | + |
| 429 | VSDSECLSRY | ++ |

TABLE 10b in vitro immunogenicity of HLA class I peptides of the invention
Exemplary results of in vitro immunogenicity experiments conducted by the applicant for the peptides of the invention.
<20% = +; 20%-49% = ++; 50%-69% = +++; > = 70% = ++++

| SEQID | Sequence | Wells positive |
|---|---|---|
| 10 | VSERTGISY | + |
| 11 | ASDHWRGRY | +++ |
| 12 | YTDFVGEGLY | + |
| 18 | RSDPVSLRY | ++ |
| 19 | LTEGHSGNY | + |
| 24 | NLDHYTNAY | + |
| 26 | ASDDFRSKY | ++ |
| 27 | PSEVPVDSHY | + |
| 33 | SMDPVTGYQY | + |
| 37 | MTSTEQSLYY | + |
| 42 | ASDVDTLLK | + |
| 53 | YLEDRPLSQLY | + |
| 54 | EVDIHTIHY | + |
| 60 | MTEKFLFLY | + |
| 61 | SSDIVALGGFLY | ++ |

TABLE 10b-continued in vitro immunogenicity of HLA class I peptides
of the invention
Exemplary results of in vitro immunogenicity
experiments conducted by the applicant for the
peptides of the invention.
<20% = +; 20%-49% = ++; 50%-69% = +++;
> = 70% = ++++

| SEQID | Sequence | Wells positive |
|---|---|---|
| 64 | TSEISQNALMYY | + |
| 70 | YTELVEEKY | + |
| 71 | LTDSTTRTTY | + |
| 73 | STDSASYY | + |
| 75 | FTDYELKAY | + |
| 77 | FTSDTGLEY | +++ |
| 79 | ASDLEPRELLSY | + |
| 81 | YSDLHTPGRY | + |
| 82 | LTEKSHIRY | + |
| 83 | DTEFHGGLHY | + |
| 84 | ESEMIKFASYY | + |
| 386 | NSALNPLLY | + |
| 387 | LMEKEDYHSLY | + |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizes (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006)

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100-fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

MHC:peptide binding results for 391 peptides from the invention are summarized in Table 11.

TABLE 11

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 1 | TLDSTRTLY | ++++ |
| 2 | VDPIGHLY | ++ |
| 3 | FGTTPAAEYF | ++ |
| 4 | RIEAIRAEY | ++ |
| 5 | FMVIAGMPLFY | +++ |
| 6 | ARDPITFSF | ++ |
| 7 | ASDDVRIEVGLY | ++++ |
| 8 | TSRAANIPGY | + |
| 9 | QLDSTLDSY | +++ |
| 10 | VSERTGISY | +++ |
| 11 | ASDHWRGRY | +++ |
| 12 | YTDFVGEGLY | +++ |
| 13 | NTHTGTRPY | ++ |
| 14 | QSEKEPGQQY | +++ |
| 15 | YLDSSKPAVY | +++ |
| 16 | NSDISIPEY | +++ |
| 17 | ASWAVLCYY | +++ |
| 18 | RSDPVSLRY | ++++ |
| 19 | LTEGHSGNY | ++++ |
| 20 | LSAQHRMLA | ++ |
| 21 | LSSAVNPIIY | ++ |
| 22 | VMDTLGLFY | ++++ |
| 23 | DTDPLKAAGL | + |
| 24 | NLDHYTNAY | +++ |
| 25 | AMMQEAQLAY | +++ |
| 26 | ASDDFRSKY | +++ |
| 27 | PSEVPVDSHY | ++++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 28 | PSEVPVDSHYY | +++ |
| 29 | TLEDLDNLYNY | +++ |
| 30 | VTTDKPRAY | ++ |
| 31 | VSDHLQAGMLGQY | +++ |
| 32 | GTDKQNSTLRY | +++ |
| 33 | SMDPVTGYQY | +++ |
| 34 | SSWSAGENDSY | +++ |
| 35 | SWSAGENDSYS | + |
| 36 | MTSTEQSLY | +++ |
| 37 | MTSTEQSLYY | +++ |
| 38 | KSWSQSSSLMY | +++ |
| 39 | WSQSSSLMY | ++++ |
| 40 | TSDQLGYSY | +++ |
| 41 | HSDLLEDSKY | +++ |
| 42 | ASDVDTLLK | +++ |
| 43 | ETEPERHLGSY | +++ |
| 44 | IPSFNEMVY | ++ |
| 45 | NLDPNKIY | + |
| 46 | RSDPGGGGLAYAAY | ++++ |
| 47 | WSDGVPLLY | ++++ |
| 48 | FTTQDELLVY | +++ |
| 49 | GSFSIQHTY | ++ |
| 50 | ITDEDEDMLSY | +++ |
| 51 | STEERRLNY | +++ |
| 52 | TTQDELLVY | +++ |
| 53 | YLEDRPLSQLY | ++++ |
| 54 | EVDIHTIHY | +++ |
| 55 | ATEGDVLNY | +++ |
| 56 | VTEYAEEIYQY | +++ |
| 57 | ASDPASSTSCY | +++ |
| 58 | YLENSASWY | ++++ |
| 59 | FTDSQGNDIK | +++ |
| 60 | MTEKFLFLY | ++++ |
| 61 | SSDIVALGGFLY | +++ |
| 62 | VSELVTTGHY | +++ |
| 63 | TSEISQNALMY | ++++ |
| 64 | TSEISQNALMYY | +++ |
| 65 | SSDFDPLVY | ++++ |
| 67 | NVDQNQNSY | +++ |
| 68 | QSLPEFGLTY | ++ |
| 69 | QSLPEFGLTYY | ++ |
| 70 | YTELVEEKY | +++ |
| 71 | LTDSTTRTTY | +++ |
| 72 | VTDSTTKIAY | +++ |
| 73 | STDSASYY | ++++ |
| 74 | EMEQQSQEY | ++++ |
| 75 | FTDYELKAY | ++++ |
| 76 | QTDVERIKDTY | +++ |
| 77 | FTSDTGLEY | ++++ |
| 78 | QLDSAVKNLY | +++ |
| 79 | ASDLEPRELLSY | +++ |
| 80 | ELCPLPGTSAY | ++ |
| 81 | YSDLHTPGRY | +++ |
| 82 | LTEKSHIRY | +++ |
| 83 | DTEFHGGLHY | +++ |
| 84 | ESEMIKFASYY | ++++ |
| 85 | SSDNYEHWLY | ++++ |
| 86 | VDPASNTY | ++ |
| 87 | AFDDIATYF | ++ |
| 88 | KEVDPAGHSYI | ++ |
| 89 | EVYDGREHSAY | ++ |
| 90 | YEDHFPLLF | ++ |
| 92 | TTDDTTAMASAS | ++ |
| 93 | HLKILSPIY | +++ |
| 94 | KPSAVKDSIY | ++ |
| 95 | SSDPKAVMF | ++ |
| 97 | FPAPPAHWFY | ++ |
| 98 | NFSDLVFTY | ++ |
| 99 | AADSNPSEL | ++ |
| 100 | TTSSAISWILY | +++ |
| 101 | SITDVDFIY | ++ |
| 102 | STIRGELFF | ++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 103 | ITDTLIHLM | +++ |
| 104 | ITDTLIHL | ++ |
| 105 | VVFDKSDLAKY | ++ |
| 106 | EVVEGKEWGSFY | +++ |
| 107 | TTENSGNYY | ++++ |
| 108 | NSNLKFLEV | ++ |
| 109 | ISEDKSISF | ++ |
| 110 | IGDKVDAVY | ++ |
| 111 | TPIPFDKILY | ++ |
| 112 | KASSVSAEDGY | ++ |
| 113 | ASCRSSAEY | ++++ |
| 114 | AVAAAAGASLY | ++ |
| 115 | NEIDIHSIYFY | ++ |
| 116 | RSDIGEFEW | ++ |
| 117 | SPAKQFNIY | +++ |
| 118 | LTWAHSAKY | +++ |
| 119 | TVFDENLSRY | ++ |
| 120 | LVDENQSWY | +++ |
| 121 | SADEAHGLL | ++ |
| 122 | ISEAPLTEV | ++ |
| 123 | LLKAKDILY | ++ |
| 124 | FLKVTGYDKDDY | ++ |
| 125 | FQYELRELY | ++++ |
| 126 | TTDPKKFQY | ++++ |
| 127 | VPFNLITEY | + |
| 128 | YTEFVDATFTK | ++++ |
| 129 | STIDFRAGF | ++ |
| 130 | YIGLKGLYF | ++ |
| 131 | LEDGIEQSAY | ++ |
| 132 | RTHIGYKVY | +++ |
| 133 | ITDVGPGNY | +++ |
| 134 | SAPSSSGSPLY | ++ |
| 135 | TFDKQIVLL | ++ |
| 136 | RRLNFSGFGY | +++ |
| 137 | EAYLERIGY | +++ |
| 138 | IPVHDSVGVTY | +++ |
| 139 | PVHDSVGVTY | ++ |
| 140 | SQHIFTVSY | ++ |
| 141 | DAVAPGREY | ++ |
| 142 | IEKFAVLY | +++ |
| 143 | HVSGQMLYF | ++ |
| 144 | RTIEGDFLW | ++ |
| 145 | LSDAVHVEF | +++ |
| 146 | LCATVCGTEQY | ++ |
| 147 | AQVQDTGRY | +++ |
| 148 | GTKQWVHARY | + |
| 149 | PIMSSSQALY | ++ |
| 150 | FTTLSDLQTNMA | ++ |
| 151 | YEVDTKLLSL | ++ |
| 152 | YLEDRPLSQ | ++ |
| 153 | HSIEVFTHY | ++ |
| 154 | SIEVFTHY | +++ |
| 155 | HTMEVTVY | +++ |
| 156 | STALSILLL | ++ |
| 157 | GLIEVVTGY | ++++ |
| 158 | EVTDRNMLAF | +++ |
| 159 | RQAPGPARDY | ++ |
| 160 | EVLGEEMYAY | ++ |
| 161 | EAAPDIMHY | ++ |
| 162 | IADNPQLSFY | ++++ |
| 163 | KIRAEVLSHY | ++ |
| 164 | KLAGTVFQY | ++ |
| 165 | VSVYNSYPY | ++ |
| 166 | YHRICELLSDY | ++++ |
| 167 | RAVQPGETY | +++ |
| 168 | VQPGETYTY | +++ |
| 169 | TVDNANILL | ++ |
| 170 | VQIAKGMNY | +++ |
| 171 | ITDFGLAKL | ++ |
| 172 | FSEPFHLIV | +++ |
| 173 | QSTTGVSHY | +++ |
| 174 | TSEVEGLAFVSY | +++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 175 | GLEYEAPKLY | ++ |
| 176 | HTDLESPSAVY | +++ |
| 177 | LVDGKWQEF | ++ |
| 178 | TQRTSFQFY | ++ |
| 179 | SSTDFTFASW | + |
| 180 | AQISDTGRY | ++ |
| 181 | SVTDLIGGKW | ++ |
| 182 | TQPELSSRY | ++ |
| 183 | LADTDLGMTF | ++ |
| 184 | KTIQEVAGY | ++ |
| 185 | NSDESADSEPHKY | ++++ |
| 186 | AVSSGLFFY | ++ |
| 187 | TQKSVQVLAY | ++ |
| 188 | DIPDYLLQY | +++ |
| 189 | FRGVFVHRY | ++ |
| 190 | VSSTVHNLY | ++++ |
| 191 | FTRAFDQLRM | +++ |
| 192 | LAFYYGMY | ++ |
| 193 | SQNGQLIHY | +++ |
| 194 | CYTADNEMGY | +++ |
| 195 | YTADNEMGYY | +++ |
| 196 | RLAQYTIERY | ++ |
| 197 | NDEIDKLTGY | ++++ |
| 198 | KLTDYINANY | ++ |
| 199 | LCAAVLAKY | ++ |
| 200 | SLPEFGLTY | ++ |
| 201 | SLPEFGLTYY | ++ |
| 202 | QTDINGGSLK | +++ |
| 203 | LSQDELSKF | ++ |
| 204 | NVKEAPTEY | ++ |
| 205 | RMQEGSEVY | ++ |
| 207 | LLEGEDAHLTQY | +++ |
| 208 | LLISKAEDY | ++ |
| 209 | EADPFLKYL | ++ |
| 210 | LLEADPFLKY | ++++ |
| 211 | YLNEWGSRF | ++ |
| 212 | MMTDLTSVY | +++ |
| 213 | VSDSTTEITY | +++ |
| 214 | VQDPSLPVY | ++ |
| 215 | DTLEAATSLY | ++ |
| 216 | NSMLDPLVY | ++++ |
| 217 | LMDEGAVLTL | ++ |
| 218 | FTAQLQLY | +++ |
| 219 | KTELETALYY | +++ |
| 220 | DVERIKDTY | ++ |
| 221 | TDVERIKDTY | +++ |
| 222 | GSPDAVVSY | + |
| 223 | NAVDVVPSSF | + |
| 224 | RTDEGDNRVW | ++ |
| 225 | STDPNIVRK | +++ |
| 226 | QITPKHNGLY | ++ |
| 227 | ESAPKEVSRY | ++ |
| 228 | KSFDDIAKY | ++ |
| 229 | MTDVFIDY | +++ |
| 230 | CVIETFHKY | +++ |
| 231 | LLPLLVMAY | ++ |
| 232 | RYLNIVHATQLY | ++ |
| 233 | RINSATGQY | ++ |
| 234 | YTDLTTIQV | ++++ |
| 235 | SIEIDHTQY | ++ |
| 236 | VLDSLLAQY | ++++ |
| 237 | AQEAAVFLTLY | +++ |
| 238 | ETDWGLLKGHTY | ++++ |
| 239 | SSERGSPIEKY | +++ |
| 240 | EVLDSLLAQY | ++ |
| 241 | SLMVASLTY | ++ |
| 242 | GTNLPTLLW | + |
| 243 | LTSEDTGAY | +++ |
| 244 | VTKYIAGPY | ++ |
| 245 | LSDNAANRY | +++ |
| 246 | ARLEGEIATY | ++ |
| 247 | SMIRVGTNY | ++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 248 | VTDIDELGK | +++ |
| 249 | GVGFTELEY | +++ |
| 250 | GYVCNACGLY | ++ |
| 251 | GIEMTYETY | ++ |
| 252 | DTTSHTYLQY | ++ |
| 253 | YLESHGLAY | ++++ |
| 254 | FLFNDALLY | ++++ |
| 255 | WELDSLEY | ++ |
| 256 | HAFESNNFIY | ++ |
| 257 | KSEMNVNMKY | ++++ |
| 258 | RPSSVLTIY | +++ |
| 259 | APDEVVALL | ++ |
| 260 | KPTEDSANVY | +++ |
| 261 | MTEGSTVNTEY | ++++ |
| 262 | NVKHFLNDLY | +++ |
| 263 | DCMDTEGSYM | ++ |
| 264 | YRDPVFVSL | ++ |
| 265 | LSDIDSRYI | ++ |
| 266 | LTDSFLLRF | ++++ |
| 267 | IVADDTVY | +++ |
| 268 | AILHHLYFY | + |
| 269 | LPSPAATIWDY | +++ |
| 270 | DLKIDLAAQY | ++ |
| 271 | VAEPPVVCSY | ++ |
| 272 | IPQDECLRY | +++ |
| 273 | CGPNEINHFY | ++ |
| 274 | YADIHGDLL | +++ |
| 275 | ESDEMENLLTY | +++ |
| 276 | QITSFASGTSY | +++ |
| 277 | LPAPGFLFY | ++ |
| 278 | AATVKSDIY | ++ |
| 279 | LMTVLLKY | +++ |
| 280 | TTEMVSNESVDY | ++++ |
| 281 | YPDLSELLM | ++ |
| 282 | QAMPSWPTAAY | ++ |
| 283 | ETILVSSSY | ++ |
| 284 | TCSHTFVYY | ++ |
| 285 | VLPHHSEGACVY | +++ |
| 286 | ATDMEGNLNY | +++ |
| 287 | ENSIEDLQY | +++ |
| 288 | TEEKFVSY | + |
| 289 | YTSHEDIGY | ++++ |
| 290 | GQFTGTAGACRY | ++ |
| 291 | TSDVTGSLTY | ++++ |
| 292 | VLDFAPPGASAY | ++++ |
| 294 | MMEMEGMY | +++ |
| 295 | GQRLDEAMISY | +++ |
| 296 | HMLAAMAY | ++ |
| 297 | RLDEAMISY | +++ |
| 298 | KFDVINHYF | ++ |
| 299 | EVDSVALSL | ++ |
| 300 | VSINPNSGDIY | +++ |
| 301 | ESQTCASDY | +++ |
| 302 | FYLSTPENYHY | +++ |
| 303 | GFGGLSSQGVYY | +++ |
| 304 | FSENLIYTYI | ++ |
| 305 | YADLLIYTY | ++++ |
| 306 | KSFETTVRY | ++ |
| 307 | DTDDRELRY | +++ |
| 308 | ELAAGQVVY | + |
| 309 | EVDRNLIQY | +++ |
| 310 | KAFQELGVRY | ++ |
| 311 | TVTDGTHTDFY | ++ |
| 312 | VTDGINPLI | ++ |
| 313 | VTDGTHTDFY | +++ |
| 314 | PPEANSLQGALY | ++ |
| 315 | VLKIELETY | +++ |
| 316 | YTCEECGQAF | ++ |
| 317 | EDLLEVLDMY | ++ |
| 318 | YMTSMALNY | +++ |
| 319 | FTDPHIITF | ++++ |
| 320 | QALQDKLQTFY | ++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 321 | DGIADASNLSYY | ++ |
| 322 | FSELNPLALY | ++++ |
| 323 | KTLQKPVLPLY | ++ |
| 324 | RTGIFPYRF | ++ |
| 325 | LQKPVLPLY | ++ |
| 326 | STSRLTLFS | ++ |
| 327 | IMLSVDQHLY | +++ |
| 328 | LLDEDNNIKL | ++ |
| 329 | NTDSMTLNNTAY | ++++ |
| 330 | EGELSEGEHWY | +++ |
| 331 | YLYQAPGSLALY | ++++ |
| 333 | LSDPQAELQFY | ++++ |
| 334 | PSSMPECLSY | ++++ |
| 335 | PSSMPECLSYY | +++ |
| 336 | ATNIQLNIDTY | +++ |
| 337 | FTESNQYNIY | ++++ |
| 338 | YSPDSFNVSW | ++ |
| 339 | ESMDIFPLGW | ++ |
| 340 | SVDSNLVAY | +++ |
| 341 | PANYLGKMTY | +++ |
| 342 | QTYMDGLLHY | ++++ |
| 343 | YFGNYFTYY | + |
| 344 | AVNALQSVY | ++ |
| 345 | NTMDAVPRIDHY | ++++ |
| 346 | VAGLEAGVLY | ++ |
| 347 | SADHPGLTF | ++ |
| 348 | DSTDGCLLSF | ++ |
| 349 | HLLSVSLYY | + |
| 350 | LTDPQVSYV | +++ |
| 351 | VLDPMLDFY | ++++ |
| 352 | YPVVVAESMY | ++ |
| 353 | RLNGSVASY | ++ |
| 354 | EIIRYIFAY | ++ |
| 355 | MADRGEARL | ++ |
| 356 | NSENHILKY | ++++ |
| 357 | MSPDIALLYL | +++ |
| 358 | YMSPDIALLY | ++++ |
| 359 | NKEINYFMY | +++ |
| 360 | RFDDINQEF | + |
| 361 | FTAEEGQLY | +++ |
| 362 | SGALDEAAAY | ++ |
| 363 | LTDRDVSFY | ++++ |
| 364 | DTGYLQLYY | ++++ |
| 365 | FVDTKVPEH | ++ |
| 366 | ITVDVRDEF | + |
| 367 | LTDTGYLQLY | ++++ |
| 368 | ESAATGQLDY | +++ |
| 369 | AVMEAAFVY | +++ |
| 370 | RLSTIRHLY | +++ |
| 371 | WSDSTSQTIY | ++++ |
| 372 | SRSDFEWVY | ++ |
| 373 | FHADSDDESF | + |
| 375 | ASSLDSLHY | ++++ |
| 376 | EDDEDEDLY | +++ |
| 377 | YADPSANRDLL | ++ |
| 378 | TAKAPSTEY | ++ |
| 379 | SLIIDDTEY | ++ |
| 380 | VACGNNPVY | +++ |
| 381 | ETSFSTSHY | ++++ |
| 382 | YEPATMEQY | ++ |
| 383 | PPDHAVGRTKY | ++ |
| 384 | RFRSITQSYY | + |
| 385 | SANALILTY | ++ |
| 386 | NSALNPLLY | ++++ |
| 387 | LMEKEDYHSLY | +++ |
| 388 | YTAHVGYSMY | ++++ |
| 389 | YYDLVESTF | + |
| 390 | FSEPFHLIVSY | ++++ |
| 391 | GSNPARYEF | ++ |
| 392 | TQHFVQENY | ++ |

TABLE 11-continued

MHC class I binding scores. Binding of HLA-class I restricted peptides to HLA-A*01:01 was ranged by peptide exchange yield: >10% = +; >20% = ++; >50 = +++; >75% = ++++

| SEQID | Sequence | Peptide exchange |
|---|---|---|
| 393 | QVWGGQPVY | + |
| 394 | QVPLDCVLY | ++ |
| 395 | ILKGGSGTY | ++ |
| 396 | LPDPNVQKY | ++ |
| 397 | NSAINPLIY | ++++ |
| 398 | YYYDTHTNTY | + |

REFERENCE LIST

Alcoser, S. Y. et al., BMC Biotechnol. 11 (2011): 124
Allison, J. P. et al., Science. 270 (1995): 932-933
Andersen, R. S. et al., Nat Protoc. 7 (2012): 891-902
Anderson, N. L. et al., J Proteome Res. 11 (2012): 1868-1878
Appay, V. et al., Eur J Immunol. 36 (2006): 1805-1814
Banchereau, J. et al., Cell. 106 (2001): 271-274
Beatty, G. et al., J Immunol. 166 (2001): 2276-2282
Beggs, J. D., Nature. 275 (1978): 104-109
Benjamini, Y. et al., Journal of the Royal Statistical Society Series B (Methodological). Vol. 57 (1995): 289-300
Boulter, J. M. et al., Protein Eng. 16 (2003): 707-711
Braumuller, H. et al., Nature. (2013)
Bray, F. et al., Int J Cancer. 132 (2013): 1133-1145
Brossart, P. et al., Blood. 90 (1997): 1594-1599
Bruckdorfer, T. et al., Curr Pharm Biotechnol. 5 (2004): 29-43
Card, K. F. et al., Cancer Immunol Immunother. 53 (2004): 345-357
Cohen, C. J. et al., J Mol Recognit. 16 (2003a): 324-332
Cohen, C. J. et al., J Immunol. 170 (2003b): 4349-4361
Cohen, S. N. et al., Proc Natl Acad Sci USA. 69 (1972): 2110-2114
Coligan, J. E. et al., Current Protocols in Protein Science. (1995)
Colombetti, S. et al., J Immunol. 176 (2006): 2730-2738
Dengjel, J. et al., Clin Cancer Res. 12 (2006): 4163-4170
Denkberg, G. et al., J Immunol. 171 (2003): 2197-2207
Falk, K. et al., Nature. 351 (1991): 290-296
Ferlay et al., GLOBOCAN 2012 v1 0, Cancer Incidence and Mortality Worldwide: IARC CancerBase No 11 [Internet] (2013), http://globocan.iarc.fr
Follenzi, A. et al., Nat Genet. 25 (2000): 217-222
Fong, L. et al., Proc Natl Acad Sci USA. 98 (2001): 8809-8814
Forsey, R. W. et al., Biotechnol Lett. 31 (2009): 819-823
Gabrilovich, D. I. et al., Nat Med. 2 (1996): 1096-1103
Gattinoni, L. et al., Nat Rev Immunol. 6 (2006): 383-393
Gnjatic, S. et al., Proc Natl Acad Sci USA. 100 (2003): 8862-8867
Godkin, A. et al., Int Immunol. 9 (1997): 905-911
Gragert, L. et al., Hum Immunol. 74 (2013): 1313-1320
Green, M. R. et al., Molecular Cloning, A Laboratory Manual. 4th (2012)
Greenfield, E. A., Antibodies: A Laboratory Manual. 2nd (2014)
Gunawardana, C. et al., Br J Haematol. 142 (2008): 606-609
Gustafsson, C. et al., Trends Biotechnol. 22 (2004): 346-353
Hwang, M. L. et al., J Immunol. 179 (2007): 5829-5838
Jung, G. et al., Proc Natl Acad Sci USA. 84 (1987): 4611-4615
Kibbe, A. H., Handbook of Pharmaceutical Excipients. rd (2000)
Krieg, A. M., Nat Rev Drug Discov. 5 (2006): 471-484
Kuball, J. et al., Blood. 109 (2007): 2331-2338
Liddy, N. et al., Nat Med. 18 (2012): 980-987
Ljunggren, H. G. et al., J Exp Med. 162 (1985): 1745-1759
Longenecker, B. M. et al., Ann N Y Acad Sci. 690 (1993): 276-291
Lonsdale, J., Nat Genet. 45 (2013): 580-585
Lukas, T. J. et al., Proc Natl Acad Sci USA. 78 (1981): 2791-2795
Lundblad, R. L., Chemical Reagents for Protein Modification. 3rd (2004)
Meziere, C. et al., J Immunol. 159 (1997): 3230-3237
Molina, J. R. et al., Mayo Clin Proc. 83 (2008): 584-594
Morgan, R. A. et al., Science. 314 (2006): 126-129
Mortara, L. et al., Clin Cancer Res. 12 (2006): 3435-3443
Mueller, L. N. et al., J Proteome Res. 7 (2008): 51-61
Mueller, L. N. et al., Proteomics. 7 (2007): 3470-3480
Mumberg, D. et al., Proc Natl Acad Sci USA. 96 (1999): 8633-8638
Pinheiro, J. et al., nlme: Linear and Nonlinear Mixed Effects Models (http://CRANR-projectorg/package=nlme) (2015)
Plebanski, M. et al., Eur J Immunol. 25 (1995): 1783-1787
Porta, C. et al., Virology. 202 (1994): 949-955
Rammensee, H. et al., Immunogenetics. 50 (1999): 213-219
Rini, B. I. et al., Cancer. 107 (2006): 67-74
Rock, K. L. et al., Science. 249 (1990): 918-921
Rodenko, B. et al., Nat Protoc. 1 (2006): 1120-1132
Saiki, R. K. et al., Science. 239 (1988): 487-491
Schmitt, T. M. et al., Hum Gene Ther. 20 (2009): 1240-1248
Scholten, K. B. et al., Clin Immunol. 119 (2006): 135-145
Seeger, F. H. et al., Immunogenetics. 49 (1999): 571-576
Sherman, F. et al., Laboratory Course Manual for Methods in Yeast Genetics. (1986)
Silva, L. P. et al., Anal Chem. 85 (2013): 9536-9542
Singh-Jasuja, H. et al., Cancer Immunol Immunother. 53 (2004): 187-195
Small, E. J. et al., J Clin Oncol. 24 (2006): 3089-3094
Sturm, M. et al., BMC Bioinformatics. 9 (2008): 163
Teufel, R. et al., Cell Mol Life Sci. 62 (2005): 1755-1762
Thakkar, J. P. et al., Cancer Epidemiol Biomarkers Prev. 23 (2014): 1985-1996
Tran, T. T. et al., Photochem Photobiol. 90 (2014): 1136-1143
Walter, S. et al., J Immunol. 171 (2003): 4974-4978
Walter, S. et al., Nat Med. 18 (2012): 1254-1261
Willcox, B. E. et al., Protein Sci. 8 (1999): 2418-2423
World Cancer Report (2014)
Zaremba, S. et al., Cancer Res. 57 (1997): 4570-4577
Zufferey, R. et al., J Virol. 73 (1999): 2886-2892

The invention claimed is:

1. A method of treating a patient who has cancer overexpressing CAPN6 polypeptide comprising the amino acid sequence of SEQ ID NO: 70, comprising administering to said patient a population of activated T cells that kill the cancer cells,
   wherein the activated T cells are cytotoxic T cells produced by contacting CD8+ T cells with an antigen presenting cell that presents a peptide consisting of the amino acid sequence of SEQ ID NO: 70 in a complex with an MHC class I molecule on the surface of the antigen presenting cell in vitro, for a period of time sufficient to activate said T cell,
   wherein said cancer is selected from breast cancer, cholangiocellular carcinoma, colorectal cancer, gastric cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, and uterine and endometrial cancer.

2. The method of claim 1, wherein the T cells are autologous to the patient.

3. The method of claim 1, wherein the T cells are obtained from tumor infiltrating lymphocytes or peripheral blood mononuclear cells.

4. The method of claim 1, further comprising administering to said patient an adjuvant selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

5. The method of claim 4, wherein the adjuvant is IL-7.

6. The method of claim 1, wherein the cancer is breast cancer.

7. The method of claim 1, wherein the cancer is cholangiocellular carcinoma.

8. The method of claim 1, wherein the cancer is colorectal cancer.

9. The method of claim 1, wherein the cancer is gastric cancer.

10. The method of claim 1, wherein the cancer is hepatocellular carcinoma.

11. The method of claim 1, wherein the cancer is head and neck squamous cell carcinoma.

12. The method of claim 1, wherein the cancer is melanoma.

13. The method of claim 1, wherein the cancer is non-Hodgkin lymphoma.

14. The method of claim 1, wherein the cancer is non-small cell lung cancer.

15. The method of claim 1, wherein the cancer is ovarian cancer.

16. The method of claim 1, wherein the cancer is esophageal cancer.

17. The method of claim 1, wherein the cancer is pancreatic cancer.

18. The method of claim 1, wherein the cancer is prostate cancer.

19. The method of claim 1, wherein the cancer is renal cell carcinoma.

20. The method of claim 1, wherein the cancer is uterine and endometrial cancer.

* * * * *

SEQUENCE LISTING

<160> NUMBER OF SEQ ID NOS: 434

<210> SEQ ID NO 1
<211> LENGTH: 9
<212> TYPE: PRT
<213> ORGANISM: Homo sapiens

<400> SEQUENCE: 1

Thr Leu Asp Ser Thr Arg Thr Leu Tyr
1               5

<210> SEQ ID NO 2
<211> LENGTH: 8
<212> TYPE: PRT
<213> ORGANISM: Homo sapiens

<400> SEQUENCE: 2

Val Asp Pro Ile Gly His Leu Tyr
1               5

<210> SEQ ID NO 3
<211> LENGTH: 10
<212> TYPE: PRT
<213> ORGANISM: Homo sapiens

<400> SEQUENCE: 3

Phe Gly Thr Thr Pro Ala Ala Glu Tyr Phe
1               5                   10

<210> SEQ ID NO 4
<211> LENGTH: 9
<212> TYPE: PRT
<213> ORGANISM: Homo sapiens

<400> SEQUENCE: 4

Arg Ile Glu Ala Ile Arg Ala Glu Tyr
1               5

<210> SEQ ID NO 5
<211> LENGTH: 11
<212> TYPE: PRT
<213> ORGANISM: Homo sapiens

<400> SEQUENCE: 5

Phe Met Val Ile Ala Gly Met Pro Leu Phe Tyr
1               5                   10

<210> SEQ ID NO 6
<211> LENGTH: 9
<212> TYPE: PRT
<213> ORGANISM: Homo sapiens

<400> SEQUENCE: 6

Ala Arg Asp Pro Ile Thr Phe Ser Phe
1               5

<210> SEQ ID NO 7
<211> LENGTH: 12
<212> TYPE: PRT
<213> ORGANISM: Homo sapiens

<400> SEQUENCE: 7

Ala Ser Asp Asp Val Arg Ile Glu Val Gly Leu Tyr
1               5                   10

```
<210> SEQ ID NO 8
<211> LENGTH: 10
<212> TYPE: PRT
<213> ORGANISM: Homo sapiens

<400> SEQUENCE: 8

Thr Ser Arg Ala Ala Asn Ile Pro Gly Tyr
1               5                   10

<210> SEQ ID NO 9
<211> LENGTH: 9
<212> TYPE: PRT
<213> ORGANISM: Homo sapiens

<400> SEQUENCE: 9

Gln Leu Asp Ser Thr Leu Asp Ser Tyr
1               5

<210> SEQ ID NO 10
<211> LENGTH: 9
<212> TYPE: PRT
<213> ORGANISM: Homo sapiens

<400> SEQUENCE: 10

Val Ser Glu Arg Thr Gly Ile Ser Tyr
1               5

<210> SEQ ID NO 11
<211> LENGTH: 9
<212> TYPE: PRT
<213> ORGANISM: Homo sapiens

<400> SEQUENCE: 11

Ala Ser Asp His Trp Arg Gly Arg Tyr
1               5

<210> SEQ ID NO 12
<211> LENGTH: 10
<212> TYPE: PRT
<213> ORGANISM: Homo sapiens

<400> SEQUENCE: 12

Tyr Thr Asp Phe Val Gly Glu Gly Leu Tyr
1               5                   10

<210> SEQ ID NO 13
<211> LENGTH: 9
<212> TYPE: PRT
<213> ORGANISM: Homo sapiens

<400> SEQUENCE: 13

Asn Thr His Thr Gly Thr Arg Pro Tyr
1               5

<210> SEQ ID NO 14
<211> LENGTH: 10
<212> TYPE: PRT
<213> ORGANISM: Homo sapiens

<400> SEQUENCE: 14

Gln Ser Glu Lys Glu Pro Gly Gln Gln Tyr
1               5                   10

<210> SEQ ID NO 15
```

```
<211> LENGTH: 10
<212> TYPE: PRT
<213> ORGANISM: Homo sapiens

<400> SEQUENCE: 15

Tyr Leu Asp Ser Ser Lys Pro Ala Val Tyr
1               5                   10

<210> SEQ ID NO 16
<211> LENGTH: 9
<212> TYPE: PRT
<213> ORGANISM: Homo sapiens

<400> SEQUENCE: 16

Asn Ser Asp Ile Ser Ile Pro Glu Tyr
1               5

<210> SEQ ID NO 17
<211> LENGTH: 9
<212> TYPE: PRT
<213> ORGANISM: Homo sapiens

<400> SEQUENCE: 17

Ala Ser Trp Ala Val Leu Cys Tyr Tyr
1               5

<210> SEQ ID NO 18
<211> LENGTH: 9
<212> TYPE: PRT
<213> ORGANISM: Homo sapiens

<400> SEQUENCE: 18

Arg Ser Asp Pro Val Ser Leu Arg Tyr
1               5

<210> SEQ ID NO 19
<211> LENGTH: 9
<212> TYPE: PRT
<213> ORGANISM: Homo sapiens

<400> SEQUENCE: 19

Leu Thr Glu Gly His Ser Gly Asn Tyr
1               5

<210> SEQ ID NO 20
<211> LENGTH: 9
<212> TYPE: PRT
<213> ORGANISM: Homo sapiens

<400> SEQUENCE: 20

Leu Ser Ala Gln His Arg Met Leu Ala
1               5

<210> SEQ ID NO 21
<211> LENGTH: 10
<212> TYPE: PRT
<213> ORGANISM: Homo sapiens

<400> SEQUENCE: 21

Leu Ser Ser Ala Val Asn Pro Ile Ile Tyr
1               5                   10

<210> SEQ ID NO 22
<211> LENGTH: 9
<212> TYPE: PRT
```

```
<213> ORGANISM: Homo sapiens

<400> SEQUENCE: 22

Val Met Asp Thr Leu Gly Leu Phe Tyr
1               5

<210> SEQ ID NO 23
<211> LENGTH: 10
<212> TYPE: PRT
<213> ORGANISM: Homo sapiens

<400> SEQUENCE: 23

Asp Thr Asp Pro Leu Lys Ala Ala Gly Leu
1               5                   10

<210> SEQ ID NO 24
<211> LENGTH: 9
<212> TYPE: PRT
<213> ORGANISM: Homo sapiens

<400> SEQUENCE: 24

Asn Leu Asp His Tyr Thr Asn Ala Tyr
1               5

<210> SEQ ID NO 25
<211> LENGTH: 10
<212> TYPE: PRT
<213> ORGANISM: Homo sapiens

<400> SEQUENCE: 25

Ala Met Met Gln Glu Ala Gln Leu Ala Tyr
1               5                   10

<210> SEQ ID NO 26
<211> LENGTH: 9
<212> TYPE: PRT
<213> ORGANISM: Homo sapiens

<400> SEQUENCE: 26

Ala Ser Asp Asp Phe Arg Ser Lys Tyr
1               5

<210> SEQ ID NO 27
<211> LENGTH: 10
<212> TYPE: PRT
<213> ORGANISM: Homo sapiens

<400> SEQUENCE: 27

Pro Ser Glu Val Pro Val Asp Ser His Tyr
1               5                   10

<210> SEQ ID NO 28
<211> LENGTH: 11
<212> TYPE: PRT
<213> ORGANISM: Homo sapiens

<400> SEQUENCE: 28

Pro Ser Glu Val Pro Val Asp Ser His Tyr Tyr
1               5                   10

<210> SEQ ID NO 29
<211> LENGTH: 11
<212> TYPE: PRT
<213> ORGANISM: Homo sapiens
```

<400> SEQUENCE: 29

Thr Leu Glu Asp Leu Asp Asn Leu Tyr Asn Tyr
1               5                   10

<210> SEQ ID NO 30
<211> LENGTH: 9
<212> TYPE: PRT
<213> ORGANISM: Homo sapiens

<400> SEQUENCE: 30

Val Thr Thr Asp Lys Pro Arg Ala Tyr
1               5

<210> SEQ ID NO 31
<211> LENGTH: 13
<212> TYPE: PRT
<213> ORGANISM: Homo sapiens

<400> SEQUENCE: 31

Val Ser Asp His Leu Gln Ala Gly Met Leu Gly Gln Tyr
1               5                   10

<210> SEQ ID NO 32
<211> LENGTH: 11
<212> TYPE: PRT
<213> ORGANISM: Homo sapiens

<400> SEQUENCE: 32

Gly Thr Asp Lys Gln Asn Ser Thr Leu Arg Tyr
1               5                   10

<210> SEQ ID NO 33
<211> LENGTH: 10
<212> TYPE: PRT
<213> ORGANISM: Homo sapiens

<400> SEQUENCE: 33

Ser Met Asp Pro Val Thr Gly Tyr Gln Tyr
1               5                   10

<210> SEQ ID NO 34
<211> LENGTH: 11
<212> TYPE: PRT
<213> ORGANISM: Homo sapiens

<400> SEQUENCE: 34

Ser Ser Trp Ser Ala Gly Glu Asn Asp Ser Tyr
1               5                   10

<210> SEQ ID NO 35
<211> LENGTH: 11
<212> TYPE: PRT
<213> ORGANISM: Homo sapiens

<400> SEQUENCE: 35

Ser Trp Ser Ala Gly Glu Asn Asp Ser Tyr Ser
1               5                   10

<210> SEQ ID NO 36
<211> LENGTH: 9
<212> TYPE: PRT
<213> ORGANISM: Homo sapiens

<400> SEQUENCE: 36

```
Met Thr Ser Thr Glu Gln Ser Leu Tyr
1               5

<210> SEQ ID NO 37
<211> LENGTH: 10
<212> TYPE: PRT
<213> ORGANISM: Homo sapiens

<400> SEQUENCE: 37

Met Thr Ser Thr Glu Gln Ser Leu Tyr Tyr
1               5                   10

<210> SEQ ID NO 38
<211> LENGTH: 11
<212> TYPE: PRT
<213> ORGANISM: Homo sapiens

<400> SEQUENCE: 38

Lys Ser Trp Ser Gln Ser Ser Ser Leu Met Tyr
1               5                   10

<210> SEQ ID NO 39
<211> LENGTH: 9
<212> TYPE: PRT
<213> ORGANISM: Homo sapiens

<400> SEQUENCE: 39

Trp Ser Gln Ser Ser Ser Leu Met Tyr
1               5

<210> SEQ ID NO 40
<211> LENGTH: 9
<212> TYPE: PRT
<213> ORGANISM: Homo sapiens

<400> SEQUENCE: 40

Thr Ser Asp Gln Leu Gly Tyr Ser Tyr
1               5

<210> SEQ ID NO 41
<211> LENGTH: 10
<212> TYPE: PRT
<213> ORGANISM: Homo sapiens

<400> SEQUENCE: 41

His Ser Asp Leu Leu Glu Asp Ser Lys Tyr
1               5                   10

<210> SEQ ID NO 42
<211> LENGTH: 9
<212> TYPE: PRT
<213> ORGANISM: Homo sapiens

<400> SEQUENCE: 42

Ala Ser Asp Val Asp Thr Leu Leu Lys
1               5

<210> SEQ ID NO 43
<211> LENGTH: 11
<212> TYPE: PRT
<213> ORGANISM: Homo sapiens

<400> SEQUENCE: 43

Glu Thr Glu Pro Glu Arg His Leu Gly Ser Tyr
1               5                   10
```

```
<210> SEQ ID NO 44
<211> LENGTH: 9
<212> TYPE: PRT
<213> ORGANISM: Homo sapiens

<400> SEQUENCE: 44

Ile Pro Ser Phe Asn Glu Met Val Tyr
1               5

<210> SEQ ID NO 45
<211> LENGTH: 8
<212> TYPE: PRT
<213> ORGANISM: Homo sapiens

<400> SEQUENCE: 45

Asn Leu Asp Pro Asn Lys Ile Tyr
1               5

<210> SEQ ID NO 46
<211> LENGTH: 14
<212> TYPE: PRT
<213> ORGANISM: Homo sapiens

<400> SEQUENCE: 46

Arg Ser Asp Pro Gly Gly Gly Gly Leu Ala Tyr Ala Ala Tyr
1               5                   10

<210> SEQ ID NO 47
<211> LENGTH: 9
<212> TYPE: PRT
<213> ORGANISM: Homo sapiens

<400> SEQUENCE: 47

Trp Ser Asp Gly Val Pro Leu Leu Tyr
1               5

<210> SEQ ID NO 48
<211> LENGTH: 10
<212> TYPE: PRT
<213> ORGANISM: Homo sapiens

<400> SEQUENCE: 48

Phe Thr Thr Gln Asp Glu Leu Leu Val Tyr
1               5                   10

<210> SEQ ID NO 49
<211> LENGTH: 9
<212> TYPE: PRT
<213> ORGANISM: Homo sapiens

<400> SEQUENCE: 49

Gly Ser Phe Ser Ile Gln His Thr Tyr
1               5

<210> SEQ ID NO 50
<211> LENGTH: 11
<212> TYPE: PRT
<213> ORGANISM: Homo sapiens

<400> SEQUENCE: 50

Ile Thr Asp Glu Asp Glu Asp Met Leu Ser Tyr
1               5                   10
```

```
<210> SEQ ID NO 51
<211> LENGTH: 9
<212> TYPE: PRT
<213> ORGANISM: Homo sapiens

<400> SEQUENCE: 51

Ser Thr Glu Glu Arg Arg Leu Asn Tyr
1               5

<210> SEQ ID NO 52
<211> LENGTH: 9
<212> TYPE: PRT
<213> ORGANISM: Homo sapiens

<400> SEQUENCE: 52

Thr Thr Gln Asp Glu Leu Leu Val Tyr
1               5

<210> SEQ ID NO 53
<211> LENGTH: 11
<212> TYPE: PRT
<213> ORGANISM: Homo sapiens

<400> SEQUENCE: 53

Tyr Leu Glu Asp Arg Pro Leu Ser Gln Leu Tyr
1               5                   10

<210> SEQ ID NO 54
<211> LENGTH: 9
<212> TYPE: PRT
<213> ORGANISM: Homo sapiens

<400> SEQUENCE: 54

Glu Val Asp Ile His Thr Ile His Tyr
1               5

<210> SEQ ID NO 55
<211> LENGTH: 9
<212> TYPE: PRT
<213> ORGANISM: Homo sapiens

<400> SEQUENCE: 55

Ala Thr Glu Gly Asp Val Leu Asn Tyr
1               5

<210> SEQ ID NO 56
<211> LENGTH: 11
<212> TYPE: PRT
<213> ORGANISM: Homo sapiens

<400> SEQUENCE: 56

Val Thr Glu Tyr Ala Glu Glu Ile Tyr Gln Tyr
1               5                   10

<210> SEQ ID NO 57
<211> LENGTH: 11
<212> TYPE: PRT
<213> ORGANISM: Homo sapiens

<400> SEQUENCE: 57

Ala Ser Asp Pro Ala Ser Ser Thr Ser Cys Tyr
1               5                   10

<210> SEQ ID NO 58
<211> LENGTH: 9
```

```
<212> TYPE: PRT
<213> ORGANISM: Homo sapiens

<400> SEQUENCE: 58

Tyr Leu Glu Asn Ser Ala Ser Trp Tyr
1               5

<210> SEQ ID NO 59
<211> LENGTH: 10
<212> TYPE: PRT
<213> ORGANISM: Homo sapiens

<400> SEQUENCE: 59

Phe Thr Asp Ser Gln Gly Asn Asp Ile Lys
1               5                   10

<210> SEQ ID NO 60
<211> LENGTH: 9
<212> TYPE: PRT
<213> ORGANISM: Homo sapiens

<400> SEQUENCE: 60

Met Thr Glu Lys Phe Leu Phe Leu Tyr
1               5

<210> SEQ ID NO 61
<211> LENGTH: 12
<212> TYPE: PRT
<213> ORGANISM: Homo sapiens

<400> SEQUENCE: 61

Ser Ser Asp Ile Val Ala Leu Gly Gly Phe Leu Tyr
1               5                   10

<210> SEQ ID NO 62
<211> LENGTH: 10
<212> TYPE: PRT
<213> ORGANISM: Homo sapiens

<400> SEQUENCE: 62

Val Ser Glu Leu Val Thr Thr Gly His Tyr
1               5                   10

<210> SEQ ID NO 63
<211> LENGTH: 11
<212> TYPE: PRT
<213> ORGANISM: Homo sapiens

<400> SEQUENCE: 63

Thr Ser Glu Ile Ser Gln Asn Ala Leu Met Tyr
1               5                   10

<210> SEQ ID NO 64
<211> LENGTH: 12
<212> TYPE: PRT
<213> ORGANISM: Homo sapiens

<400> SEQUENCE: 64

Thr Ser Glu Ile Ser Gln Asn Ala Leu Met Tyr Tyr
1               5                   10

<210> SEQ ID NO 65
<211> LENGTH: 9
<212> TYPE: PRT
<213> ORGANISM: Homo sapiens
```

<400> SEQUENCE: 65

Ser Ser Asp Phe Asp Pro Leu Val Tyr
1               5

<210> SEQ ID NO 66
<211> LENGTH: 9
<212> TYPE: PRT
<213> ORGANISM: Homo sapiens

<400> SEQUENCE: 66

Ile Ala Thr Val Ile Gln Leu Phe Tyr
1               5

<210> SEQ ID NO 67
<211> LENGTH: 9
<212> TYPE: PRT
<213> ORGANISM: Homo sapiens

<400> SEQUENCE: 67

Asn Val Asp Gln Asn Gln Asn Ser Tyr
1               5

<210> SEQ ID NO 68
<211> LENGTH: 10
<212> TYPE: PRT
<213> ORGANISM: Homo sapiens

<400> SEQUENCE: 68

Gln Ser Leu Pro Glu Phe Gly Leu Thr Tyr
1               5                   10

<210> SEQ ID NO 69
<211> LENGTH: 11
<212> TYPE: PRT
<213> ORGANISM: Homo sapiens

<400> SEQUENCE: 69

Gln Ser Leu Pro Glu Phe Gly Leu Thr Tyr Tyr
1               5                   10

<210> SEQ ID NO 70
<211> LENGTH: 9
<212> TYPE: PRT
<213> ORGANISM: Homo sapiens

<400> SEQUENCE: 70

Tyr Thr Glu Leu Val Glu Glu Lys Tyr
1               5

<210> SEQ ID NO 71
<211> LENGTH: 10
<212> TYPE: PRT
<213> ORGANISM: Homo sapiens

<400> SEQUENCE: 71

Leu Thr Asp Ser Thr Thr Arg Thr Thr Tyr
1               5                   10

<210> SEQ ID NO 72
<211> LENGTH: 10
<212> TYPE: PRT
<213> ORGANISM: Homo sapiens

<400> SEQUENCE: 72

Val Thr Asp Ser Thr Thr Lys Ile Ala Tyr
1               5                   10

<210> SEQ ID NO 73
<211> LENGTH: 8
<212> TYPE: PRT
<213> ORGANISM: Homo sapiens

<400> SEQUENCE: 73

Ser Thr Asp Ser Ala Ser Tyr Tyr
1               5

<210> SEQ ID NO 74
<211> LENGTH: 9
<212> TYPE: PRT
<213> ORGANISM: Homo sapiens

<400> SEQUENCE: 74

Glu Met Glu Gln Gln Ser Gln Glu Tyr
1               5

<210> SEQ ID NO 75
<211> LENGTH: 9
<212> TYPE: PRT
<213> ORGANISM: Homo sapiens

<400> SEQUENCE: 75

Phe Thr Asp Tyr Glu Leu Lys Ala Tyr
1               5

<210> SEQ ID NO 76
<211> LENGTH: 11
<212> TYPE: PRT
<213> ORGANISM: Homo sapiens

<400> SEQUENCE: 76

Gln Thr Asp Val Glu Arg Ile Lys Asp Thr Tyr
1               5                   10

<210> SEQ ID NO 77
<211> LENGTH: 9
<212> TYPE: PRT
<213> ORGANISM: Homo sapiens

<400> SEQUENCE: 77

Phe Thr Ser Asp Thr Gly Leu Glu Tyr
1               5

<210> SEQ ID NO 78
<211> LENGTH: 10
<212> TYPE: PRT
<213> ORGANISM: Homo sapiens

<400> SEQUENCE: 78

Gln Leu Asp Ser Ala Val Lys Asn Leu Tyr
1               5                   10

<210> SEQ ID NO 79
<211> LENGTH: 12
<212> TYPE: PRT
<213> ORGANISM: Homo sapiens

<400> SEQUENCE: 79

Ala Ser Asp Leu Glu Pro Arg Glu Leu Leu Ser Tyr

-continued

```
1               5                   10
```

<210> SEQ ID NO 80
<211> LENGTH: 11
<212> TYPE: PRT
<213> ORGANISM: Homo sapiens

<400> SEQUENCE: 80

```
Glu Leu Cys Pro Leu Pro Gly Thr Ser Ala Tyr
1               5                   10
```

<210> SEQ ID NO 81
<211> LENGTH: 10
<212> TYPE: PRT
<213> ORGANISM: Homo sapiens

<400> SEQUENCE: 81

```
Tyr Ser Asp Leu His Thr Pro Gly Arg Tyr
1               5                   10
```

<210> SEQ ID NO 82
<211> LENGTH: 9
<212> TYPE: PRT
<213> ORGANISM: Homo sapiens

<400> SEQUENCE: 82

```
Leu Thr Glu Lys Ser His Ile Arg Tyr
1               5
```

<210> SEQ ID NO 83
<211> LENGTH: 10
<212> TYPE: PRT
<213> ORGANISM: Homo sapiens

<400> SEQUENCE: 83

```
Asp Thr Glu Phe His Gly Gly Leu His Tyr
1               5                   10
```

<210> SEQ ID NO 84
<211> LENGTH: 11
<212> TYPE: PRT
<213> ORGANISM: Homo sapiens

<400> SEQUENCE: 84

```
Glu Ser Glu Met Ile Lys Phe Ala Ser Tyr Tyr
1               5                   10
```

<210> SEQ ID NO 85
<211> LENGTH: 10
<212> TYPE: PRT
<213> ORGANISM: Homo sapiens

<400> SEQUENCE: 85

```
Ser Ser Asp Asn Tyr Glu His Trp Leu Tyr
1               5                   10
```

<210> SEQ ID NO 86
<211> LENGTH: 8
<212> TYPE: PRT
<213> ORGANISM: Homo sapiens

<400> SEQUENCE: 86

```
Val Asp Pro Ala Ser Asn Thr Tyr
1               5
```

```
<210> SEQ ID NO 87
<211> LENGTH: 9
<212> TYPE: PRT
<213> ORGANISM: Homo sapiens

<400> SEQUENCE: 87

Ala Phe Asp Asp Ile Ala Thr Tyr Phe
1               5

<210> SEQ ID NO 88
<211> LENGTH: 11
<212> TYPE: PRT
<213> ORGANISM: Homo sapiens

<400> SEQUENCE: 88

Lys Glu Val Asp Pro Ala Gly His Ser Tyr Ile
1               5                   10

<210> SEQ ID NO 89
<211> LENGTH: 11
<212> TYPE: PRT
<213> ORGANISM: Homo sapiens

<400> SEQUENCE: 89

Glu Val Tyr Asp Gly Arg Glu His Ser Ala Tyr
1               5                   10

<210> SEQ ID NO 90
<211> LENGTH: 9
<212> TYPE: PRT
<213> ORGANISM: Homo sapiens

<400> SEQUENCE: 90

Tyr Glu Asp His Phe Pro Leu Leu Phe
1               5

<210> SEQ ID NO 91
<211> LENGTH: 10
<212> TYPE: PRT
<213> ORGANISM: Homo sapiens

<400> SEQUENCE: 91

Cys Leu Val Leu Val Ile Val Leu Leu Tyr
1               5                   10

<210> SEQ ID NO 92
<211> LENGTH: 12
<212> TYPE: PRT
<213> ORGANISM: Homo sapiens

<400> SEQUENCE: 92

Thr Thr Asp Asp Thr Thr Ala Met Ala Ser Ala Ser
1               5                   10

<210> SEQ ID NO 93
<211> LENGTH: 9
<212> TYPE: PRT
<213> ORGANISM: Homo sapiens

<400> SEQUENCE: 93

His Leu Lys Ile Leu Ser Pro Ile Tyr
1               5

<210> SEQ ID NO 94
```

```
<211> LENGTH: 10
<212> TYPE: PRT
<213> ORGANISM: Homo sapiens

<400> SEQUENCE: 94

Lys Pro Ser Ala Val Lys Asp Ser Ile Tyr
1               5                   10

<210> SEQ ID NO 95
<211> LENGTH: 9
<212> TYPE: PRT
<213> ORGANISM: Homo sapiens

<400> SEQUENCE: 95

Ser Ser Asp Pro Lys Ala Val Met Phe
1               5

<210> SEQ ID NO 96
<211> LENGTH: 9
<212> TYPE: PRT
<213> ORGANISM: Homo sapiens

<400> SEQUENCE: 96

Thr Ala Thr Leu Leu Ile Val Arg Tyr
1               5

<210> SEQ ID NO 97
<211> LENGTH: 10
<212> TYPE: PRT
<213> ORGANISM: Homo sapiens

<400> SEQUENCE: 97

Phe Pro Ala Pro Pro Ala His Trp Phe Tyr
1               5                   10

<210> SEQ ID NO 98
<211> LENGTH: 9
<212> TYPE: PRT
<213> ORGANISM: Homo sapiens

<400> SEQUENCE: 98

Asn Phe Ser Asp Leu Val Phe Thr Tyr
1               5

<210> SEQ ID NO 99
<211> LENGTH: 9
<212> TYPE: PRT
<213> ORGANISM: Homo sapiens

<400> SEQUENCE: 99

Ala Ala Asp Ser Asn Pro Ser Glu Leu
1               5

<210> SEQ ID NO 100
<211> LENGTH: 11
<212> TYPE: PRT
<213> ORGANISM: Homo sapiens

<400> SEQUENCE: 100

Thr Thr Ser Ser Ala Ile Ser Trp Ile Leu Tyr
1               5                   10

<210> SEQ ID NO 101
<211> LENGTH: 9
<212> TYPE: PRT
```

<213> ORGANISM: Homo sapiens

<400> SEQUENCE: 101

Ser Ile Thr Asp Val Asp Phe Ile Tyr
1               5

<210> SEQ ID NO 102
<211> LENGTH: 9
<212> TYPE: PRT
<213> ORGANISM: Homo sapiens

<400> SEQUENCE: 102

Ser Thr Ile Arg Gly Glu Leu Phe Phe
1               5

<210> SEQ ID NO 103
<211> LENGTH: 9
<212> TYPE: PRT
<213> ORGANISM: Homo sapiens

<400> SEQUENCE: 103

Ile Thr Asp Thr Leu Ile His Leu Met
1               5

<210> SEQ ID NO 104
<211> LENGTH: 8
<212> TYPE: PRT
<213> ORGANISM: Homo sapiens

<400> SEQUENCE: 104

Ile Thr Asp Thr Leu Ile His Leu
1               5

<210> SEQ ID NO 105
<211> LENGTH: 11
<212> TYPE: PRT
<213> ORGANISM: Homo sapiens

<400> SEQUENCE: 105

Val Val Phe Asp Lys Ser Asp Leu Ala Lys Tyr
1               5                   10

<210> SEQ ID NO 106
<211> LENGTH: 12
<212> TYPE: PRT
<213> ORGANISM: Homo sapiens

<400> SEQUENCE: 106

Glu Val Val Glu Gly Lys Glu Trp Gly Ser Phe Tyr
1               5                   10

<210> SEQ ID NO 107
<211> LENGTH: 9
<212> TYPE: PRT
<213> ORGANISM: Homo sapiens

<400> SEQUENCE: 107

Thr Thr Glu Asn Ser Gly Asn Tyr Tyr
1               5

<210> SEQ ID NO 108
<211> LENGTH: 9
<212> TYPE: PRT
<213> ORGANISM: Homo sapiens

```
<400> SEQUENCE: 108

Asn Ser Asn Leu Lys Phe Leu Glu Val
1               5

<210> SEQ ID NO 109
<211> LENGTH: 9
<212> TYPE: PRT
<213> ORGANISM: Homo sapiens

<400> SEQUENCE: 109

Ile Ser Glu Asp Lys Ser Ile Ser Phe
1               5

<210> SEQ ID NO 110
<211> LENGTH: 9
<212> TYPE: PRT
<213> ORGANISM: Homo sapiens

<400> SEQUENCE: 110

Ile Gly Asp Lys Val Asp Ala Val Tyr
1               5

<210> SEQ ID NO 111
<211> LENGTH: 10
<212> TYPE: PRT
<213> ORGANISM: Homo sapiens

<400> SEQUENCE: 111

Thr Pro Ile Pro Phe Asp Lys Ile Leu Tyr
1               5                   10

<210> SEQ ID NO 112
<211> LENGTH: 11
<212> TYPE: PRT
<213> ORGANISM: Homo sapiens

<400> SEQUENCE: 112

Lys Ala Ser Ser Val Ser Ala Glu Asp Gly Tyr
1               5                   10

<210> SEQ ID NO 113
<211> LENGTH: 9
<212> TYPE: PRT
<213> ORGANISM: Homo sapiens

<400> SEQUENCE: 113

Ala Ser Cys Arg Ser Ser Ala Glu Tyr
1               5

<210> SEQ ID NO 114
<211> LENGTH: 11
<212> TYPE: PRT
<213> ORGANISM: Homo sapiens

<400> SEQUENCE: 114

Ala Val Ala Ala Ala Ala Gly Ala Ser Leu Tyr
1               5                   10

<210> SEQ ID NO 115
<211> LENGTH: 11
<212> TYPE: PRT
<213> ORGANISM: Homo sapiens

<400> SEQUENCE: 115
```

-continued

Asn Glu Ile Asp Ile His Ser Ile Tyr Phe Tyr
1               5                   10

<210> SEQ ID NO 116
<211> LENGTH: 9
<212> TYPE: PRT
<213> ORGANISM: Homo sapiens

<400> SEQUENCE: 116

Arg Ser Asp Ile Gly Glu Phe Glu Trp
1               5

<210> SEQ ID NO 117
<211> LENGTH: 9
<212> TYPE: PRT
<213> ORGANISM: Homo sapiens

<400> SEQUENCE: 117

Ser Pro Ala Lys Gln Phe Asn Ile Tyr
1               5

<210> SEQ ID NO 118
<211> LENGTH: 9
<212> TYPE: PRT
<213> ORGANISM: Homo sapiens

<400> SEQUENCE: 118

Leu Thr Trp Ala His Ser Ala Lys Tyr
1               5

<210> SEQ ID NO 119
<211> LENGTH: 10
<212> TYPE: PRT
<213> ORGANISM: Homo sapiens

<400> SEQUENCE: 119

Thr Val Phe Asp Glu Asn Leu Ser Arg Tyr
1               5                   10

<210> SEQ ID NO 120
<211> LENGTH: 9
<212> TYPE: PRT
<213> ORGANISM: Homo sapiens

<400> SEQUENCE: 120

Leu Val Asp Glu Asn Gln Ser Trp Tyr
1               5

<210> SEQ ID NO 121
<211> LENGTH: 9
<212> TYPE: PRT
<213> ORGANISM: Homo sapiens

<400> SEQUENCE: 121

Ser Ala Asp Glu Ala His Gly Leu Leu
1               5

<210> SEQ ID NO 122
<211> LENGTH: 9
<212> TYPE: PRT
<213> ORGANISM: Homo sapiens

<400> SEQUENCE: 122

Ile Ser Glu Ala Pro Leu Thr Glu Val
1               5

<210> SEQ ID NO 123
<211> LENGTH: 9
<212> TYPE: PRT
<213> ORGANISM: Homo sapiens

<400> SEQUENCE: 123

Leu Leu Lys Ala Lys Asp Ile Leu Tyr
1               5

<210> SEQ ID NO 124
<211> LENGTH: 12
<212> TYPE: PRT
<213> ORGANISM: Homo sapiens

<400> SEQUENCE: 124

Phe Leu Lys Val Thr Gly Tyr Asp Lys Asp Asp Tyr
1               5                   10

<210> SEQ ID NO 125
<211> LENGTH: 9
<212> TYPE: PRT
<213> ORGANISM: Homo sapiens

<400> SEQUENCE: 125

Phe Gln Tyr Glu Leu Arg Glu Leu Tyr
1               5

<210> SEQ ID NO 126
<211> LENGTH: 9
<212> TYPE: PRT
<213> ORGANISM: Homo sapiens

<400> SEQUENCE: 126

Thr Thr Asp Pro Lys Lys Phe Gln Tyr
1               5

<210> SEQ ID NO 127
<211> LENGTH: 9
<212> TYPE: PRT
<213> ORGANISM: Homo sapiens

<400> SEQUENCE: 127

Val Pro Phe Asn Leu Ile Thr Glu Tyr
1               5

<210> SEQ ID NO 128
<211> LENGTH: 11
<212> TYPE: PRT
<213> ORGANISM: Homo sapiens

<400> SEQUENCE: 128

Tyr Thr Glu Phe Val Asp Ala Thr Phe Thr Lys
1               5                   10

<210> SEQ ID NO 129
<211> LENGTH: 9
<212> TYPE: PRT
<213> ORGANISM: Homo sapiens

<400> SEQUENCE: 129

Ser Thr Ile Asp Phe Arg Ala Gly Phe
1               5

```
<210> SEQ ID NO 130
<211> LENGTH: 9
<212> TYPE: PRT
<213> ORGANISM: Homo sapiens

<400> SEQUENCE: 130

Tyr Ile Gly Leu Lys Gly Leu Tyr Phe
1               5

<210> SEQ ID NO 131
<211> LENGTH: 10
<212> TYPE: PRT
<213> ORGANISM: Homo sapiens

<400> SEQUENCE: 131

Leu Glu Asp Gly Ile Glu Gln Ser Ala Tyr
1               5                   10

<210> SEQ ID NO 132
<211> LENGTH: 9
<212> TYPE: PRT
<213> ORGANISM: Homo sapiens

<400> SEQUENCE: 132

Arg Thr His Ile Gly Tyr Lys Val Tyr
1               5

<210> SEQ ID NO 133
<211> LENGTH: 9
<212> TYPE: PRT
<213> ORGANISM: Homo sapiens

<400> SEQUENCE: 133

Ile Thr Asp Val Gly Pro Gly Asn Tyr
1               5

<210> SEQ ID NO 134
<211> LENGTH: 11
<212> TYPE: PRT
<213> ORGANISM: Homo sapiens

<400> SEQUENCE: 134

Ser Ala Pro Ser Ser Gly Ser Pro Leu Tyr
1               5                   10

<210> SEQ ID NO 135
<211> LENGTH: 9
<212> TYPE: PRT
<213> ORGANISM: Homo sapiens

<400> SEQUENCE: 135

Thr Phe Asp Lys Gln Ile Val Leu Leu
1               5

<210> SEQ ID NO 136
<211> LENGTH: 10
<212> TYPE: PRT
<213> ORGANISM: Homo sapiens

<400> SEQUENCE: 136

Arg Arg Leu Asn Phe Ser Gly Phe Gly Tyr
1               5                   10

<210> SEQ ID NO 137
<211> LENGTH: 9
```

-continued

<212> TYPE: PRT
<213> ORGANISM: Homo sapiens

<400> SEQUENCE: 137

Glu Ala Tyr Leu Glu Arg Ile Gly Tyr
1               5

<210> SEQ ID NO 138
<211> LENGTH: 11
<212> TYPE: PRT
<213> ORGANISM: Homo sapiens

<400> SEQUENCE: 138

Ile Pro Val His Asp Ser Val Gly Val Thr Tyr
1               5                   10

<210> SEQ ID NO 139
<211> LENGTH: 10
<212> TYPE: PRT
<213> ORGANISM: Homo sapiens

<400> SEQUENCE: 139

Pro Val His Asp Ser Val Gly Val Thr Tyr
1               5                   10

<210> SEQ ID NO 140
<211> LENGTH: 9
<212> TYPE: PRT
<213> ORGANISM: Homo sapiens

<400> SEQUENCE: 140

Ser Gln His Ile Phe Thr Val Ser Tyr
1               5

<210> SEQ ID NO 141
<211> LENGTH: 9
<212> TYPE: PRT
<213> ORGANISM: Homo sapiens

<400> SEQUENCE: 141

Asp Ala Val Ala Pro Gly Arg Glu Tyr
1               5

<210> SEQ ID NO 142
<211> LENGTH: 8
<212> TYPE: PRT
<213> ORGANISM: Homo sapiens

<400> SEQUENCE: 142

Ile Glu Lys Phe Ala Val Leu Tyr
1               5

<210> SEQ ID NO 143
<211> LENGTH: 9
<212> TYPE: PRT
<213> ORGANISM: Homo sapiens

<400> SEQUENCE: 143

His Val Ser Gly Gln Met Leu Tyr Phe
1               5

<210> SEQ ID NO 144
<211> LENGTH: 9
<212> TYPE: PRT
<213> ORGANISM: Homo sapiens

<400> SEQUENCE: 144

Arg Thr Ile Glu Gly Asp Phe Leu Trp
1               5

<210> SEQ ID NO 145
<211> LENGTH: 9
<212> TYPE: PRT
<213> ORGANISM: Homo sapiens

<400> SEQUENCE: 145

Leu Ser Asp Ala Val His Val Glu Phe
1               5

<210> SEQ ID NO 146
<211> LENGTH: 11
<212> TYPE: PRT
<213> ORGANISM: Homo sapiens

<400> SEQUENCE: 146

Leu Cys Ala Thr Val Cys Gly Thr Glu Gln Tyr
1               5                   10

<210> SEQ ID NO 147
<211> LENGTH: 9
<212> TYPE: PRT
<213> ORGANISM: Homo sapiens

<400> SEQUENCE: 147

Ala Gln Val Gln Asp Thr Gly Arg Tyr
1               5

<210> SEQ ID NO 148
<211> LENGTH: 10
<212> TYPE: PRT
<213> ORGANISM: Homo sapiens

<400> SEQUENCE: 148

Gly Thr Lys Gln Trp Val His Ala Arg Tyr
1               5                   10

<210> SEQ ID NO 149
<211> LENGTH: 10
<212> TYPE: PRT
<213> ORGANISM: Homo sapiens

<400> SEQUENCE: 149

Pro Ile Met Ser Ser Ser Gln Ala Leu Tyr
1               5                   10

<210> SEQ ID NO 150
<211> LENGTH: 12
<212> TYPE: PRT
<213> ORGANISM: Homo sapiens

<400> SEQUENCE: 150

Phe Thr Thr Leu Ser Asp Leu Gln Thr Asn Met Ala
1               5                   10

<210> SEQ ID NO 151
<211> LENGTH: 10
<212> TYPE: PRT
<213> ORGANISM: Homo sapiens

<400> SEQUENCE: 151

Tyr Glu Val Asp Thr Lys Leu Leu Ser Leu
1               5                   10

<210> SEQ ID NO 152
<211> LENGTH: 9
<212> TYPE: PRT
<213> ORGANISM: Homo sapiens

<400> SEQUENCE: 152

Tyr Leu Glu Asp Arg Pro Leu Ser Gln
1               5

<210> SEQ ID NO 153
<211> LENGTH: 9
<212> TYPE: PRT
<213> ORGANISM: Homo sapiens

<400> SEQUENCE: 153

His Ser Ile Glu Val Phe Thr His Tyr
1               5

<210> SEQ ID NO 154
<211> LENGTH: 8
<212> TYPE: PRT
<213> ORGANISM: Homo sapiens

<400> SEQUENCE: 154

Ser Ile Glu Val Phe Thr His Tyr
1               5

<210> SEQ ID NO 155
<211> LENGTH: 8
<212> TYPE: PRT
<213> ORGANISM: Homo sapiens

<400> SEQUENCE: 155

His Thr Met Glu Val Thr Val Tyr
1               5

<210> SEQ ID NO 156
<211> LENGTH: 9
<212> TYPE: PRT
<213> ORGANISM: Homo sapiens

<400> SEQUENCE: 156

Ser Thr Ala Leu Ser Ile Leu Leu Leu
1               5

<210> SEQ ID NO 157
<211> LENGTH: 9
<212> TYPE: PRT
<213> ORGANISM: Homo sapiens

<400> SEQUENCE: 157

Gly Leu Ile Glu Val Val Thr Gly Tyr
1               5

<210> SEQ ID NO 158
<211> LENGTH: 10
<212> TYPE: PRT
<213> ORGANISM: Homo sapiens

<400> SEQUENCE: 158

Glu Val Thr Asp Arg Asn Met Leu Ala Phe

```
<210> SEQ ID NO 159
<211> LENGTH: 10
<212> TYPE: PRT
<213> ORGANISM: Homo sapiens

<400> SEQUENCE: 159

Arg Gln Ala Pro Gly Pro Ala Arg Asp Tyr
1               5                   10

<210> SEQ ID NO 160
<211> LENGTH: 10
<212> TYPE: PRT
<213> ORGANISM: Homo sapiens

<400> SEQUENCE: 160

Glu Val Leu Gly Glu Glu Met Tyr Ala Tyr
1               5                   10

<210> SEQ ID NO 161
<211> LENGTH: 9
<212> TYPE: PRT
<213> ORGANISM: Homo sapiens

<400> SEQUENCE: 161

Glu Ala Ala Pro Asp Ile Met His Tyr
1               5

<210> SEQ ID NO 162
<211> LENGTH: 10
<212> TYPE: PRT
<213> ORGANISM: Homo sapiens

<400> SEQUENCE: 162

Ile Ala Asp Asn Pro Gln Leu Ser Phe Tyr
1               5                   10

<210> SEQ ID NO 163
<211> LENGTH: 10
<212> TYPE: PRT
<213> ORGANISM: Homo sapiens

<400> SEQUENCE: 163

Lys Ile Arg Ala Glu Val Leu Ser His Tyr
1               5                   10

<210> SEQ ID NO 164
<211> LENGTH: 9
<212> TYPE: PRT
<213> ORGANISM: Homo sapiens

<400> SEQUENCE: 164

Lys Leu Ala Gly Thr Val Phe Gln Tyr
1               5

<210> SEQ ID NO 165
<211> LENGTH: 9
<212> TYPE: PRT
<213> ORGANISM: Homo sapiens

<400> SEQUENCE: 165

Val Ser Val Tyr Asn Ser Tyr Pro Tyr
1               5
```

```
<210> SEQ ID NO 166
<211> LENGTH: 11
<212> TYPE: PRT
<213> ORGANISM: Homo sapiens

<400> SEQUENCE: 166

Tyr His Arg Ile Cys Glu Leu Leu Ser Asp Tyr
1               5                   10

<210> SEQ ID NO 167
<211> LENGTH: 9
<212> TYPE: PRT
<213> ORGANISM: Homo sapiens

<400> SEQUENCE: 167

Arg Ala Val Gln Pro Gly Glu Thr Tyr
1               5

<210> SEQ ID NO 168
<211> LENGTH: 9
<212> TYPE: PRT
<213> ORGANISM: Homo sapiens

<400> SEQUENCE: 168

Val Gln Pro Gly Glu Thr Tyr Thr Tyr
1               5

<210> SEQ ID NO 169
<211> LENGTH: 9
<212> TYPE: PRT
<213> ORGANISM: Homo sapiens

<400> SEQUENCE: 169

Thr Val Asp Asn Ala Asn Ile Leu Leu
1               5

<210> SEQ ID NO 170
<211> LENGTH: 9
<212> TYPE: PRT
<213> ORGANISM: Homo sapiens

<400> SEQUENCE: 170

Val Gln Ile Ala Lys Gly Met Asn Tyr
1               5

<210> SEQ ID NO 171
<211> LENGTH: 9
<212> TYPE: PRT
<213> ORGANISM: Homo sapiens

<400> SEQUENCE: 171

Ile Thr Asp Phe Gly Leu Ala Lys Leu
1               5

<210> SEQ ID NO 172
<211> LENGTH: 9
<212> TYPE: PRT
<213> ORGANISM: Homo sapiens

<400> SEQUENCE: 172

Phe Ser Glu Pro Phe His Leu Ile Val
1               5

<210> SEQ ID NO 173
```

-continued

```
<211> LENGTH: 9
<212> TYPE: PRT
<213> ORGANISM: Homo sapiens

<400> SEQUENCE: 173

Gln Ser Thr Thr Gly Val Ser His Tyr
1               5

<210> SEQ ID NO 174
<211> LENGTH: 12
<212> TYPE: PRT
<213> ORGANISM: Homo sapiens

<400> SEQUENCE: 174

Thr Ser Glu Val Glu Gly Leu Ala Phe Val Ser Tyr
1               5                   10

<210> SEQ ID NO 175
<211> LENGTH: 10
<212> TYPE: PRT
<213> ORGANISM: Homo sapiens

<400> SEQUENCE: 175

Gly Leu Glu Tyr Glu Ala Pro Lys Leu Tyr
1               5                   10

<210> SEQ ID NO 176
<211> LENGTH: 11
<212> TYPE: PRT
<213> ORGANISM: Homo sapiens

<400> SEQUENCE: 176

His Thr Asp Leu Glu Ser Pro Ser Ala Val Tyr
1               5                   10

<210> SEQ ID NO 177
<211> LENGTH: 9
<212> TYPE: PRT
<213> ORGANISM: Homo sapiens

<400> SEQUENCE: 177

Leu Val Asp Gly Lys Trp Gln Glu Phe
1               5

<210> SEQ ID NO 178
<211> LENGTH: 9
<212> TYPE: PRT
<213> ORGANISM: Homo sapiens

<400> SEQUENCE: 178

Thr Gln Arg Thr Ser Phe Gln Phe Tyr
1               5

<210> SEQ ID NO 179
<211> LENGTH: 10
<212> TYPE: PRT
<213> ORGANISM: Homo sapiens

<400> SEQUENCE: 179

Ser Ser Thr Asp Phe Thr Phe Ala Ser Trp
1               5                   10

<210> SEQ ID NO 180
<211> LENGTH: 9
<212> TYPE: PRT
```

<213> ORGANISM: Homo sapiens

<400> SEQUENCE: 180

Ala Gln Ile Ser Asp Thr Gly Arg Tyr
1               5

<210> SEQ ID NO 181
<211> LENGTH: 10
<212> TYPE: PRT
<213> ORGANISM: Homo sapiens

<400> SEQUENCE: 181

Ser Val Thr Asp Leu Ile Gly Gly Lys Trp
1               5                   10

<210> SEQ ID NO 182
<211> LENGTH: 9
<212> TYPE: PRT
<213> ORGANISM: Homo sapiens

<400> SEQUENCE: 182

Thr Gln Pro Glu Leu Ser Ser Arg Tyr
1               5

<210> SEQ ID NO 183
<211> LENGTH: 10
<212> TYPE: PRT
<213> ORGANISM: Homo sapiens

<400> SEQUENCE: 183

Leu Ala Asp Thr Asp Leu Gly Met Thr Phe
1               5                   10

<210> SEQ ID NO 184
<211> LENGTH: 9
<212> TYPE: PRT
<213> ORGANISM: Homo sapiens

<400> SEQUENCE: 184

Lys Thr Ile Gln Glu Val Ala Gly Tyr
1               5

<210> SEQ ID NO 185
<211> LENGTH: 13
<212> TYPE: PRT
<213> ORGANISM: Homo sapiens

<400> SEQUENCE: 185

Asn Ser Asp Glu Ser Ala Asp Ser Glu Pro His Lys Tyr
1               5                   10

<210> SEQ ID NO 186
<211> LENGTH: 9
<212> TYPE: PRT
<213> ORGANISM: Homo sapiens

<400> SEQUENCE: 186

Ala Val Ser Ser Gly Leu Phe Phe Tyr
1               5

<210> SEQ ID NO 187
<211> LENGTH: 10
<212> TYPE: PRT
<213> ORGANISM: Homo sapiens

```
<400> SEQUENCE: 187

Thr Gln Lys Ser Val Gln Val Leu Ala Tyr
1               5                   10

<210> SEQ ID NO 188
<211> LENGTH: 9
<212> TYPE: PRT
<213> ORGANISM: Homo sapiens

<400> SEQUENCE: 188

Asp Ile Pro Asp Tyr Leu Leu Gln Tyr
1               5

<210> SEQ ID NO 189
<211> LENGTH: 9
<212> TYPE: PRT
<213> ORGANISM: Homo sapiens

<400> SEQUENCE: 189

Phe Arg Gly Val Phe Val His Arg Tyr
1               5

<210> SEQ ID NO 190
<211> LENGTH: 9
<212> TYPE: PRT
<213> ORGANISM: Homo sapiens

<400> SEQUENCE: 190

Val Ser Ser Thr Val His Asn Leu Tyr
1               5

<210> SEQ ID NO 191
<211> LENGTH: 10
<212> TYPE: PRT
<213> ORGANISM: Homo sapiens

<400> SEQUENCE: 191

Phe Thr Arg Ala Phe Asp Gln Leu Arg Met
1               5                   10

<210> SEQ ID NO 192
<211> LENGTH: 8
<212> TYPE: PRT
<213> ORGANISM: Homo sapiens

<400> SEQUENCE: 192

Leu Ala Phe Tyr Tyr Gly Met Tyr
1               5

<210> SEQ ID NO 193
<211> LENGTH: 9
<212> TYPE: PRT
<213> ORGANISM: Homo sapiens

<400> SEQUENCE: 193

Ser Gln Asn Gly Gln Leu Ile His Tyr
1               5

<210> SEQ ID NO 194
<211> LENGTH: 10
<212> TYPE: PRT
<213> ORGANISM: Homo sapiens

<400> SEQUENCE: 194
```

```
Cys Tyr Thr Ala Asp Asn Glu Met Gly Tyr
1               5                   10

<210> SEQ ID NO 195
<211> LENGTH: 10
<212> TYPE: PRT
<213> ORGANISM: Homo sapiens

<400> SEQUENCE: 195

Tyr Thr Ala Asp Asn Glu Met Gly Tyr Tyr
1               5                   10

<210> SEQ ID NO 196
<211> LENGTH: 10
<212> TYPE: PRT
<213> ORGANISM: Homo sapiens

<400> SEQUENCE: 196

Arg Leu Ala Gln Tyr Thr Ile Glu Arg Tyr
1               5                   10

<210> SEQ ID NO 197
<211> LENGTH: 10
<212> TYPE: PRT
<213> ORGANISM: Homo sapiens

<400> SEQUENCE: 197

Asn Asp Glu Ile Asp Lys Leu Thr Gly Tyr
1               5                   10

<210> SEQ ID NO 198
<211> LENGTH: 10
<212> TYPE: PRT
<213> ORGANISM: Homo sapiens

<400> SEQUENCE: 198

Lys Leu Thr Asp Tyr Ile Asn Ala Asn Tyr
1               5                   10

<210> SEQ ID NO 199
<211> LENGTH: 9
<212> TYPE: PRT
<213> ORGANISM: Homo sapiens

<400> SEQUENCE: 199

Leu Cys Ala Ala Val Leu Ala Lys Tyr
1               5

<210> SEQ ID NO 200
<211> LENGTH: 9
<212> TYPE: PRT
<213> ORGANISM: Homo sapiens

<400> SEQUENCE: 200

Ser Leu Pro Glu Phe Gly Leu Thr Tyr
1               5

<210> SEQ ID NO 201
<211> LENGTH: 10
<212> TYPE: PRT
<213> ORGANISM: Homo sapiens

<400> SEQUENCE: 201

Ser Leu Pro Glu Phe Gly Leu Thr Tyr Tyr
1               5                   10
```

```
<210> SEQ ID NO 202
<211> LENGTH: 10
<212> TYPE: PRT
<213> ORGANISM: Homo sapiens

<400> SEQUENCE: 202

Gln Thr Asp Ile Asn Gly Gly Ser Leu Lys
1               5                   10

<210> SEQ ID NO 203
<211> LENGTH: 9
<212> TYPE: PRT
<213> ORGANISM: Homo sapiens

<400> SEQUENCE: 203

Leu Ser Gln Asp Glu Leu Ser Lys Phe
1               5

<210> SEQ ID NO 204
<211> LENGTH: 9
<212> TYPE: PRT
<213> ORGANISM: Homo sapiens

<400> SEQUENCE: 204

Asn Val Lys Glu Ala Pro Thr Glu Tyr
1               5

<210> SEQ ID NO 205
<211> LENGTH: 9
<212> TYPE: PRT
<213> ORGANISM: Homo sapiens

<400> SEQUENCE: 205

Arg Met Gln Glu Gly Ser Glu Val Tyr
1               5

<210> SEQ ID NO 206
<211> LENGTH: 9
<212> TYPE: PRT
<213> ORGANISM: Homo sapiens

<400> SEQUENCE: 206

Arg Val Phe Val Ala Val Thr Leu Tyr
1               5

<210> SEQ ID NO 207
<211> LENGTH: 12
<212> TYPE: PRT
<213> ORGANISM: Homo sapiens

<400> SEQUENCE: 207

Leu Leu Glu Gly Glu Asp Ala His Leu Thr Gln Tyr
1               5                   10

<210> SEQ ID NO 208
<211> LENGTH: 9
<212> TYPE: PRT
<213> ORGANISM: Homo sapiens

<400> SEQUENCE: 208

Leu Leu Ile Ser Lys Ala Glu Asp Tyr
1               5
```

-continued

```
<210> SEQ ID NO 209
<211> LENGTH: 9
<212> TYPE: PRT
<213> ORGANISM: Homo sapiens

<400> SEQUENCE: 209

Glu Ala Asp Pro Phe Leu Lys Tyr Leu
1               5

<210> SEQ ID NO 210
<211> LENGTH: 10
<212> TYPE: PRT
<213> ORGANISM: Homo sapiens

<400> SEQUENCE: 210

Leu Leu Glu Ala Asp Pro Phe Leu Lys Tyr
1               5                   10

<210> SEQ ID NO 211
<211> LENGTH: 9
<212> TYPE: PRT
<213> ORGANISM: Homo sapiens

<400> SEQUENCE: 211

Tyr Leu Asn Glu Trp Gly Ser Arg Phe
1               5

<210> SEQ ID NO 212
<211> LENGTH: 9
<212> TYPE: PRT
<213> ORGANISM: Homo sapiens

<400> SEQUENCE: 212

Met Met Thr Asp Leu Thr Ser Val Tyr
1               5

<210> SEQ ID NO 213
<211> LENGTH: 10
<212> TYPE: PRT
<213> ORGANISM: Homo sapiens

<400> SEQUENCE: 213

Val Ser Asp Ser Thr Thr Glu Ile Thr Tyr
1               5                   10

<210> SEQ ID NO 214
<211> LENGTH: 9
<212> TYPE: PRT
<213> ORGANISM: Homo sapiens

<400> SEQUENCE: 214

Val Gln Asp Pro Ser Leu Pro Val Tyr
1               5

<210> SEQ ID NO 215
<211> LENGTH: 10
<212> TYPE: PRT
<213> ORGANISM: Homo sapiens

<400> SEQUENCE: 215

Asp Thr Leu Glu Ala Ala Thr Ser Leu Tyr
1               5                   10

<210> SEQ ID NO 216
<211> LENGTH: 9
```

```
<212> TYPE: PRT
<213> ORGANISM: Homo sapiens

<400> SEQUENCE: 216

Asn Ser Met Leu Asp Pro Leu Val Tyr
1               5

<210> SEQ ID NO 217
<211> LENGTH: 10
<212> TYPE: PRT
<213> ORGANISM: Homo sapiens

<400> SEQUENCE: 217

Leu Met Asp Glu Gly Ala Val Leu Thr Leu
1               5                   10

<210> SEQ ID NO 218
<211> LENGTH: 8
<212> TYPE: PRT
<213> ORGANISM: Homo sapiens

<400> SEQUENCE: 218

Phe Thr Ala Gln Leu Gln Leu Tyr
1               5

<210> SEQ ID NO 219
<211> LENGTH: 10
<212> TYPE: PRT
<213> ORGANISM: Homo sapiens

<400> SEQUENCE: 219

Lys Thr Glu Leu Glu Thr Ala Leu Tyr Tyr
1               5                   10

<210> SEQ ID NO 220
<211> LENGTH: 9
<212> TYPE: PRT
<213> ORGANISM: Homo sapiens

<400> SEQUENCE: 220

Asp Val Glu Arg Ile Lys Asp Thr Tyr
1               5

<210> SEQ ID NO 221
<211> LENGTH: 10
<212> TYPE: PRT
<213> ORGANISM: Homo sapiens

<400> SEQUENCE: 221

Thr Asp Val Glu Arg Ile Lys Asp Thr Tyr
1               5                   10

<210> SEQ ID NO 222
<211> LENGTH: 9
<212> TYPE: PRT
<213> ORGANISM: Homo sapiens

<400> SEQUENCE: 222

Gly Ser Pro Asp Ala Val Val Ser Tyr
1               5

<210> SEQ ID NO 223
<211> LENGTH: 10
<212> TYPE: PRT
<213> ORGANISM: Homo sapiens
```

<400> SEQUENCE: 223

Asn Ala Val Asp Val Val Pro Ser Ser Phe
1               5                   10

<210> SEQ ID NO 224
<211> LENGTH: 10
<212> TYPE: PRT
<213> ORGANISM: Homo sapiens

<400> SEQUENCE: 224

Arg Thr Asp Glu Gly Asp Asn Arg Val Trp
1               5                   10

<210> SEQ ID NO 225
<211> LENGTH: 9
<212> TYPE: PRT
<213> ORGANISM: Homo sapiens

<400> SEQUENCE: 225

Ser Thr Asp Pro Asn Ile Val Arg Lys
1               5

<210> SEQ ID NO 226
<211> LENGTH: 10
<212> TYPE: PRT
<213> ORGANISM: Homo sapiens

<400> SEQUENCE: 226

Gln Ile Thr Pro Lys His Asn Gly Leu Tyr
1               5                   10

<210> SEQ ID NO 227
<211> LENGTH: 10
<212> TYPE: PRT
<213> ORGANISM: Homo sapiens

<400> SEQUENCE: 227

Glu Ser Ala Pro Lys Glu Val Ser Arg Tyr
1               5                   10

<210> SEQ ID NO 228
<211> LENGTH: 9
<212> TYPE: PRT
<213> ORGANISM: Homo sapiens

<400> SEQUENCE: 228

Lys Ser Phe Asp Asp Ile Ala Lys Tyr
1               5

<210> SEQ ID NO 229
<211> LENGTH: 8
<212> TYPE: PRT
<213> ORGANISM: Homo sapiens

<400> SEQUENCE: 229

Met Thr Asp Val Phe Ile Asp Tyr
1               5

<210> SEQ ID NO 230
<211> LENGTH: 9
<212> TYPE: PRT
<213> ORGANISM: Homo sapiens

<400> SEQUENCE: 230

Cys Val Ile Glu Thr Phe His Lys Tyr
1               5

<210> SEQ ID NO 231
<211> LENGTH: 9
<212> TYPE: PRT
<213> ORGANISM: Homo sapiens

<400> SEQUENCE: 231

Leu Leu Pro Leu Leu Val Met Ala Tyr
1               5

<210> SEQ ID NO 232
<211> LENGTH: 12
<212> TYPE: PRT
<213> ORGANISM: Homo sapiens

<400> SEQUENCE: 232

Arg Tyr Leu Asn Ile Val His Ala Thr Gln Leu Tyr
1               5                   10

<210> SEQ ID NO 233
<211> LENGTH: 9
<212> TYPE: PRT
<213> ORGANISM: Homo sapiens

<400> SEQUENCE: 233

Arg Ile Asn Ser Ala Thr Gly Gln Tyr
1               5

<210> SEQ ID NO 234
<211> LENGTH: 9
<212> TYPE: PRT
<213> ORGANISM: Homo sapiens

<400> SEQUENCE: 234

Tyr Thr Asp Leu Thr Thr Ile Gln Val
1               5

<210> SEQ ID NO 235
<211> LENGTH: 9
<212> TYPE: PRT
<213> ORGANISM: Homo sapiens

<400> SEQUENCE: 235

Ser Ile Glu Ile Asp His Thr Gln Tyr
1               5

<210> SEQ ID NO 236
<211> LENGTH: 9
<212> TYPE: PRT
<213> ORGANISM: Homo sapiens

<400> SEQUENCE: 236

Val Leu Asp Ser Leu Leu Ala Gln Tyr
1               5

<210> SEQ ID NO 237
<211> LENGTH: 11
<212> TYPE: PRT
<213> ORGANISM: Homo sapiens

<400> SEQUENCE: 237

Ala Gln Glu Ala Ala Val Phe Leu Thr Leu Tyr

<210> SEQ ID NO 238
<211> LENGTH: 12
<212> TYPE: PRT
<213> ORGANISM: Homo sapiens

<400> SEQUENCE: 238

Glu Thr Asp Trp Gly Leu Leu Lys Gly His Thr Tyr
1               5                   10

<210> SEQ ID NO 239
<211> LENGTH: 11
<212> TYPE: PRT
<213> ORGANISM: Homo sapiens

<400> SEQUENCE: 239

Ser Ser Glu Arg Gly Ser Pro Ile Glu Lys Tyr
1               5                   10

<210> SEQ ID NO 240
<211> LENGTH: 10
<212> TYPE: PRT
<213> ORGANISM: Homo sapiens

<400> SEQUENCE: 240

Glu Val Leu Asp Ser Leu Leu Ala Gln Tyr
1               5                   10

<210> SEQ ID NO 241
<211> LENGTH: 9
<212> TYPE: PRT
<213> ORGANISM: Homo sapiens

<400> SEQUENCE: 241

Ser Leu Met Val Ala Ser Leu Thr Tyr
1               5

<210> SEQ ID NO 242
<211> LENGTH: 9
<212> TYPE: PRT
<213> ORGANISM: Homo sapiens

<400> SEQUENCE: 242

Gly Thr Asn Leu Pro Thr Leu Leu Trp
1               5

<210> SEQ ID NO 243
<211> LENGTH: 9
<212> TYPE: PRT
<213> ORGANISM: Homo sapiens

<400> SEQUENCE: 243

Leu Thr Ser Glu Asp Thr Gly Ala Tyr
1               5

<210> SEQ ID NO 244
<211> LENGTH: 9
<212> TYPE: PRT
<213> ORGANISM: Homo sapiens

<400> SEQUENCE: 244

Val Thr Lys Tyr Ile Ala Gly Pro Tyr
1               5

<210> SEQ ID NO 245
<211> LENGTH: 9
<212> TYPE: PRT
<213> ORGANISM: Homo sapiens

<400> SEQUENCE: 245

Leu Ser Asp Asn Ala Ala Asn Arg Tyr
1               5

<210> SEQ ID NO 246
<211> LENGTH: 10
<212> TYPE: PRT
<213> ORGANISM: Homo sapiens

<400> SEQUENCE: 246

Ala Arg Leu Glu Gly Glu Ile Ala Thr Tyr
1               5                   10

<210> SEQ ID NO 247
<211> LENGTH: 9
<212> TYPE: PRT
<213> ORGANISM: Homo sapiens

<400> SEQUENCE: 247

Ser Met Ile Arg Val Gly Thr Asn Tyr
1               5

<210> SEQ ID NO 248
<211> LENGTH: 9
<212> TYPE: PRT
<213> ORGANISM: Homo sapiens

<400> SEQUENCE: 248

Val Thr Asp Ile Asp Glu Leu Gly Lys
1               5

<210> SEQ ID NO 249
<211> LENGTH: 9
<212> TYPE: PRT
<213> ORGANISM: Homo sapiens

<400> SEQUENCE: 249

Gly Val Gly Phe Thr Glu Leu Glu Tyr
1               5

<210> SEQ ID NO 250
<211> LENGTH: 10
<212> TYPE: PRT
<213> ORGANISM: Homo sapiens

<400> SEQUENCE: 250

Gly Tyr Val Cys Asn Ala Cys Gly Leu Tyr
1               5                   10

<210> SEQ ID NO 251
<211> LENGTH: 9
<212> TYPE: PRT
<213> ORGANISM: Homo sapiens

<400> SEQUENCE: 251

Gly Ile Glu Met Thr Tyr Glu Thr Tyr
1               5

<210> SEQ ID NO 252

```
<211> LENGTH: 10
<212> TYPE: PRT
<213> ORGANISM: Homo sapiens

<400> SEQUENCE: 252

Asp Thr Thr Ser His Thr Tyr Leu Gln Tyr
1               5                   10

<210> SEQ ID NO 253
<211> LENGTH: 9
<212> TYPE: PRT
<213> ORGANISM: Homo sapiens

<400> SEQUENCE: 253

Tyr Leu Glu Ser His Gly Leu Ala Tyr
1               5

<210> SEQ ID NO 254
<211> LENGTH: 9
<212> TYPE: PRT
<213> ORGANISM: Homo sapiens

<400> SEQUENCE: 254

Phe Leu Phe Asn Asp Ala Leu Leu Tyr
1               5

<210> SEQ ID NO 255
<211> LENGTH: 8
<212> TYPE: PRT
<213> ORGANISM: Homo sapiens

<400> SEQUENCE: 255

Trp Glu Leu Asp Ser Leu Glu Tyr
1               5

<210> SEQ ID NO 256
<211> LENGTH: 10
<212> TYPE: PRT
<213> ORGANISM: Homo sapiens

<400> SEQUENCE: 256

His Ala Phe Glu Ser Asn Asn Phe Ile Tyr
1               5                   10

<210> SEQ ID NO 257
<211> LENGTH: 10
<212> TYPE: PRT
<213> ORGANISM: Homo sapiens

<400> SEQUENCE: 257

Lys Ser Glu Met Asn Val Asn Met Lys Tyr
1               5                   10

<210> SEQ ID NO 258
<211> LENGTH: 9
<212> TYPE: PRT
<213> ORGANISM: Homo sapiens

<400> SEQUENCE: 258

Arg Pro Ser Ser Val Leu Thr Ile Tyr
1               5

<210> SEQ ID NO 259
<211> LENGTH: 9
<212> TYPE: PRT
```

```
<213> ORGANISM: Homo sapiens

<400> SEQUENCE: 259

Ala Pro Asp Glu Val Val Ala Leu Leu
1               5

<210> SEQ ID NO 260
<211> LENGTH: 10
<212> TYPE: PRT
<213> ORGANISM: Homo sapiens

<400> SEQUENCE: 260

Lys Pro Thr Glu Asp Ser Ala Asn Val Tyr
1               5                   10

<210> SEQ ID NO 261
<211> LENGTH: 11
<212> TYPE: PRT
<213> ORGANISM: Homo sapiens

<400> SEQUENCE: 261

Met Thr Glu Gly Ser Thr Val Asn Thr Glu Tyr
1               5                   10

<210> SEQ ID NO 262
<211> LENGTH: 10
<212> TYPE: PRT
<213> ORGANISM: Homo sapiens

<400> SEQUENCE: 262

Asn Val Lys His Phe Leu Asn Asp Leu Tyr
1               5                   10

<210> SEQ ID NO 263
<211> LENGTH: 10
<212> TYPE: PRT
<213> ORGANISM: Homo sapiens

<400> SEQUENCE: 263

Asp Cys Met Asp Thr Glu Gly Ser Tyr Met
1               5                   10

<210> SEQ ID NO 264
<211> LENGTH: 9
<212> TYPE: PRT
<213> ORGANISM: Homo sapiens

<400> SEQUENCE: 264

Tyr Arg Asp Pro Val Phe Val Ser Leu
1               5

<210> SEQ ID NO 265
<211> LENGTH: 9
<212> TYPE: PRT
<213> ORGANISM: Homo sapiens

<400> SEQUENCE: 265

Leu Ser Asp Ile Asp Ser Arg Tyr Ile
1               5

<210> SEQ ID NO 266
<211> LENGTH: 9
<212> TYPE: PRT
<213> ORGANISM: Homo sapiens
```

<400> SEQUENCE: 266

Leu Thr Asp Ser Phe Leu Leu Arg Phe
1               5

<210> SEQ ID NO 267
<211> LENGTH: 8
<212> TYPE: PRT
<213> ORGANISM: Homo sapiens

<400> SEQUENCE: 267

Ile Val Ala Asp Asp Thr Val Tyr
1               5

<210> SEQ ID NO 268
<211> LENGTH: 9
<212> TYPE: PRT
<213> ORGANISM: Homo sapiens

<400> SEQUENCE: 268

Ala Ile Leu His His Leu Tyr Phe Tyr
1               5

<210> SEQ ID NO 269
<211> LENGTH: 11
<212> TYPE: PRT
<213> ORGANISM: Homo sapiens

<400> SEQUENCE: 269

Leu Pro Ser Pro Ala Ala Thr Ile Trp Asp Tyr
1               5                   10

<210> SEQ ID NO 270
<211> LENGTH: 10
<212> TYPE: PRT
<213> ORGANISM: Homo sapiens

<400> SEQUENCE: 270

Asp Leu Lys Ile Asp Leu Ala Ala Gln Tyr
1               5                   10

<210> SEQ ID NO 271
<211> LENGTH: 10
<212> TYPE: PRT
<213> ORGANISM: Homo sapiens

<400> SEQUENCE: 271

Val Ala Glu Pro Pro Val Val Cys Ser Tyr
1               5                   10

<210> SEQ ID NO 272
<211> LENGTH: 9
<212> TYPE: PRT
<213> ORGANISM: Homo sapiens

<400> SEQUENCE: 272

Ile Pro Gln Asp Glu Cys Leu Arg Tyr
1               5

<210> SEQ ID NO 273
<211> LENGTH: 10
<212> TYPE: PRT
<213> ORGANISM: Homo sapiens

<400> SEQUENCE: 273

Cys Gly Pro Asn Glu Ile Asn His Phe Tyr
1               5                   10

<210> SEQ ID NO 274
<211> LENGTH: 9
<212> TYPE: PRT
<213> ORGANISM: Homo sapiens

<400> SEQUENCE: 274

Tyr Ala Asp Ile His Gly Asp Leu Leu
1               5

<210> SEQ ID NO 275
<211> LENGTH: 11
<212> TYPE: PRT
<213> ORGANISM: Homo sapiens

<400> SEQUENCE: 275

Glu Ser Asp Glu Met Glu Asn Leu Leu Thr Tyr
1               5                   10

<210> SEQ ID NO 276
<211> LENGTH: 11
<212> TYPE: PRT
<213> ORGANISM: Homo sapiens

<400> SEQUENCE: 276

Gln Ile Thr Ser Phe Ala Ser Gly Thr Ser Tyr
1               5                   10

<210> SEQ ID NO 277
<211> LENGTH: 9
<212> TYPE: PRT
<213> ORGANISM: Homo sapiens

<400> SEQUENCE: 277

Leu Pro Ala Pro Gly Phe Leu Phe Tyr
1               5

<210> SEQ ID NO 278
<211> LENGTH: 9
<212> TYPE: PRT
<213> ORGANISM: Homo sapiens

<400> SEQUENCE: 278

Ala Ala Thr Val Lys Ser Asp Ile Tyr
1               5

<210> SEQ ID NO 279
<211> LENGTH: 8
<212> TYPE: PRT
<213> ORGANISM: Homo sapiens

<400> SEQUENCE: 279

Leu Met Thr Val Leu Leu Lys Tyr
1               5

<210> SEQ ID NO 280
<211> LENGTH: 12
<212> TYPE: PRT
<213> ORGANISM: Homo sapiens

<400> SEQUENCE: 280

Thr Thr Glu Met Val Ser Asn Glu Ser Val Asp Tyr
1               5                   10

<210> SEQ ID NO 281
<211> LENGTH: 9
<212> TYPE: PRT
<213> ORGANISM: Homo sapiens

<400> SEQUENCE: 281

Tyr Pro Asp Leu Ser Glu Leu Leu Met
1               5

<210> SEQ ID NO 282
<211> LENGTH: 11
<212> TYPE: PRT
<213> ORGANISM: Homo sapiens

<400> SEQUENCE: 282

Gln Ala Met Pro Ser Trp Pro Thr Ala Ala Tyr
1               5                   10

<210> SEQ ID NO 283
<211> LENGTH: 9
<212> TYPE: PRT
<213> ORGANISM: Homo sapiens

<400> SEQUENCE: 283

Glu Thr Ile Leu Val Ser Ser Ser Tyr
1               5

<210> SEQ ID NO 284
<211> LENGTH: 9
<212> TYPE: PRT
<213> ORGANISM: Homo sapiens

<400> SEQUENCE: 284

Thr Cys Ser His Thr Phe Val Tyr Tyr
1               5

<210> SEQ ID NO 285
<211> LENGTH: 12
<212> TYPE: PRT
<213> ORGANISM: Homo sapiens

<400> SEQUENCE: 285

Val Leu Pro His His Ser Glu Gly Ala Cys Val Tyr
1               5                   10

<210> SEQ ID NO 286
<211> LENGTH: 10
<212> TYPE: PRT
<213> ORGANISM: Homo sapiens

<400> SEQUENCE: 286

Ala Thr Asp Met Glu Gly Asn Leu Asn Tyr
1               5                   10

<210> SEQ ID NO 287
<211> LENGTH: 9
<212> TYPE: PRT
<213> ORGANISM: Homo sapiens

<400> SEQUENCE: 287

Glu Asn Ser Ile Glu Asp Leu Gln Tyr
1               5

<210> SEQ ID NO 288
<211> LENGTH: 8
<212> TYPE: PRT
<213> ORGANISM: Homo sapiens

<400> SEQUENCE: 288

Thr Glu Glu Lys Phe Val Ser Tyr
1               5

<210> SEQ ID NO 289
<211> LENGTH: 9
<212> TYPE: PRT
<213> ORGANISM: Homo sapiens

<400> SEQUENCE: 289

Tyr Thr Ser His Glu Asp Ile Gly Tyr
1               5

<210> SEQ ID NO 290
<211> LENGTH: 12
<212> TYPE: PRT
<213> ORGANISM: Homo sapiens

<400> SEQUENCE: 290

Gly Gln Phe Thr Gly Thr Ala Gly Ala Cys Arg Tyr
1               5                   10

<210> SEQ ID NO 291
<211> LENGTH: 10
<212> TYPE: PRT
<213> ORGANISM: Homo sapiens

<400> SEQUENCE: 291

Thr Ser Asp Val Thr Gly Ser Leu Thr Tyr
1               5                   10

<210> SEQ ID NO 292
<211> LENGTH: 12
<212> TYPE: PRT
<213> ORGANISM: Homo sapiens

<400> SEQUENCE: 292

Val Leu Asp Phe Ala Pro Pro Gly Ala Ser Ala Tyr
1               5                   10

<210> SEQ ID NO 293
<211> LENGTH: 9
<212> TYPE: PRT
<213> ORGANISM: Homo sapiens

<400> SEQUENCE: 293

Ile Ile Ser Val Leu Ile Ala Ile Tyr
1               5

<210> SEQ ID NO 294
<211> LENGTH: 8
<212> TYPE: PRT
<213> ORGANISM: Homo sapiens

<400> SEQUENCE: 294

Met Met Glu Met Glu Gly Met Tyr
1               5

<210> SEQ ID NO 295
<211> LENGTH: 11

<212> TYPE: PRT
<213> ORGANISM: Homo sapiens

<400> SEQUENCE: 295

Gly Gln Arg Leu Asp Glu Ala Met Ile Ser Tyr
1               5                   10

<210> SEQ ID NO 296
<211> LENGTH: 8
<212> TYPE: PRT
<213> ORGANISM: Homo sapiens

<400> SEQUENCE: 296

His Met Leu Ala Ala Met Ala Tyr
1               5

<210> SEQ ID NO 297
<211> LENGTH: 9
<212> TYPE: PRT
<213> ORGANISM: Homo sapiens

<400> SEQUENCE: 297

Arg Leu Asp Glu Ala Met Ile Ser Tyr
1               5

<210> SEQ ID NO 298
<211> LENGTH: 9
<212> TYPE: PRT
<213> ORGANISM: Homo sapiens

<400> SEQUENCE: 298

Lys Phe Asp Val Ile Asn His Tyr Phe
1               5

<210> SEQ ID NO 299
<211> LENGTH: 9
<212> TYPE: PRT
<213> ORGANISM: Homo sapiens

<400> SEQUENCE: 299

Glu Val Asp Ser Val Ala Leu Ser Leu
1               5

<210> SEQ ID NO 300
<211> LENGTH: 11
<212> TYPE: PRT
<213> ORGANISM: Homo sapiens

<400> SEQUENCE: 300

Val Ser Ile Asn Pro Asn Ser Gly Asp Ile Tyr
1               5                   10

<210> SEQ ID NO 301
<211> LENGTH: 9
<212> TYPE: PRT
<213> ORGANISM: Homo sapiens

<400> SEQUENCE: 301

Glu Ser Gln Thr Cys Ala Ser Asp Tyr
1               5

<210> SEQ ID NO 302
<211> LENGTH: 11
<212> TYPE: PRT
<213> ORGANISM: Homo sapiens

<400> SEQUENCE: 302

Phe Tyr Leu Ser Thr Pro Glu Asn Tyr His Tyr
1               5                   10

<210> SEQ ID NO 303
<211> LENGTH: 12
<212> TYPE: PRT
<213> ORGANISM: Homo sapiens

<400> SEQUENCE: 303

Gly Phe Gly Gly Leu Ser Ser Gln Gly Val Tyr Tyr
1               5                   10

<210> SEQ ID NO 304
<211> LENGTH: 10
<212> TYPE: PRT
<213> ORGANISM: Homo sapiens

<400> SEQUENCE: 304

Phe Ser Glu Asn Leu Ile Tyr Thr Tyr Ile
1               5                   10

<210> SEQ ID NO 305
<211> LENGTH: 9
<212> TYPE: PRT
<213> ORGANISM: Homo sapiens

<400> SEQUENCE: 305

Tyr Ala Asp Leu Leu Ile Tyr Thr Tyr
1               5

<210> SEQ ID NO 306
<211> LENGTH: 9
<212> TYPE: PRT
<213> ORGANISM: Homo sapiens

<400> SEQUENCE: 306

Lys Ser Phe Glu Thr Thr Val Arg Tyr
1               5

<210> SEQ ID NO 307
<211> LENGTH: 9
<212> TYPE: PRT
<213> ORGANISM: Homo sapiens

<400> SEQUENCE: 307

Asp Thr Asp Asp Arg Glu Leu Arg Tyr
1               5

<210> SEQ ID NO 308
<211> LENGTH: 9
<212> TYPE: PRT
<213> ORGANISM: Homo sapiens

<400> SEQUENCE: 308

Glu Leu Ala Ala Gly Gln Val Val Tyr
1               5

<210> SEQ ID NO 309
<211> LENGTH: 9
<212> TYPE: PRT
<213> ORGANISM: Homo sapiens

<400> SEQUENCE: 309

Glu Val Asp Arg Asn Leu Ile Gln Tyr
1               5

<210> SEQ ID NO 310
<211> LENGTH: 10
<212> TYPE: PRT
<213> ORGANISM: Homo sapiens

<400> SEQUENCE: 310

Lys Ala Phe Gln Glu Leu Gly Val Arg Tyr
1               5                   10

<210> SEQ ID NO 311
<211> LENGTH: 11
<212> TYPE: PRT
<213> ORGANISM: Homo sapiens

<400> SEQUENCE: 311

Thr Val Thr Asp Gly Thr His Thr Asp Phe Tyr
1               5                   10

<210> SEQ ID NO 312
<211> LENGTH: 9
<212> TYPE: PRT
<213> ORGANISM: Homo sapiens

<400> SEQUENCE: 312

Val Thr Asp Gly Ile Asn Pro Leu Ile
1               5

<210> SEQ ID NO 313
<211> LENGTH: 10
<212> TYPE: PRT
<213> ORGANISM: Homo sapiens

<400> SEQUENCE: 313

Val Thr Asp Gly Thr His Thr Asp Phe Tyr
1               5                   10

<210> SEQ ID NO 314
<211> LENGTH: 12
<212> TYPE: PRT
<213> ORGANISM: Homo sapiens

<400> SEQUENCE: 314

Pro Pro Glu Ala Asn Ser Leu Gln Gly Ala Leu Tyr
1               5                   10

<210> SEQ ID NO 315
<211> LENGTH: 9
<212> TYPE: PRT
<213> ORGANISM: Homo sapiens

<400> SEQUENCE: 315

Val Leu Lys Ile Glu Leu Glu Thr Tyr
1               5

<210> SEQ ID NO 316
<211> LENGTH: 10
<212> TYPE: PRT
<213> ORGANISM: Homo sapiens

<400> SEQUENCE: 316

Tyr Thr Cys Glu Glu Cys Gly Gln Ala Phe

```
1               5                   10

<210> SEQ ID NO 317
<211> LENGTH: 10
<212> TYPE: PRT
<213> ORGANISM: Homo sapiens

<400> SEQUENCE: 317

Glu Asp Leu Leu Glu Val Leu Asp Met Tyr
1               5                   10

<210> SEQ ID NO 318
<211> LENGTH: 9
<212> TYPE: PRT
<213> ORGANISM: Homo sapiens

<400> SEQUENCE: 318

Tyr Met Thr Ser Met Ala Leu Asn Tyr
1               5

<210> SEQ ID NO 319
<211> LENGTH: 9
<212> TYPE: PRT
<213> ORGANISM: Homo sapiens

<400> SEQUENCE: 319

Phe Thr Asp Pro His Ile Ile Thr Phe
1               5

<210> SEQ ID NO 320
<211> LENGTH: 11
<212> TYPE: PRT
<213> ORGANISM: Homo sapiens

<400> SEQUENCE: 320

Gln Ala Leu Gln Asp Lys Leu Gln Thr Phe Tyr
1               5                   10

<210> SEQ ID NO 321
<211> LENGTH: 12
<212> TYPE: PRT
<213> ORGANISM: Homo sapiens

<400> SEQUENCE: 321

Asp Gly Ile Ala Asp Ala Ser Asn Leu Ser Tyr Tyr
1               5                   10

<210> SEQ ID NO 322
<211> LENGTH: 10
<212> TYPE: PRT
<213> ORGANISM: Homo sapiens

<400> SEQUENCE: 322

Phe Ser Glu Leu Asn Pro Leu Ala Leu Tyr
1               5                   10

<210> SEQ ID NO 323
<211> LENGTH: 11
<212> TYPE: PRT
<213> ORGANISM: Homo sapiens

<400> SEQUENCE: 323

Lys Thr Leu Gln Lys Pro Val Leu Pro Leu Tyr
1               5                   10
```

```
<210> SEQ ID NO 324
<211> LENGTH: 9
<212> TYPE: PRT
<213> ORGANISM: Homo sapiens

<400> SEQUENCE: 324

Arg Thr Gly Ile Phe Pro Tyr Arg Phe
1               5

<210> SEQ ID NO 325
<211> LENGTH: 9
<212> TYPE: PRT
<213> ORGANISM: Homo sapiens

<400> SEQUENCE: 325

Leu Gln Lys Pro Val Leu Pro Leu Tyr
1               5

<210> SEQ ID NO 326
<211> LENGTH: 9
<212> TYPE: PRT
<213> ORGANISM: Homo sapiens

<400> SEQUENCE: 326

Ser Thr Ser Arg Leu Thr Leu Phe Ser
1               5

<210> SEQ ID NO 327
<211> LENGTH: 10
<212> TYPE: PRT
<213> ORGANISM: Homo sapiens

<400> SEQUENCE: 327

Ile Met Leu Ser Val Asp Gln His Leu Tyr
1               5                   10

<210> SEQ ID NO 328
<211> LENGTH: 10
<212> TYPE: PRT
<213> ORGANISM: Homo sapiens

<400> SEQUENCE: 328

Leu Leu Asp Glu Asp Asn Asn Ile Lys Leu
1               5                   10

<210> SEQ ID NO 329
<211> LENGTH: 12
<212> TYPE: PRT
<213> ORGANISM: Homo sapiens

<400> SEQUENCE: 329

Asn Thr Asp Ser Met Thr Leu Asn Asn Thr Ala Tyr
1               5                   10

<210> SEQ ID NO 330
<211> LENGTH: 11
<212> TYPE: PRT
<213> ORGANISM: Homo sapiens

<400> SEQUENCE: 330

Glu Gly Glu Leu Ser Glu Gly Glu His Trp Tyr
1               5                   10

<210> SEQ ID NO 331
```

```
<210> SEQ ID NO 331
<211> LENGTH: 12
<212> TYPE: PRT
<213> ORGANISM: Homo sapiens

<400> SEQUENCE: 331

Tyr Leu Tyr Gln Ala Pro Gly Ser Leu Ala Leu Tyr
1               5                   10

<210> SEQ ID NO 332
<211> LENGTH: 10
<212> TYPE: PRT
<213> ORGANISM: Homo sapiens

<400> SEQUENCE: 332

Ser Leu Ile Ser Phe Lys Tyr Thr Ser Tyr
1               5                   10

<210> SEQ ID NO 333
<211> LENGTH: 11
<212> TYPE: PRT
<213> ORGANISM: Homo sapiens

<400> SEQUENCE: 333

Leu Ser Asp Pro Gln Ala Glu Leu Gln Phe Tyr
1               5                   10

<210> SEQ ID NO 334
<211> LENGTH: 10
<212> TYPE: PRT
<213> ORGANISM: Homo sapiens

<400> SEQUENCE: 334

Pro Ser Ser Met Pro Glu Cys Leu Ser Tyr
1               5                   10

<210> SEQ ID NO 335
<211> LENGTH: 11
<212> TYPE: PRT
<213> ORGANISM: Homo sapiens

<400> SEQUENCE: 335

Pro Ser Ser Met Pro Glu Cys Leu Ser Tyr Tyr
1               5                   10

<210> SEQ ID NO 336
<211> LENGTH: 11
<212> TYPE: PRT
<213> ORGANISM: Homo sapiens

<400> SEQUENCE: 336

Ala Thr Asn Ile Gln Leu Asn Ile Asp Thr Tyr
1               5                   10

<210> SEQ ID NO 337
<211> LENGTH: 10
<212> TYPE: PRT
<213> ORGANISM: Homo sapiens

<400> SEQUENCE: 337

Phe Thr Glu Ser Asn Gln Tyr Asn Ile Tyr
1               5                   10

<210> SEQ ID NO 338
<211> LENGTH: 10
<212> TYPE: PRT
```

<213> ORGANISM: Homo sapiens

<400> SEQUENCE: 338

Tyr Ser Pro Asp Ser Phe Asn Val Ser Trp
1               5                   10

<210> SEQ ID NO 339
<211> LENGTH: 10
<212> TYPE: PRT
<213> ORGANISM: Homo sapiens

<400> SEQUENCE: 339

Glu Ser Met Asp Ile Phe Pro Leu Gly Trp
1               5                   10

<210> SEQ ID NO 340
<211> LENGTH: 9
<212> TYPE: PRT
<213> ORGANISM: Homo sapiens

<400> SEQUENCE: 340

Ser Val Asp Ser Asn Leu Val Ala Tyr
1               5

<210> SEQ ID NO 341
<211> LENGTH: 10
<212> TYPE: PRT
<213> ORGANISM: Homo sapiens

<400> SEQUENCE: 341

Pro Ala Asn Tyr Leu Gly Lys Met Thr Tyr
1               5                   10

<210> SEQ ID NO 342
<211> LENGTH: 10
<212> TYPE: PRT
<213> ORGANISM: Homo sapiens

<400> SEQUENCE: 342

Gln Thr Tyr Met Asp Gly Leu Leu His Tyr
1               5                   10

<210> SEQ ID NO 343
<211> LENGTH: 9
<212> TYPE: PRT
<213> ORGANISM: Homo sapiens

<400> SEQUENCE: 343

Tyr Phe Gly Asn Tyr Phe Thr Tyr Tyr
1               5

<210> SEQ ID NO 344
<211> LENGTH: 9
<212> TYPE: PRT
<213> ORGANISM: Homo sapiens

<400> SEQUENCE: 344

Ala Val Asn Ala Leu Gln Ser Val Tyr
1               5

<210> SEQ ID NO 345
<211> LENGTH: 12
<212> TYPE: PRT
<213> ORGANISM: Homo sapiens

<400> SEQUENCE: 345

Asn Thr Met Asp Ala Val Pro Arg Ile Asp His Tyr
1               5                   10

<210> SEQ ID NO 346
<211> LENGTH: 10
<212> TYPE: PRT
<213> ORGANISM: Homo sapiens

<400> SEQUENCE: 346

Val Ala Gly Leu Glu Ala Gly Val Leu Tyr
1               5                   10

<210> SEQ ID NO 347
<211> LENGTH: 9
<212> TYPE: PRT
<213> ORGANISM: Homo sapiens

<400> SEQUENCE: 347

Ser Ala Asp His Pro Gly Leu Thr Phe
1               5

<210> SEQ ID NO 348
<211> LENGTH: 10
<212> TYPE: PRT
<213> ORGANISM: Homo sapiens

<400> SEQUENCE: 348

Asp Ser Thr Asp Gly Cys Leu Leu Ser Phe
1               5                   10

<210> SEQ ID NO 349
<211> LENGTH: 9
<212> TYPE: PRT
<213> ORGANISM: Homo sapiens

<400> SEQUENCE: 349

His Leu Leu Ser Val Ser Leu Tyr Tyr
1               5

<210> SEQ ID NO 350
<211> LENGTH: 9
<212> TYPE: PRT
<213> ORGANISM: Homo sapiens

<400> SEQUENCE: 350

Leu Thr Asp Pro Gln Val Ser Tyr Val
1               5

<210> SEQ ID NO 351
<211> LENGTH: 9
<212> TYPE: PRT
<213> ORGANISM: Homo sapiens

<400> SEQUENCE: 351

Val Leu Asp Pro Met Leu Asp Phe Tyr
1               5

<210> SEQ ID NO 352
<211> LENGTH: 10
<212> TYPE: PRT
<213> ORGANISM: Homo sapiens

<400> SEQUENCE: 352

Tyr Pro Val Val Ala Glu Ser Met Tyr
1               5                   10

<210> SEQ ID NO 353
<211> LENGTH: 9
<212> TYPE: PRT
<213> ORGANISM: Homo sapiens

<400> SEQUENCE: 353

Arg Leu Asn Gly Ser Val Ala Ser Tyr
1               5

<210> SEQ ID NO 354
<211> LENGTH: 9
<212> TYPE: PRT
<213> ORGANISM: Homo sapiens

<400> SEQUENCE: 354

Glu Ile Ile Arg Tyr Ile Phe Ala Tyr
1               5

<210> SEQ ID NO 355
<211> LENGTH: 9
<212> TYPE: PRT
<213> ORGANISM: Homo sapiens

<400> SEQUENCE: 355

Met Ala Asp Arg Gly Glu Ala Arg Leu
1               5

<210> SEQ ID NO 356
<211> LENGTH: 9
<212> TYPE: PRT
<213> ORGANISM: Homo sapiens

<400> SEQUENCE: 356

Asn Ser Glu Asn His Ile Leu Lys Tyr
1               5

<210> SEQ ID NO 357
<211> LENGTH: 10
<212> TYPE: PRT
<213> ORGANISM: Homo sapiens

<400> SEQUENCE: 357

Met Ser Pro Asp Ile Ala Leu Leu Tyr Leu
1               5                   10

<210> SEQ ID NO 358
<211> LENGTH: 10
<212> TYPE: PRT
<213> ORGANISM: Homo sapiens

<400> SEQUENCE: 358

Tyr Met Ser Pro Asp Ile Ala Leu Leu Tyr
1               5                   10

<210> SEQ ID NO 359
<211> LENGTH: 9
<212> TYPE: PRT
<213> ORGANISM: Homo sapiens

<400> SEQUENCE: 359

Asn Lys Glu Ile Asn Tyr Phe Met Tyr
1               5

<210> SEQ ID NO 360
<211> LENGTH: 9
<212> TYPE: PRT
<213> ORGANISM: Homo sapiens

<400> SEQUENCE: 360

Arg Phe Asp Asp Ile Asn Gln Glu Phe
1               5

<210> SEQ ID NO 361
<211> LENGTH: 9
<212> TYPE: PRT
<213> ORGANISM: Homo sapiens

<400> SEQUENCE: 361

Phe Thr Ala Glu Glu Gly Gln Leu Tyr
1               5

<210> SEQ ID NO 362
<211> LENGTH: 10
<212> TYPE: PRT
<213> ORGANISM: Homo sapiens

<400> SEQUENCE: 362

Ser Gly Ala Leu Asp Glu Ala Ala Ala Tyr
1               5                   10

<210> SEQ ID NO 363
<211> LENGTH: 9
<212> TYPE: PRT
<213> ORGANISM: Homo sapiens

<400> SEQUENCE: 363

Leu Thr Asp Arg Asp Val Ser Phe Tyr
1               5

<210> SEQ ID NO 364
<211> LENGTH: 9
<212> TYPE: PRT
<213> ORGANISM: Homo sapiens

<400> SEQUENCE: 364

Asp Thr Gly Tyr Leu Gln Leu Tyr Tyr
1               5

<210> SEQ ID NO 365
<211> LENGTH: 9
<212> TYPE: PRT
<213> ORGANISM: Homo sapiens

<400> SEQUENCE: 365

Phe Val Asp Thr Lys Val Pro Glu His
1               5

<210> SEQ ID NO 366
<211> LENGTH: 9
<212> TYPE: PRT
<213> ORGANISM: Homo sapiens

<400> SEQUENCE: 366

Ile Thr Val Asp Val Arg Asp Glu Phe
1               5

```
<210> SEQ ID NO 367
<211> LENGTH: 10
<212> TYPE: PRT
<213> ORGANISM: Homo sapiens

<400> SEQUENCE: 367

Leu Thr Asp Thr Gly Tyr Leu Gln Leu Tyr
1               5                   10

<210> SEQ ID NO 368
<211> LENGTH: 10
<212> TYPE: PRT
<213> ORGANISM: Homo sapiens

<400> SEQUENCE: 368

Glu Ser Ala Ala Thr Gly Gln Leu Asp Tyr
1               5                   10

<210> SEQ ID NO 369
<211> LENGTH: 9
<212> TYPE: PRT
<213> ORGANISM: Homo sapiens

<400> SEQUENCE: 369

Ala Val Met Glu Ala Ala Phe Val Tyr
1               5

<210> SEQ ID NO 370
<211> LENGTH: 9
<212> TYPE: PRT
<213> ORGANISM: Homo sapiens

<400> SEQUENCE: 370

Arg Leu Ser Thr Ile Arg His Leu Tyr
1               5

<210> SEQ ID NO 371
<211> LENGTH: 10
<212> TYPE: PRT
<213> ORGANISM: Homo sapiens

<400> SEQUENCE: 371

Trp Ser Asp Ser Thr Ser Gln Thr Ile Tyr
1               5                   10

<210> SEQ ID NO 372
<211> LENGTH: 9
<212> TYPE: PRT
<213> ORGANISM: Homo sapiens

<400> SEQUENCE: 372

Ser Arg Ser Asp Phe Glu Trp Val Tyr
1               5

<210> SEQ ID NO 373
<211> LENGTH: 10
<212> TYPE: PRT
<213> ORGANISM: Homo sapiens

<400> SEQUENCE: 373

Phe His Ala Asp Ser Asp Asp Glu Ser Phe
1               5                   10

<210> SEQ ID NO 374
<211> LENGTH: 9
```

```
<212> TYPE: PRT
<213> ORGANISM: Homo sapiens

<400> SEQUENCE: 374

Leu Thr Ser Val Val Thr Leu Trp
1               5

<210> SEQ ID NO 375
<211> LENGTH: 9
<212> TYPE: PRT
<213> ORGANISM: Homo sapiens

<400> SEQUENCE: 375

Ala Ser Ser Leu Asp Ser Leu His Tyr
1               5

<210> SEQ ID NO 376
<211> LENGTH: 9
<212> TYPE: PRT
<213> ORGANISM: Homo sapiens

<400> SEQUENCE: 376

Glu Asp Asp Glu Asp Glu Asp Leu Tyr
1               5

<210> SEQ ID NO 377
<211> LENGTH: 11
<212> TYPE: PRT
<213> ORGANISM: Homo sapiens

<400> SEQUENCE: 377

Tyr Ala Asp Pro Ser Ala Asn Arg Asp Leu Leu
1               5                   10

<210> SEQ ID NO 378
<211> LENGTH: 9
<212> TYPE: PRT
<213> ORGANISM: Homo sapiens

<400> SEQUENCE: 378

Thr Ala Lys Ala Pro Ser Thr Glu Tyr
1               5

<210> SEQ ID NO 379
<211> LENGTH: 9
<212> TYPE: PRT
<213> ORGANISM: Homo sapiens

<400> SEQUENCE: 379

Ser Leu Ile Ile Asp Asp Thr Glu Tyr
1               5

<210> SEQ ID NO 380
<211> LENGTH: 9
<212> TYPE: PRT
<213> ORGANISM: Homo sapiens

<400> SEQUENCE: 380

Val Ala Cys Gly Asn Asn Pro Val Tyr
1               5

<210> SEQ ID NO 381
<211> LENGTH: 9
<212> TYPE: PRT
<213> ORGANISM: Homo sapiens
```

<400> SEQUENCE: 381

Glu Thr Ser Phe Ser Thr Ser His Tyr
1               5

<210> SEQ ID NO 382
<211> LENGTH: 9
<212> TYPE: PRT
<213> ORGANISM: Homo sapiens

<400> SEQUENCE: 382

Tyr Glu Pro Ala Thr Met Glu Gln Tyr
1               5

<210> SEQ ID NO 383
<211> LENGTH: 11
<212> TYPE: PRT
<213> ORGANISM: Homo sapiens

<400> SEQUENCE: 383

Pro Pro Asp His Ala Val Gly Arg Thr Lys Tyr
1               5                   10

<210> SEQ ID NO 384
<211> LENGTH: 10
<212> TYPE: PRT
<213> ORGANISM: Homo sapiens

<400> SEQUENCE: 384

Arg Phe Arg Ser Ile Thr Gln Ser Tyr Tyr
1               5                   10

<210> SEQ ID NO 385
<211> LENGTH: 9
<212> TYPE: PRT
<213> ORGANISM: Homo sapiens

<400> SEQUENCE: 385

Ser Ala Asn Ala Leu Ile Leu Thr Tyr
1               5

<210> SEQ ID NO 386
<211> LENGTH: 9
<212> TYPE: PRT
<213> ORGANISM: Homo sapiens

<400> SEQUENCE: 386

Asn Ser Ala Leu Asn Pro Leu Leu Tyr
1               5

<210> SEQ ID NO 387
<211> LENGTH: 11
<212> TYPE: PRT
<213> ORGANISM: Homo sapiens

<400> SEQUENCE: 387

Leu Met Glu Lys Glu Asp Tyr His Ser Leu Tyr
1               5                   10

<210> SEQ ID NO 388
<211> LENGTH: 10
<212> TYPE: PRT
<213> ORGANISM: Homo sapiens

<400> SEQUENCE: 388

Tyr Thr Ala His Val Gly Tyr Ser Met Tyr
1               5                   10

<210> SEQ ID NO 389
<211> LENGTH: 9
<212> TYPE: PRT
<213> ORGANISM: Homo sapiens

<400> SEQUENCE: 389

Tyr Tyr Asp Leu Val Glu Ser Thr Phe
1               5

<210> SEQ ID NO 390
<211> LENGTH: 11
<212> TYPE: PRT
<213> ORGANISM: Homo sapiens

<400> SEQUENCE: 390

Phe Ser Glu Pro Phe His Leu Ile Val Ser Tyr
1               5                   10

<210> SEQ ID NO 391
<211> LENGTH: 9
<212> TYPE: PRT
<213> ORGANISM: Homo sapiens

<400> SEQUENCE: 391

Gly Ser Asn Pro Ala Arg Tyr Glu Phe
1               5

<210> SEQ ID NO 392
<211> LENGTH: 9
<212> TYPE: PRT
<213> ORGANISM: Homo sapiens

<400> SEQUENCE: 392

Thr Gln His Phe Val Gln Glu Asn Tyr
1               5

<210> SEQ ID NO 393
<211> LENGTH: 9
<212> TYPE: PRT
<213> ORGANISM: Homo sapiens

<400> SEQUENCE: 393

Gln Val Trp Gly Gly Gln Pro Val Tyr
1               5

<210> SEQ ID NO 394
<211> LENGTH: 9
<212> TYPE: PRT
<213> ORGANISM: Homo sapiens

<400> SEQUENCE: 394

Gln Val Pro Leu Asp Cys Val Leu Tyr
1               5

<210> SEQ ID NO 395
<211> LENGTH: 9
<212> TYPE: PRT
<213> ORGANISM: Homo sapiens

<400> SEQUENCE: 395

Ile Leu Lys Gly Gly Ser Gly Thr Tyr

```
1               5

<210> SEQ ID NO 396
<211> LENGTH: 9
<212> TYPE: PRT
<213> ORGANISM: Homo sapiens

<400> SEQUENCE: 396

Leu Pro Asp Pro Asn Val Gln Lys Tyr
1               5

<210> SEQ ID NO 397
<211> LENGTH: 9
<212> TYPE: PRT
<213> ORGANISM: Homo sapiens

<400> SEQUENCE: 397

Asn Ser Ala Ile Asn Pro Leu Ile Tyr
1               5

<210> SEQ ID NO 398
<211> LENGTH: 10
<212> TYPE: PRT
<213> ORGANISM: Homo sapiens

<400> SEQUENCE: 398

Tyr Tyr Tyr Asp Thr His Thr Asn Thr Tyr
1               5                   10

<210> SEQ ID NO 399
<211> LENGTH: 9
<212> TYPE: PRT
<213> ORGANISM: Homo sapiens

<400> SEQUENCE: 399

Tyr Val Gly Lys Glu His Met Phe Tyr
1               5

<210> SEQ ID NO 400
<211> LENGTH: 9
<212> TYPE: PRT
<213> ORGANISM: Homo sapiens

<400> SEQUENCE: 400

Asn Thr Asp Asn Asn Leu Ala Val Tyr
1               5

<210> SEQ ID NO 401
<211> LENGTH: 10
<212> TYPE: PRT
<213> ORGANISM: Homo sapiens

<400> SEQUENCE: 401

Val Trp Ser Asn Val Thr Pro Leu Lys Phe
1               5                   10

<210> SEQ ID NO 402
<211> LENGTH: 10
<212> TYPE: PRT
<213> ORGANISM: Homo sapiens

<400> SEQUENCE: 402

Val Leu Tyr Pro Val Pro Leu Glu Ser Tyr
1               5                   10
```

```
<210> SEQ ID NO 403
<211> LENGTH: 12
<212> TYPE: PRT
<213> ORGANISM: Homo sapiens

<400> SEQUENCE: 403

Ser Ala Asp Asp Ile Arg Gly Ile Gln Ser Leu Tyr
1               5                   10

<210> SEQ ID NO 404
<211> LENGTH: 9
<212> TYPE: PRT
<213> ORGANISM: Homo sapiens

<400> SEQUENCE: 404

Phe Val Asp Asn Gln Tyr Trp Arg Tyr
1               5

<210> SEQ ID NO 405
<211> LENGTH: 9
<212> TYPE: PRT
<213> ORGANISM: Homo sapiens

<400> SEQUENCE: 405

Ser Thr Asp Ile Gly Ala Leu Met Tyr
1               5

<210> SEQ ID NO 406
<211> LENGTH: 8
<212> TYPE: PRT
<213> ORGANISM: Homo sapiens

<400> SEQUENCE: 406

Ser Asp Val Thr Pro Leu Thr Phe
1               5

<210> SEQ ID NO 407
<211> LENGTH: 9
<212> TYPE: PRT
<213> ORGANISM: Homo sapiens

<400> SEQUENCE: 407

Val Ser Ile Arg Asn Thr Leu Leu Tyr
1               5

<210> SEQ ID NO 408
<211> LENGTH: 10
<212> TYPE: PRT
<213> ORGANISM: Homo sapiens

<400> SEQUENCE: 408

Val Trp Ser Asp Val Thr Pro Leu Thr Phe
1               5                   10

<210> SEQ ID NO 409
<211> LENGTH: 9
<212> TYPE: PRT
<213> ORGANISM: Homo sapiens

<400> SEQUENCE: 409

Tyr Thr Phe Arg Tyr Pro Leu Ser Leu
1               5

<210> SEQ ID NO 410
```

```
<211> LENGTH: 9
<212> TYPE: PRT
<213> ORGANISM: Homo sapiens

<400> SEQUENCE: 410

Lys Thr Trp Ala His Cys Met Ser Tyr
1               5

<210> SEQ ID NO 411
<211> LENGTH: 10
<212> TYPE: PRT
<213> ORGANISM: Homo sapiens

<400> SEQUENCE: 411

Leu Leu Asp Ala Glu Pro Pro Ile Leu Tyr
1               5                   10

<210> SEQ ID NO 412
<211> LENGTH: 9
<212> TYPE: PRT
<213> ORGANISM: Homo sapiens

<400> SEQUENCE: 412

Ala Ala Ala Ala Asn Ala Gln Val Tyr
1               5

<210> SEQ ID NO 413
<211> LENGTH: 8
<212> TYPE: PRT
<213> ORGANISM: Homo sapiens

<400> SEQUENCE: 413

Thr Asp Thr Leu Ile His Leu Met
1               5

<210> SEQ ID NO 414
<211> LENGTH: 10
<212> TYPE: PRT
<213> ORGANISM: Homo sapiens

<400> SEQUENCE: 414

Leu Thr Glu Gly His Ser Gly Asn Tyr Tyr
1               5                   10

<210> SEQ ID NO 415
<211> LENGTH: 10
<212> TYPE: PRT
<213> ORGANISM: Homo sapiens

<400> SEQUENCE: 415

Val Trp Ser Asp Val Thr Pro Leu Asn Phe
1               5                   10

<210> SEQ ID NO 416
<211> LENGTH: 9
<212> TYPE: PRT
<213> ORGANISM: Homo sapiens

<400> SEQUENCE: 416

Leu Ser Ser Pro Val His Leu Asp Phe
1               5

<210> SEQ ID NO 417
<211> LENGTH: 10
<212> TYPE: PRT
```

```
<213> ORGANISM: Homo sapiens

<400> SEQUENCE: 417

Lys Leu Asp Arg Ser Val Phe Thr Ala Tyr
1               5                   10

<210> SEQ ID NO 418
<211> LENGTH: 10
<212> TYPE: PRT
<213> ORGANISM: Homo sapiens

<400> SEQUENCE: 418

Leu Leu Asp Glu Gly Ala Met Leu Leu Tyr
1               5                   10

<210> SEQ ID NO 419
<211> LENGTH: 10
<212> TYPE: PRT
<213> ORGANISM: Homo sapiens

<400> SEQUENCE: 419

Phe Pro Thr Glu Val Thr Pro His Ala Phe
1               5                   10

<210> SEQ ID NO 420
<211> LENGTH: 9
<212> TYPE: PRT
<213> ORGANISM: Homo sapiens

<400> SEQUENCE: 420

Val Thr Asp Leu Glu Met Pro His Tyr
1               5

<210> SEQ ID NO 421
<211> LENGTH: 11
<212> TYPE: PRT
<213> ORGANISM: Homo sapiens

<400> SEQUENCE: 421

Arg Ser Asp Pro Gly Gly Gly Gly Leu Ala Tyr
1               5                   10

<210> SEQ ID NO 422
<211> LENGTH: 9
<212> TYPE: PRT
<213> ORGANISM: Homo sapiens

<400> SEQUENCE: 422

Ala Leu Asn Pro Tyr Gln Tyr Gln Tyr
1               5

<210> SEQ ID NO 423
<211> LENGTH: 10
<212> TYPE: PRT
<213> ORGANISM: Homo sapiens

<400> SEQUENCE: 423

Leu Leu Asp Glu Gly Ala Lys Leu Leu Tyr
1               5                   10

<210> SEQ ID NO 424
<211> LENGTH: 9
<212> TYPE: PRT
<213> ORGANISM: Homo sapiens
```

```
<400> SEQUENCE: 424

Asn Val Asp Pro Val Gln His Thr Tyr
1               5

<210> SEQ ID NO 425
<211> LENGTH: 10
<212> TYPE: PRT
<213> ORGANISM: Homo sapiens

<400> SEQUENCE: 425

Val Thr Glu Glu Pro Gln Arg Leu Phe Tyr
1               5                   10

<210> SEQ ID NO 426
<211> LENGTH: 10
<212> TYPE: PRT
<213> ORGANISM: Homo sapiens

<400> SEQUENCE: 426

Arg Ser Phe Asn Gly Leu Leu Thr Met Tyr
1               5                   10

<210> SEQ ID NO 427
<211> LENGTH: 9
<212> TYPE: PRT
<213> ORGANISM: Homo sapiens

<400> SEQUENCE: 427

Leu Thr Asp Tyr Ile Asn Ala Asn Tyr
1               5

<210> SEQ ID NO 428
<211> LENGTH: 9
<212> TYPE: PRT
<213> ORGANISM: Homo sapiens

<400> SEQUENCE: 428

Ile Ile Asn Glu Ser Leu Leu Phe Tyr
1               5

<210> SEQ ID NO 429
<211> LENGTH: 10
<212> TYPE: PRT
<213> ORGANISM: Homo sapiens

<400> SEQUENCE: 429

Val Ser Asp Ser Glu Cys Leu Ser Arg Tyr
1               5                   10

<210> SEQ ID NO 430
<211> LENGTH: 9
<212> TYPE: PRT
<213> ORGANISM: Homo sapiens

<400> SEQUENCE: 430

Asn Thr Asp Pro Thr Ala Pro Pro Tyr
1               5

<210> SEQ ID NO 431
<211> LENGTH: 10
<212> TYPE: PRT
<213> ORGANISM: Homo sapiens

<400> SEQUENCE: 431
```

```
Ala Ser Ser Thr Asp Ser Ala Ser Tyr Tyr
1               5                   10

<210> SEQ ID NO 432
<211> LENGTH: 10
<212> TYPE: PRT
<213> ORGANISM: Homo sapiens

<400> SEQUENCE: 432

Leu Gln Ser Ser Gly Leu Thr Leu Leu Leu
1               5                   10

<210> SEQ ID NO 433
<211> LENGTH: 10
<212> TYPE: PRT
<213> ORGANISM: Homo sapiens

<400> SEQUENCE: 433

Glu Leu Ala Gly Ile Gly Ile Leu Thr Val
1               5                   10

<210> SEQ ID NO 434
<211> LENGTH: 9
<212> TYPE: PRT
<213> ORGANISM: Homo sapiens

<400> SEQUENCE: 434

Tyr Leu Leu Pro Ala Ile Val His Ile
1               5
```